United States Patent
Boxer et al.

(10) Patent No.: US 10,836,759 B2
(45) Date of Patent: *Nov. 17, 2020

(54) THIAZOLE DERIVATIVES USEFUL AS MUTANT IDH1 INHIBITORS FOR TREATING CANCER

(71) Applicants: THE UNITED STATES OF AMERICA, AS REPRESENTED BY THE SECRETARY, DEPARTMENT OF HEALTH AND HUMAN SERVICES, Bethesda, MD (US); THE UNIVERSITY OF NORTH CAROLINA AT CHAPEL HILL, Chapel Hill, NC (US)

(72) Inventors: Matthew Brian Boxer, New Market, MD (US); Xiaodong Wang, Chapel Hill, NC (US); Kyle Ryan Brimacombe, Bethesda, MD (US); Mindy Irene Emily Davis, Rockville, MD (US); Yuhong Fang, Rockville, MD (US); Matthew Hall, Rockville, MD (US); Ajit Jadhav, Chantilly, VA (US); Surendra Karavadhi, Gaithersburg, MD (US); Li Liu, Germantown, MD (US); Natalia Martinez, Rockville, MD (US); Andrew Louis McIver, Durham, NC (US); Rajan Pragani, Gaithersburg, MD (US); Jason Matthew Rohde, Poolesvile, MD (US); Anton Simeonov, Bethesda, MD (US); Wei Zhao, Rockville, MD (US); Min Shen, Boyds, MD (US)

(73) Assignees: THE UNIVERSITY OF NORTH CAROLINA AT CHAPEL HILL, Chapel Hill, NC (US); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/312,206

(22) PCT Filed: Jun. 21, 2017

(86) PCT No.: PCT/US2017/038549
§ 371 (c)(1),
(2) Date: Dec. 20, 2018

(87) PCT Pub. No.: WO2017/223202
PCT Pub. Date: Dec. 28, 2017

(65) Prior Publication Data
US 2019/0241551 A1 Aug. 8, 2019

Related U.S. Application Data

(60) Provisional application No. 62/353,298, filed on Jun. 22, 2016.

(51) Int. Cl.
| | |
|---|---|
| *C07D 417/14* | (2006.01) |
| *C07D 487/08* | (2006.01) |
| *C07D 417/04* | (2006.01) |
| *A61K 31/496* | (2006.01) |
| *A61K 31/4995* | (2006.01) |

(52) U.S. Cl.
CPC ......... *C07D 417/14* (2013.01); *A61K 31/496* (2013.01); *A61K 31/4995* (2013.01); *C07D 417/04* (2013.01); *C07D 487/08* (2013.01); *C07B 2200/07* (2013.01)

(58) Field of Classification Search
CPC ... A61K 31/496; A61K 31/551; C07D 417/14
USPC .............. 514/216, 252.13; 540/556; 544/360
See application file for complete search history.

(56) References Cited

U.S. PATENT DOCUMENTS 8,440,677 B2    5/2013   Evarts et al.

FOREIGN PATENT DOCUMENTS

WO     2016106331 A1     6/2016

OTHER PUBLICATIONS

International Search Report and Written Opinion for International Application No. PCT/US2017/038549, International Filing Date—Jun. 21, 2017; dated Aug. 3, 2017; 5 pages.
Baisong Zhen et al., "Crystallographic Investigation and Selective Inhibition of Mutant Isocitrate Dehydrogenase,"ACS Medicinal Chemistry Letters, vol. 4, No. 6. Jun. 13, 2013, 5 pages.

*Primary Examiner* — Jeffrey H Murray
(74) *Attorney, Agent, or Firm* — Cantor Colburn LLP

(57) ABSTRACT

A compound of Formula II or a pharmaceutically acceptable salt thereof, wherein CyN is a cyclic amine group bound via a nitrogen atom; X is C or N; $R^1$ and $R^2$ are each independently a halogen, CN, $CF_3$, $CHF_2$, $CH_2F$, a $C_1$-C10alkyl group, a C1-$C_{10}$alkoxy group, a di($C_1$-$C_5$alkyl)amino; m and n are each independently 1, 2, or 3, and represents either a single bond or a double bond, wherein the racemic mixture of 3-(4-(4-chlorophenyl)thiazol-2-yl)-1-(2-ethyl-5-methoxyphenyl)-6-(2-methylprop-1-en-1-yl)-5-(piperazine-1-carbonyl)pyridin-2(1H)-one atropisomers is excluded.

20 Claims, No Drawings

THIAZOLE DERIVATIVES USEFUL AS MUTANT IDH1 INHIBITORS FOR TREATING CANCER

CROSS REFERENCE TO RELATED APPLICATIONS

This application is a National Stage application of PCT/US2017/038549, filed Jun. 21, 2017, which claims priority to U.S. Provisional Application No. 62/353,298 filed Jun. 22, 2016, and all the benefits accruing therefrom under 35 U.S.C. § 119, the content of which is incorporated by reference in its entirety.

BACKGROUND

Isocitrate dehydrogenase 1 (IDH1, protein accession number NP_005887.2) is an enzyme whose normal function is to convert isocitrate to α-ketoglutarate. Mutated forms of this enzyme, most commonly IDH1(R132H) in which arginine 132 is mutated to histidine, are common in a variety of cancers including glioma, cholangiocarcinoma, chondrosarcoma, and AML. The IDH1(R132H, R132C, R132S) mutation and similar IDH1 mutations are gain-of-function mutations which result in the enzyme gaining the ability to catalyze the NADPH-dependent reduction of α-ketoglutarate to R-2-hydroxyglutarate (2HG). Elevated levels of 2HG have been shown to lead to an elevated risk of brain tumors in humans. 2HG is described as an oncometabolite, and a proposed mode of action is that it leads to hypermethylation of histones and causing inhibited cell differentiation and the development of cancerous cells.

Mutant IDH1 is an attractive target for anti-cancer therapeutics. Inhibition of mutant IDH1 reduces levels of 2HG. It is expected that lower 2HG levels will result in fewer undifferentiated cancer cells. Furthermore, inhibition of mutant IDH1 is expected to have little effect on non-cancerous cells, as these cells do not express the IDH1 mutation resulting in lower toxicity than typical cytotoxic anticancer agents.

For these reasons mutant IDH1 inhibitors are needed as anti-cancer therapeutics. This disclosure provides mutant IDH1 inhibitors and possesses additional advantages which are set forth in the following descriptions

SUMMARY

The disclosure includes a compound of Formula II:

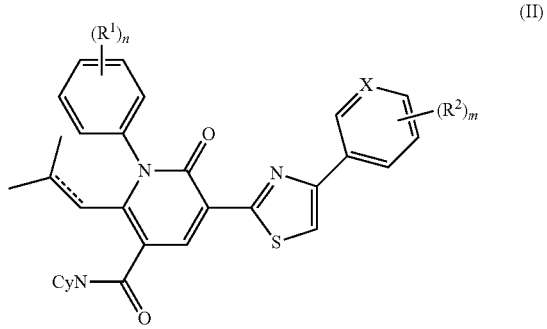

(II)

or a pharmaceutically acceptable salt thereof, wherein

CyN is a cyclic amine group bound via a nitrogen atom that is optionally substituted with one or more substituents independently chosen from halogen, $C_1$-$C_2$alkyl, and $C_1$-$C_2$alkoxy;

X is C or N;

$R^1$ and $R^2$ are each independently a halogen, CN, $CF_3$, $CHF_2$, $CH_2F$, a $C_1$-$C_{10}$alkyl group, a $C_1$-$C_{10}$alkoxy group, a di($C_1$-$C_5$alkyl)amino;

m and n are each independently 1, 2, or 3; and

----- represents either a single bond or a double bond, wherein the racemic mixture of 3-(4-(4-chlorophenyl)thiazol-2-yl)-1-(2-ethyl-5-methoxyphenyl)-6-(2-methylprop-1-en-1-yl)-5-(piperazine-1-carbonyl)pyridin-2(1H)-one atropisomers is excluded.

Pharmaceutical compositions comprising a compound or salt of Formula II together with a pharmaceutically acceptable carrier are also disclosed.

Methods of treating a cancer characterized by the presence of an IDH1 mutation, wherein the IDH1 mutation results in a new ability of the enzyme to catalyze the NADPH-dependent reduction of α-ketoglutarate to R(−)-2-hydroxyglutarate in a patient, comprising the step of administering to the patient in need thereof a compound of Formula II or a salt thereof, are also disclosed.

In some embodiments the IDH1 mutation is an IDH1 R132H or IDH1 R132C mutation.

Methods of treating cancer characterized by the presence of an IDH1 mutation, such as glioma (glioblastoma), acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer, comprising administering a therapeutically effective amount of a compound or salt of the disclosure to a patient in need of such treatment are also disclosed. The disclosure also includes methods of treating Ollier disease and Mafucci syndrome comprising administering a therapeutically effective amount of a compound of the disclosure to a patient in need of such treatment.

DETAILED DESCRIPTION

Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or." The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended for illustration and does not pose a limitation on the scope of the disclosure unless otherwise claimed. No language in the specification should be construed as indicating any non-claimed element as essential to the practice of the invention. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Formula I includes all pharmaceutically acceptable salts of Formula I.

Formula II includes all pharmaceutically acceptable salts of Formula II and all subformulae such as Formulas II-A and II-B.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_8$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkenyl" is a branched or straight chain aliphatic hydrocarbon group having one or more carbon-carbon double bonds that may occur at any stable point along the chain, having the specified number of carbon atoms. Examples of alkenyl include, but are not limited to, ethenyl and propenyl.

"Alkynyl" is a branched or straight chain aliphatic hydrocarbon group having one or more double carbon-carbon triple bonds that may occur at any stable point along the chain, having the specified number of carbon atoms.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound to the group it substitutes by a sulfur bridge (—S—).

"Halo" or "halogen" means fluoro, chloro, bromo, or iodo.

"Cyclic amine" (CyN) is a nitrogen containing heterocycle that is a saturated, unsaturated, or aromatic cyclic group having the indicated number of ring atoms containing from 1 to about 3 additional heteroatoms chosen from N, O, and S, with remaining ring atoms being carbon. Cyclic amine groups include bridged cyclic amine groups such as 3,8-diazabicyclo[3.2.1]octane. Examples of cyclic amine groups include piperazine, piperidine, thiazole, and bridged cyclic amine groups such as 3,8-diazabicyclo[3.2.1]octane groups.

"Pharmaceutical compositions" means compositions comprising at least one active agent, such as a compound or salt of Formula (I), and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any cancer symptom, slow cancer progression or cause cancer regression. In certain embodiments treatment of the cancer may be commenced before the patient presents symptoms of the disease.

A "therapeutically effective amount" of a pharmaceutical composition means an amount effective, when administered to a patient, to provide a therapeutic benefit such as an amelioration of symptoms, decrease cancer progression, or cause cancer regression.

A significant change is any detectable change that is statistically significant in a standard parametric test of statistical significance such as Student's T-test, where $p<0.05$.

Chemical Description

Compounds of Formula I or Formula II may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, tautomers, polymorphs, free compound and salts) of an active agent may be employed either alone or in combination.

The term "chiral" refers to molecules, which have the property of non-superimposability of the mirror image partner.

The term "atropisomers" refers to conformational stereoisomers which occur when rotation about a single bond in the molecule is prevented, or greatly slowed, as a result of steric interactions with other parts of the molecule and the substituents at both ends of the single bond are asymmetrical, i.e., they do not require a stereocenter. Where the rotational barrier about the single bond is high enough, and interconversion between conformations is slow enough, separation and isolation of the isomeric species may be permitted. Atropisomers may be enantiomers without a single asymmetric atom.

As used herein, an atropisomer "substantially free" of its corresponding enantiomer means that the composition contains at least 90% by weight of one atropisomer, and 10% by weight or less of its stereoisomeric atropisomer. In some embodiments, the composition contains at least 95% by weight of one atropisomer and 5% by weight or less of its stereoisomer. In some embodiments, the composition contains at least 98% by weight of one atropisomer and 2% by weight or less of its stereoisomer. Alternatively, the relative amounts of the predominant isomer and any of the minor enantiomer is at least 9:1, or at least 19:1, or at least 98:2. In some embodiments, the composition contains at least 99% by weight of one atropisomer and 1% by weight or less of its stereoisomer. In some embodiments, the composition contains at least 99.5% by weight of one atropisomer and 0.5% by weight or less of its stereoisomer.

An atropisomer which is present "in excess" of its corresponding enantiomer or an "enantioenriched mixture" means that the atropisomer is present in an amount greater than its enantiomer, making the atropisomer mixture optically active. Typically this means the compound present "in excess" predominates by at least a 60/40 ratio over its enantiomer.

The energy barrier to thermal racemization of atropisomers may be determined by the steric hindrance to free rotation of one or more bonds forming a chiral axis. Certain biaryl compounds exhibit atropisomerism where rotation around an interannular bond lacking C2 symmetry is restricted. The free energy barrier for isomerization (enantiomerization) is a measure of the stability of the interannular bond with respect to rotation. Optical and thermal excitation can promote racemization of such isomers, dependent on electronic and steric factors.

Ortho-substituted compounds including two aromatic or pseudo-aromatic rings may exhibit this type of conformational, rotational isomerism. Such compounds are enantiomeric, chiral atropisomers where the $sp^2$-$sp^2$ carbon-carbon or the $sp^2$-$sp^2$ carbon-nitrogen, interannular bond between the rings has a sufficiently high energy barrier to prevent free rotation, and where ortho-substituents at the aromatic or pseudo-aromatic rings render the molecule asymmetric.

The steric interaction between ortho-substituents of different rings is large enough to make the planar conformation an energy maximum. Two non-planar, axially chiral enantiomers then exist as atropisomers when their interconversion is slow enough such that they can be isolated free of each other. By one definition, atropisomerism is defined to exist where the isomers have a half-life, $t_{1/2}$, of at least 1,000 seconds, which is a free energy barrier of 22.3 kcal mol$^{-1}$ (93.3 kJ mol$^{-1}$) at 300 K (Oki, M. "Recent Advances in Atropisomerism," *Topics in Stereochemistry* (1983) 14:1). Bold lines and dashed lines in the figures shown above indicate those moieties, or portions of the molecule, which are sterically restricted due to a rotational energy barrier. Bolded moieties exist orthogonally above the plane of the page, and dashed moieties exist orthogonally below the plane of the page. The 'flat' part of the molecule is in the plane of the page.

For purposes of the invention, the atropisomers are preferably sufficiently stable to be stored and used without substantial thermal interconversion. Typically, the atropisomers have a half-life of greater than 1 week when in solid form at room temperature.

The term "stereoisomers" refers to compounds, which have identical chemical constitution, but differ with regard to the arrangement of the atoms or groups in space.

The term "diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

The term "enantiomers" refers to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

"Tautomers" or "tautomeric forms" are constitutional isomers that readily interconvert, commonly by the migration of a hydrogen atom combined with a switch of a single bond and a double bond.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth Editors, Wiley-VCH, 2002.

Chemical Description

Molecules which inhibit mutant IDH1 are disclosed herein.

In addition to compounds of Formula I, Formula II, shown in the SUMMARY section, the disclosure also includes compounds in which the variables, e.g. A, B, $X^1$, $X^2$, Y, Z, $R^1$ to $R^{26}$ carry the following definitions. The disclosure includes all combinations of these definitions so long as a stable compound results. The disclosure includes the following particular embodiments of Formula (I)

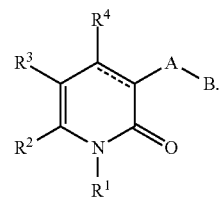

Formula (I)

In some embodiments the compound of Formula I is a compound of Formula (IA)

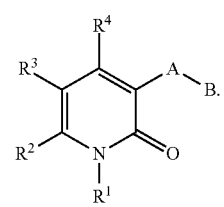

Formula (IA)

$R^1$ is a phenyl or pyridyl substituted by 0-3 substituents independently chosen from hydroxyl, halogen, cyano, nitro, $C_1$-$C_6$alkyl, $C_1$-$C_6$alkylthio, $C_1$-$C_6$alkoxy, $C_1$-$C_2$haloalkyl, $C_1$-$C_2$haloalkoxy, —($C_0$-$C_6$alkyl)$C_3$-$C_6$cycloalkyl, —O—($C_0$-$C_6$alkyl) $C_3$-$C_6$cycloalkyl, —($C_0$-$C_2$alkyl)phenyl, —O—($C_0$-$C_2$alkyl)phenyl, —($C_0$-$C_6$alkyl)$CO_2R^5$, —($C_0$-$C_6$alkyl)C(O)NR$^5$R$^6$, —($C_1$-$C_6$alkyl)OR$^5$, —($C_0$-$C_6$alkyl)NR$^5$R$^6$, and —($C_0$-$C_6$alkyl)NR$^5$C(O)R$^6$.

$R^2$ is $C_1$-$C_6$alkyl, $C_2$-$C_6$alkenyl, $C_2$-$C_6$alkynyl, or —($C_0$-$C_6$alkyl)cycloalkyl.

$R^3$ is C(O)NR$^7$R$^8$.

$R^4$ is hydrogen or $C_1$-$C_6$alkyl.

A is a monocyclic heteroaryl of 5 or 6 ring atoms having 1 to 4 ring atoms independently chosen from N, O, and S, wherein A is substituted with 0-2 substituents independently chosen from halogen, cyano, $C_1$-$C_6$alkyl, $C_1$-$C_6$alkoxy, $C_1$-$C_6$haloalkyl, and $C_1$-$C_6$haloalkoxy, —($C_0$-$C_6$alkyl)cycloalkyl, —O($C_0$-$C_6$alkyl)cycloalkyl, —($C_0$-$C_6$alkyl) $CO_2R^5$, and —($C_0$-$C_6$alkyl)C(O)NR$^5$R$^6$.

B is a phenyl or pyridyl substituted with 0-3 substituents independently chosen from hydroxyl, halogen, cyano, $C_1$-$C_6$alkyl, $C_1$-$C_6$alkoxy, $C_1$-$C_6$haloalkyl, $C_1$-$C_6$haloalkoxy, —($C_0$-$C_6$alkyl)cycloalkyl, —O—($C_0$-$C_6$alkyl)cycloalkyl, —($C_0$-$C_6$alkyl)phenyl, —O—($C_0$-$C_6$alkyl)phenyl, —($C_0$-$C_6$alkyl)cycloalkyl, —O($C_0$-$C_6$alkyl)cycloalkyl, —($C_0$-$C_6$alkyl)$CO_2R^9$, —($C_0$-$C_6$alkyl)C(O)NR$^9$R$^{10}$, —($C_0$-$C_6$alkyl)NR$^9$R$^{10}$, and —($C_1$-$C_6$alkyl)OR$^9$.

In some embodiments the compound of Formula I is a compound of Formula (II) or a pharmaceutically acceptable salt thereof:

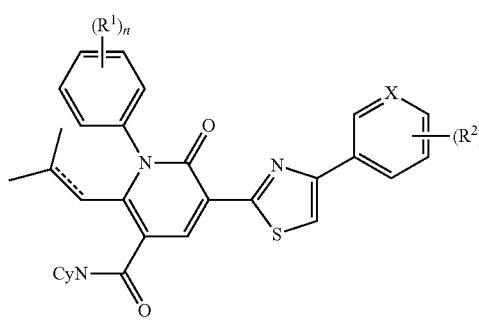

(II)

CyN is a cyclic amine group bound via a nitrogen atom that is optionally substituted with one or more substituents independently chosen from halogen, $C_1$-$C_2$alkyl, and $C_1$-$C_2$alkoxy. In certain embodiments CyN is unsubstituted. In certain embodiments CyN is substituted with one methyl group.

X is C or N.

$R^1$ and $R^2$ are each independently a halogen, CN, $CF_3$, $CHF_2$, $CH_2F$, a $C_1$-$C_{10}$alkyl group, a $C_1$-$C_{10}$alkoxy group, a di($C_1$-$C_5$alkyl)amino.

m and n are each independently 1, 2, or 3.

----- represents either a single bond or a double bond,

In some embodiments the compound of Formula I is an atropisomer of Formula II-A:

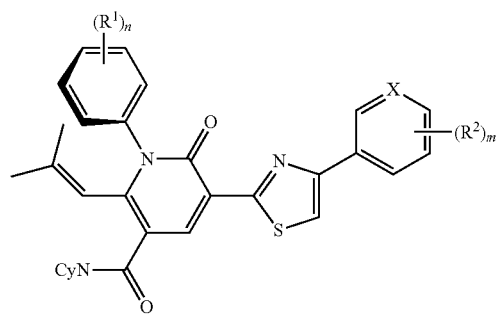

(II-A)

In Formula II-A, at least one $R^1$ group is an ortho substituent.

The atropisomer of Formula II-A is present in excess of its corresponding enantiomer.

In some other embodiments the compound of Formula I is an atropisomer of Formula II-B:

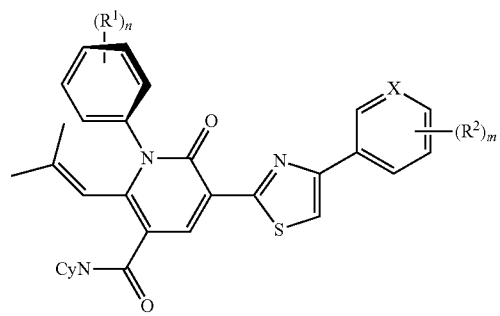

(II-B)

In Formula II-B, at least one $R^1$ group is an ortho substituent.

The atropisomer of Formula II-B is present in excess of its corresponding enantiomer.

In some embodiments the compound of Formula I is an atropisomer of Formula II-C:

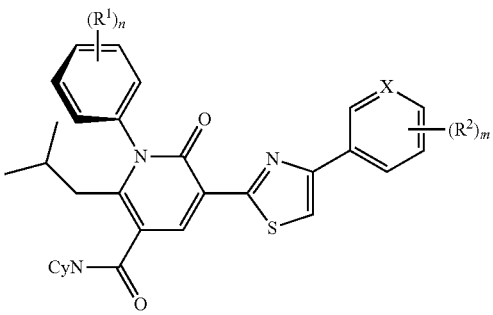

(II-C)

The atropisomer of Formula II-C is present in excess of its corresponding enantiomer.

In some embodiments the compound of Formula I is an atropisomer of Formula II-D:

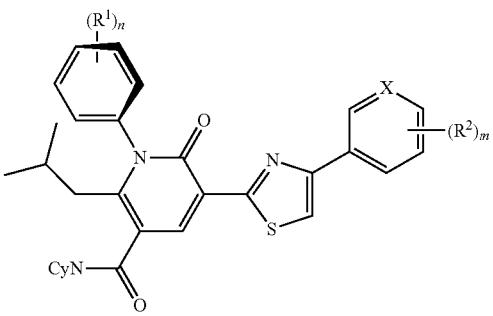

(II-D)

The atropisomer of Formula II-D is present in excess of its corresponding enantiomer.

The atropisomer compound or salt of Formulas II-A to II-D is substantially free of the corresponding enantiomer.

In Formulas II and II-A to II-D, m is 1 and $R^2$ is a 4-substituent.

$R^2$ is 4-Cl, 4-$CF_3$, 4-$CHF_2$, 4-$CH_3O$, or 4-CN.

X is C and $R^2$ is 4-Cl, 4-$CF_3$, 4-$CHF_2$, or 4-NC.

X is N and $R^2$ is 4-$CF_3$, 4-$CHF_2$, or 4-$CH_3O$.

n is 2 and $R^1$ is 2,2-$C_2H_5$; or 2-$C_2H_5$, 5-$CH_3O$; or 2-$C_2H_5$, 5-Cl; or 2-Cl, 5-$(CH_3)_2N$; or 2-$C_2H_5O$, 5-$C_2H_5O$; or 2-$C_2H_5O$, 5-Cl; or 3-$C_2H_5O$, 5-NC, or di-2,6-$C_2H_5$.

CyN— is:

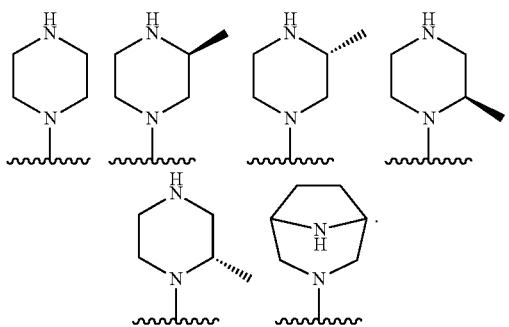

The atropisomer of Formula II-A is one of the following compounds:
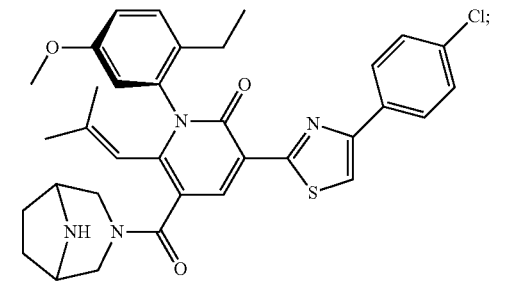
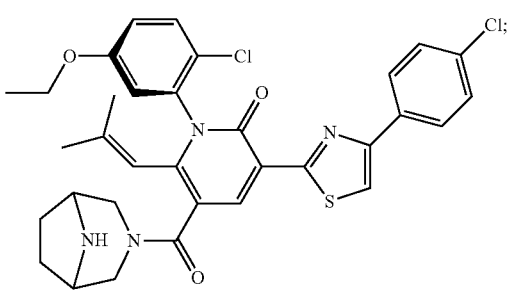
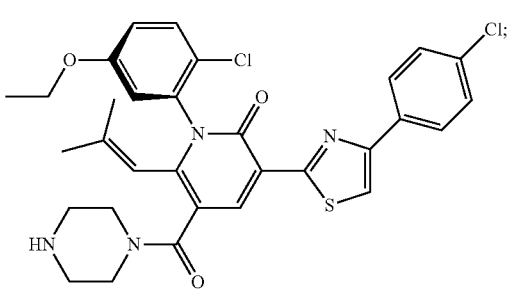
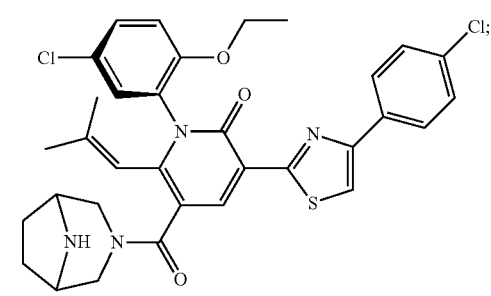
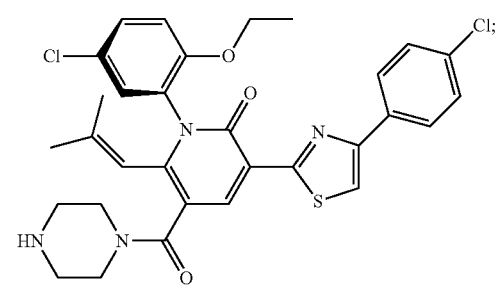
-continued
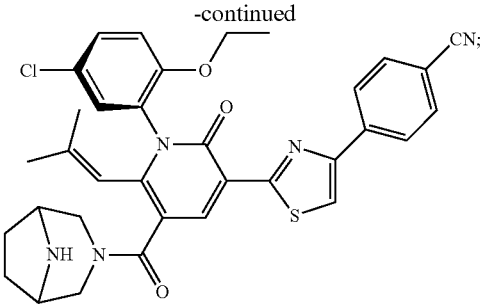
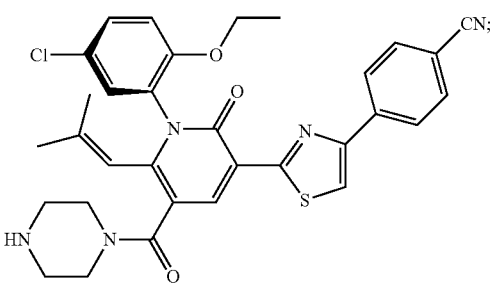
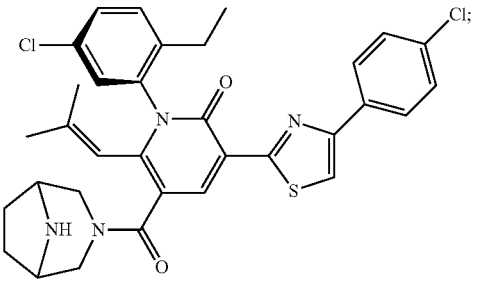
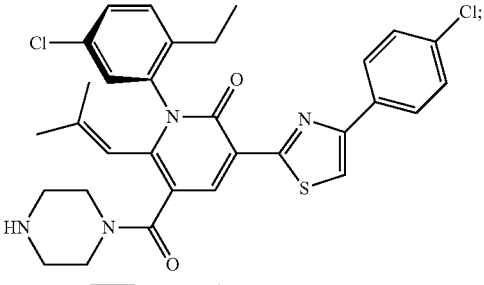
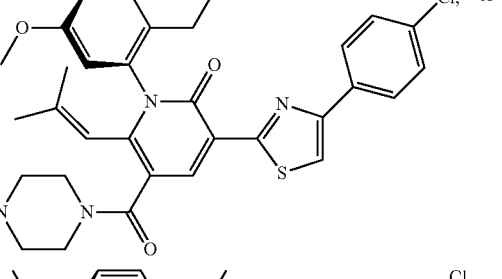
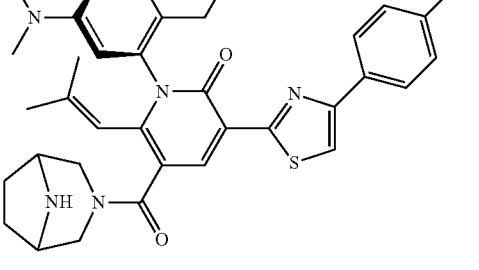

The atropisomer of Formula II-B is one of the following compounds:
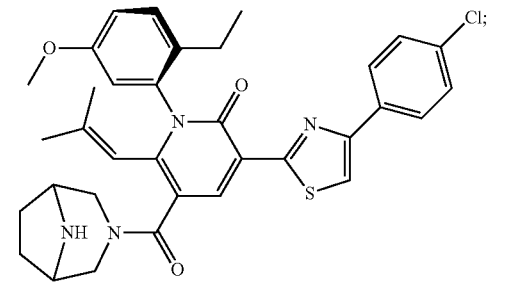
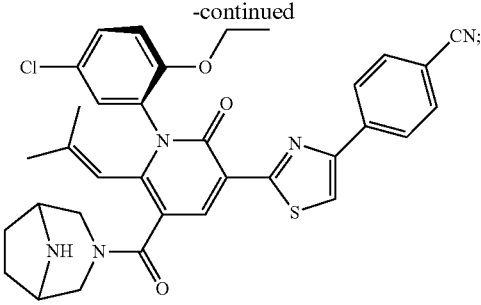
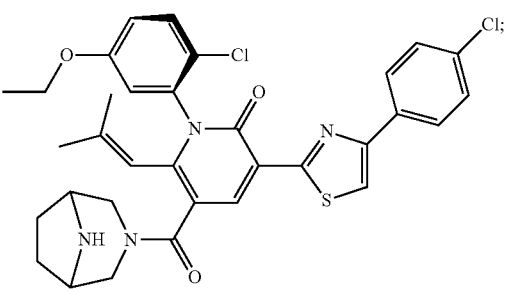
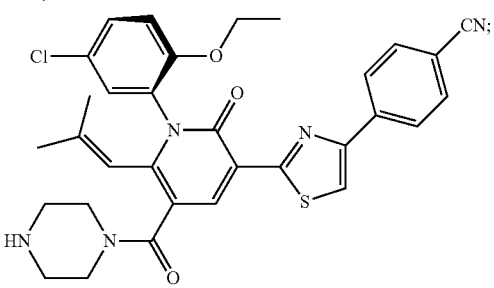
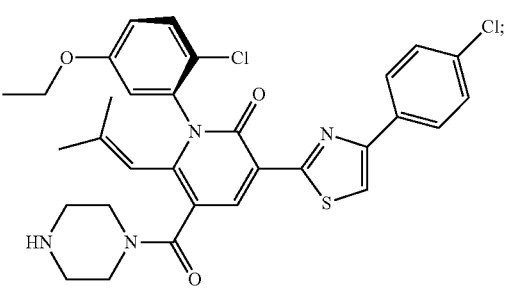
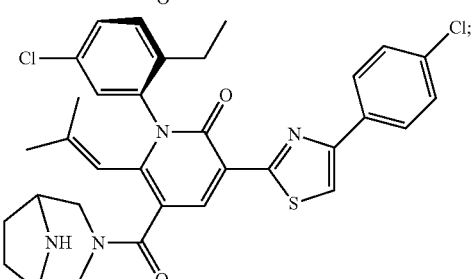
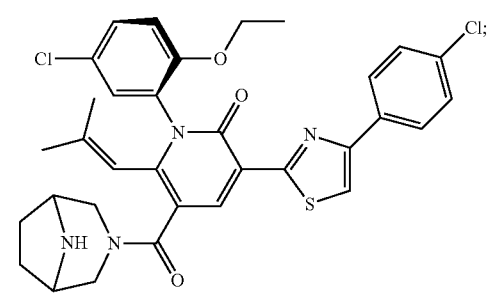
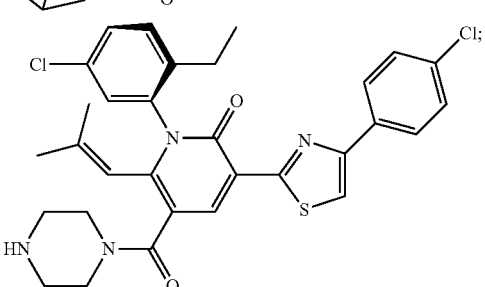
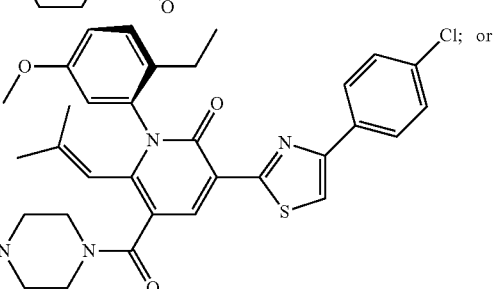
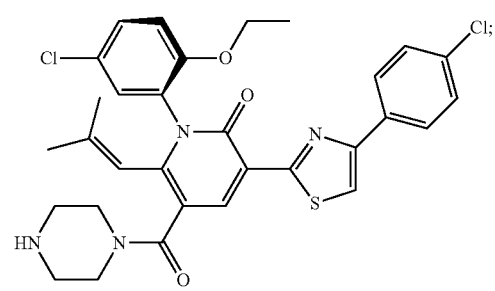
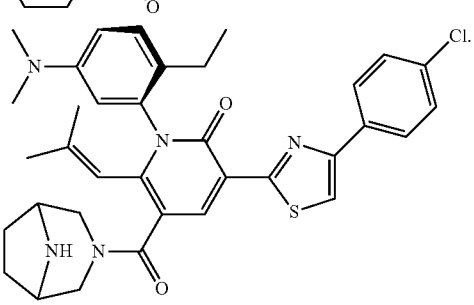

The atropisomer of Formula II-C is one of the following compounds:

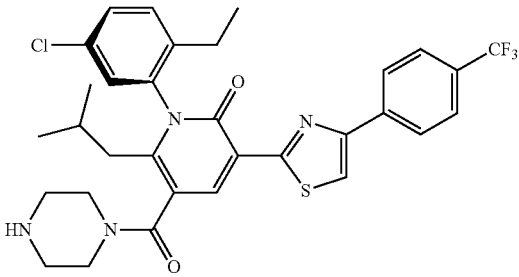

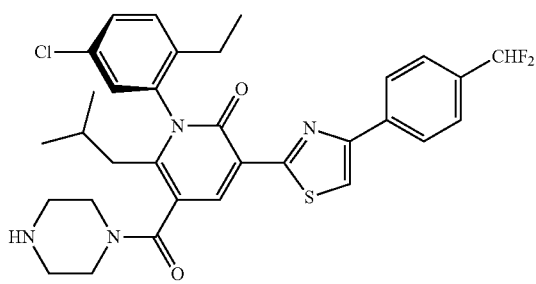

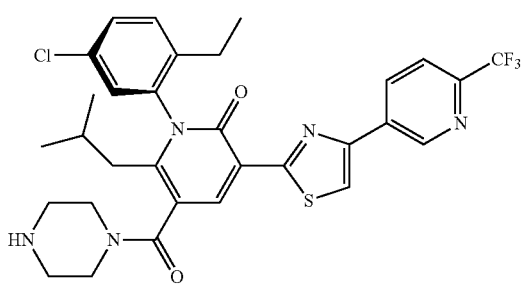

The atropisomer of Formula II-D is one of the following compounds:

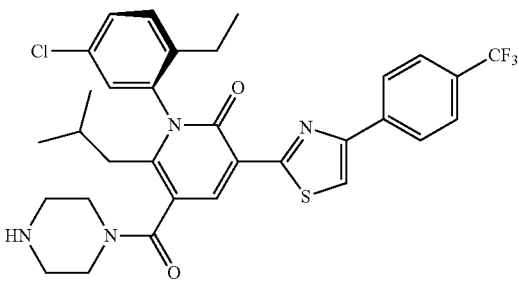

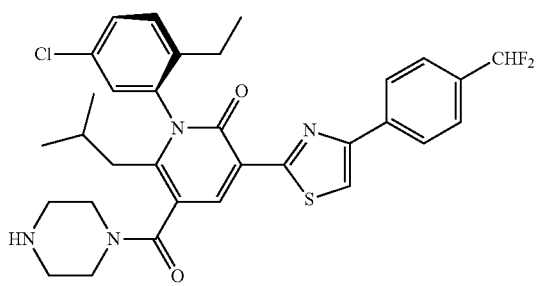

-continued

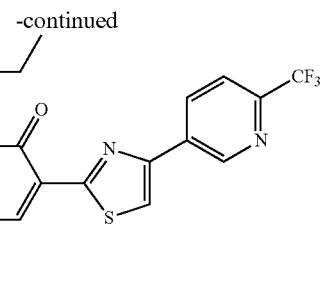

The disclosure includes compounds having a structure shown in Table 1 or a pharmaceutically acceptable salt thereof.

Treatment Methods

The compounds of Formula I, Formula II, or Formulas II-A and II-B or a salt thereof, as well as pharmaceutical compositions comprising the compounds, are useful for treating cancer, including effecting tumor regression in vivo. The method of treating cancer or effecting tumor regression comprises providing to a patient an effective amount of a compound of Formula I, Formula II, or Formulas II-A and II-B. In an embodiment the patient is a mammal, and more specifically a human. The disclosure also provides methods of treating non-human patients such as companion animals, e.g. cats, dogs, and livestock animals. An effective amount of a pharmaceutical composition may be an amount sufficient to inhibit the progression of cancer or a cancerous tumor; or cause a regression of a cancer or a cancerous tumor.

An effective amount of a compound or pharmaceutical composition described herein will also provide a sufficient concentration of a compound of Formula I, Formula II, or Formulas II-A and II-B when administered to a patient. A sufficient concentration is a concentration of the compound in the patient's body necessary to combat the disorder. Such an amount may be ascertained experimentally, for example by assaying blood concentration of the compound, or theoretically, by calculating bioavailability.

Methods of treatment include providing certain dosage amounts of a compound of Formula I, Formula II, or Formulas II-A and II-B to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I, Formula II, or Formulas II-A and II-B are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

The compounds of Formula I, Formula II, or Formulas II-A and II-B may be used to treat cancers and effect regression of tumors, including cancerous tumors. In certain embodiments, the patient is suffering from a cell proliferative disorder or disease. The cell proliferative disorder can be cancer, tumor (cancerous or benign), neoplasm, neovascularization, or melanoma. Cancers for treatment include both solid and disseminated cancers. Exemplary solid cancers (tumors) that may be treated by the methods provided herein include e.g. cancers of the lung, prostate, breast, liver, colon, breast, kidney, pancreas, brain, skin including malignant melanoma and Kaposi's sarcoma, testes or ovaries, carcinoma, kidney cancer (renal cell), and sarcoma. Cancers that may be treated with a compound of Formula I, Formula II, or Formulas II-A and II-B also include bladder cancer, breast cancer, colon cancer, endometrial cancer, lung cancer, bronchial cancer, melanoma, Non-Hodgkins lymphoma, cancer of the blood, pancreatic cancer, prostate cancer, thyroid cancer, brain or spinal cancer, and leukemia. Exemplary disseminated cancers include leukemias or lymphoma including Hodgkin's disease, multiple myeloma and mantle cell lymphoma (MCL), chronic lymphocytic leukemia (CLL), T-cell leukemia, multiple myeloma, and Burkitt's lymphoma. Particularly included herein are methods of treating cancer by providing a compound of Formula I, Formula II, or Formulas II-A and II-B to a patient wherein the cancer is a solid tumor or disseminated cancer.

Further included are methods of treating cancer by providing a compound of Formula I, Formula II, or Formulas II-A and II-B to a patient wherein the cancer is selected from glioma (glioblastoma), acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer.

The compounds of the disclosure are also useful for treating disorders that cause enchondromas such as Ollier's disease and Maffucci syndrome.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula I, Formula II, or Formulas II-A and II-B may be administered singularly (i.e., sole therapeutic agent of a regime) to treat diseases and conditions such as undesired cell proliferation, cancer, and/or tumor growth or may be administered in combination with another active agent. One or more compounds of Formula I, Formula II, or Formulas II-A and II-B may be administered in coordination with a regime of one or more other chemotherapeutic agents such as an antineoplastic drug, e.g., an alkylating agent (e.g., mechloroethamine, chlorambucil, cyclophosamide, melphalan, or ifosfamide), an antimetabolite such as a folate antagonist (e.g., methotrexate), a purine antagonist (e.g. 6-mercaptopurine) or a pyrimidine antagonist (e.g., 5-fluorouracil). Other, non-limiting examples of chemotherapeutic agents that might be used in coordination with one or more compounds of Formula I, Formula II, or Formulas II-A and II-B include taxanes and topoisomerase inhibitors. In addition, other non-limiting examples of active therapeutics include biological agents, such as monoclonal antibodies or IgG chimeric molecules, that achieve their therapeutic effect by specifically binding to a receptor or ligand in a signal transduction pathway associated with cancer (e.g. therapeutic antibodies directed against CD20 (e.g. rituximab) or against VEGF (e.g. bevacizumab)).

Methods of treatment provided herein are also useful for treatment of mammals other than humans, including for veterinary applications such as to treat horses and livestock e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

In an embodiment, the invention provides a method of treating a cancer disorder in a patient identified as in need of such treatment, the method comprising providing to the patient an effective amount of a compound of Formula I, Formula II, or Formulas II-A and II-B. The compounds and salts of Formula I, Formula II, or Formulas II-A and II-B provided herein may be administered alone, or in combination with one or more other active agent.

In an embodiment, the cancer to be treated is characterized by a mutant allele of IDH1 wherein the IDH1 mutation results in a new ability of the enzyme to catalyze the NADPH-dependent reduction of α-ketoglutarate to R(−)-2-hydroxyglutarate in a subject. In one aspect of this embodiment, the mutant IDH1 has an R132X mutation. In one aspect of this embodiment, the R132X mutation is selected from R132H, R132C, R132L, R132V, R132S and R132G. In another aspect, the R132X mutation is R132H or R132C. In yet another aspect, the R132X mutation is R132H.

In one aspect of this embodiment, the efficacy of cancer treatment is monitored by measuring the levels of 2HG in the subject. Typically levels of 2HG are measured prior to treatment, wherein an elevated level is indicative of the need to use a compound of Formula I to treat the cancer. Once the elevated levels are established, the level of 2HG is determined during the course of and/or following termination of treatment to establish efficacy. In certain embodiments, the level of 2HG is only determined during the course of and/or following termination of treatment. A reduction of 2HG levels during the course of treatment and following treatment is indicative of efficacy. Similarly, a determination that 2HG levels are not elevated during the course of or following treatment is also indicative of efficacy. Typically, these 2HG measurements will be utilized together with other well-known determinations of efficacy of cancer treatment, such as reduction in number and size of tumors and/or other cancer-associated lesions, improvement in the general health of the subject, and alterations in other biomarkers that are associated with cancer treatment efficacy. In different embodiments 2HG can be detected in a sample by direct measurement, or by measurement of derivatives or metabolites, such as by HPLC methods.

EXAMPLES

Abbreviations

BSA Bovine Serium Albumin
DCM Dichloromethane
DMF Dimethylformamide
DMSO Dimethyl Sulfoxide
EtOAc Ethyl Acetate
LCMS Liquid Chromatography/Mass Spectrometry
NADPH Nicotinamide Adenine Dinucleotide Phosphate, Reduced Form
NMR Nuclear Magnetic Resonance
RPMI Roswell Park Memorial Institute medium (cell culture medium)

THF Tetrahydrofuran
TFA Trifluoroacetic acid

GENERAL METHODS

All air- or moisture-sensitive reactions were performed under positive pressure of nitrogen with oven-dried glassware. Anhydrous solvents or reagents such as dichloromethane, N,N-dimethylformamide (DMF), acetonitrile, methanol, and triethylamine were purchased from Sigma-Aldrich. Preparative purification was performed on a Waters semi-preparative HPLC system. The column used was a Phenomenex Luna C18 (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nM). Analytical analysis was performed on an Agilent LC/MS (Agilent Technologies, Santa Clara, Calif.). Purity analysis was determined using a 7 minute gradient of 4% to 100% acetonitrile (containing 0.025% trifluoroacetic acid) and water (containing 0.05% trifluoroacetic acid) with an 8 minute run time at a flow rate of 1 mL/min. A Phenomenex Luna C18 column (3 micron, 3×75 mm) was used at a temperature of 50° C. using an Agilent Diode Array Detector. Mass determination was performed using an Agilent 6130 mass spectrometer with electrospray ionization in the positive mode. $^1$H NMR spectra were recorded on Varian 400 MHz spectrometers. Chemical shifts are reported in ppm with non-deuterated solvent (DMSO-h6 at 2.50 ppm) as internal standard for DMSO-d6 solutions. All of the analogs tested in the biological assays have a purity greater than 95% based on LCMS analysis. High resolution mass spectrometry was recorded on Agilent 6210 Time-of-Flight LC/MS system. A gradient of 4% to 100% acetonitrile (containing 0.025% trifluoroacetic acid) and water (containing 0.05% trifluoroacetic acid) with a 4.5 minute run time at a flow rate of 1 mL/min was used. An Agilent Extend-C18 column (3.5 micron, 4.6×100 mm) was used at a temperature of 50° C. using an Agilent Diode Array Detector. Confirmation of molecular formulae was accomplished using electrospray ionization in the positive mode with the Agilent Masshunter software (version B.02).

Examples

Example 1. Synthesis of Selected Compounds

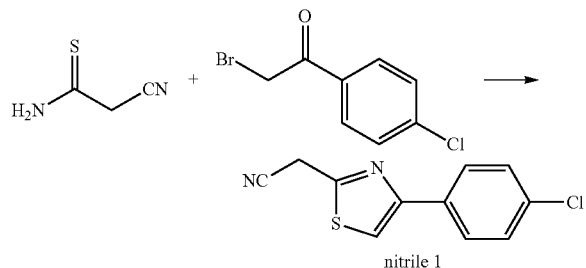

Method 1—Nitrile 1:

To a solution of 2-bromo-1-(4-chlorophenyl)ethanone (2.33 g, 10 mmol) in ethanol (25 mL) was added 2-cyanoethanethioamide (1 g, 10 mmol). The reaction mixture was heated at reflux for 15.5 h. The reaction mixture was cooled to 0° C. A precipitate formed and was removed by filtration washing with hexanes and subsequently drying under vacuum. The product, 2-(4-(4-chlorophenyl)thiazol-2-yl)acetonitrile (nitrile N1), is a brown powder; LCMS: m/z (M+H)$^+$=235.0; 1H NMR (400 MHz, CDCl$_3$) δ 7.88-7.77 (m, 2H), 7.48 (s, 1H), 7.44-7.35 (m, 2H), 4.17 (s, 2H).

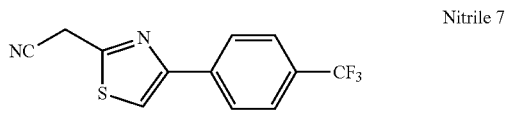

Nitrile 7

Nitrile 7: Synthesized by method 1 substituting 2-bromo-1-(4-trifluoromethylphenyl)ethanone as a starting material. Following the reaction the mixture was concentrated and purified via silica gel chromatography (0 to 40% EtOAc/hexanes); LCMS: m/z (M+H)$^+$=269.0.

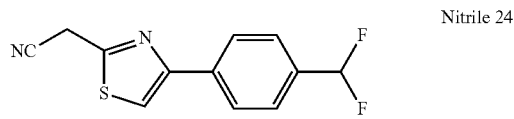 [SMILES: N#CCc1nc(-c2ccc(C(F)F)cc2)cs1]

Nitrile 24

Nitrile 24: Synthesized by method 1 substituting 2-bromo-1-(4-(difluoromethyl)phenyl)ethanone as a starting material; LCMS: m/z (M+H)$^+$=251.0.

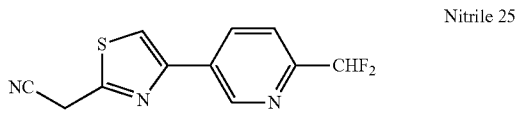 [SMILES: N#CCc1nc(-c2ccc(C(F)F)nc2)cs1]

Nitrile 25

Nitrile 25: Synthesized by method 1 substituting 2-bromo-1-(6-(difluoromethyl)pyridin-3-yl)ethanone as a starting material: LCMS: m/z (M+H)$^+$=252.0.

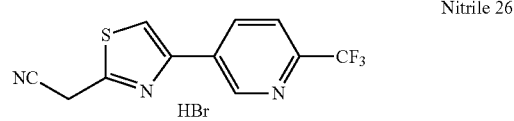 [SMILES: N#CCc1nc(-c2ccc(C(F)(F)F)nc2)cs1 ; Br]

Nitrile 26

Nitrile 26: Synthesized by method 1 substituting 2-bromo-1-(6-(trifluoromethyl)pyridin-3-yl)ethanone as a starting material: LCMS: m/z (M+H)$^+$=270.0.

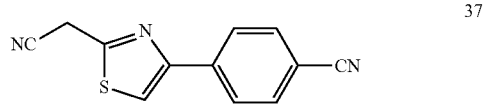

37

Nitrile 37: Synthesized by method 1 substituting 4-(2-bromoacetyl)benzonitrile as a starting material: LCMS: m/z (M+H)$^+$=226.0.

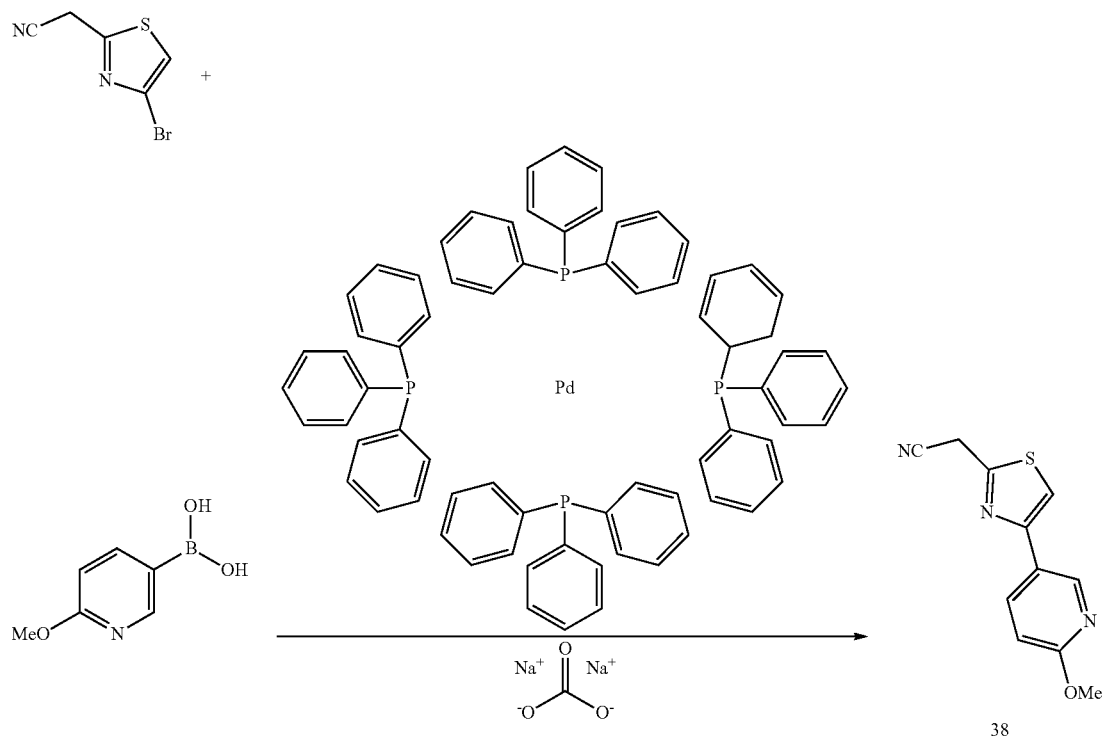

Nitrile 38: A mixture of 2-(4-bromothiazol-2-yl)acetonitrile (1.47 g, 7.24 mmol) and (6-methoxypyridin-3-yl)boronic acid (2.214 g, 14.48 mmol), in DMF (Volume: 20 ml) was treated with SODIUM CARBONATE (10.86 ml, 21.72 mmol) 2M solution and Pd(Ph$_3$P)$_4$ (0.418 g, 0.362 mmol). The mixture was heated in sealed tube at 125° C. for 4 h, cooled to rt, and then, filtered through celite with ethyl acetate. The concentrated filtrate was purified by chromatography (hexanes to 10:90 EA/Hex) to afford nitrile 38 in 90% yield (1.51 g): LCMS: m/z (M+H)$^+$=232.0.

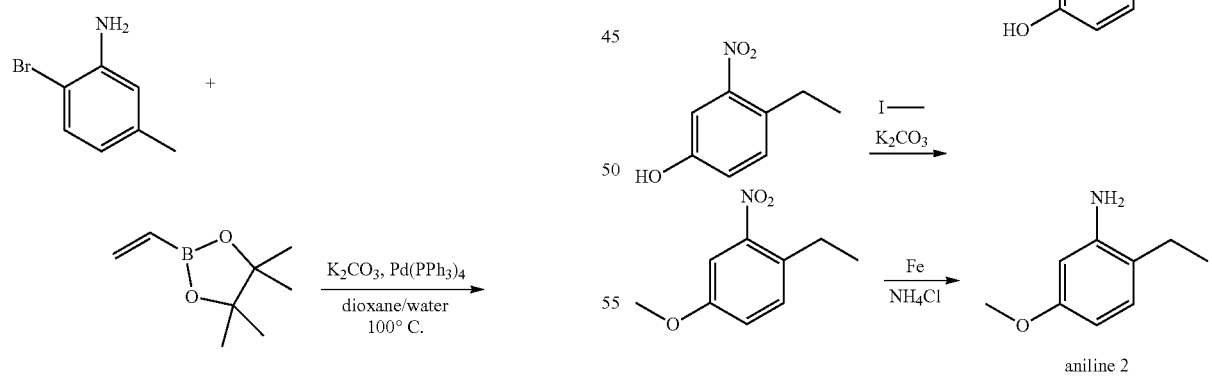

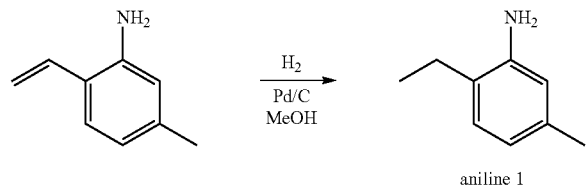

Aniline 2: Step 1: In a mixture of 5 ml. of 55% sulfuric acid and 4-ethyl-3-nitroaniline (1.2 g, 7.22 mmol) was suspended and then was diazotized with 2 ml of 20% sodium nitrite at 0° C. This diazonium salt solution then was added slowly to a boiling solution of 25 ml of 55% sulfuric acid. After the addition was completed the mixture was boiled for 30 min, cooled, and then was extracted with ether. The ether solution was washed with water, and then was extracted with dilute sodium hydroxide solution which on acidification yielded the phenol. This was extracted with ether, and the ether solution was dried over sodium sulfate and distilled.

Step 2: 4-ethyl-3-nitrophenol (460 mg, 2.75 mmol) was dissolved in acetone (25 ml), then K$_2$CO$_3$ (1141 mg, 8.26 mmol) and MeI (0.344 ml, 5.50 mmol) was added and reflux for 12 h and the solvent was concentrated and 4-methoxy-1-ethyl-2-nitrobenzene used next step without further purification.

Step 3: To a suspension of 4-methoxy-1-ethyl-2-nitrobenzene in THF (Volume: 10 ml) and Water (Volume: 3.33 ml) were added AMMONIUM CHLORIDE (294 mg, 5.50 mmol) followed by iron (768 mg, 13.76 mmol). The mixture was stirred at 80° C. overnight. After cooling, EtOAc was added and the reaction mixture was passed through Celite. The organic layer was dried and concentrated and purified by column chromatography to yield aniline 2 (20% over 3 steps).

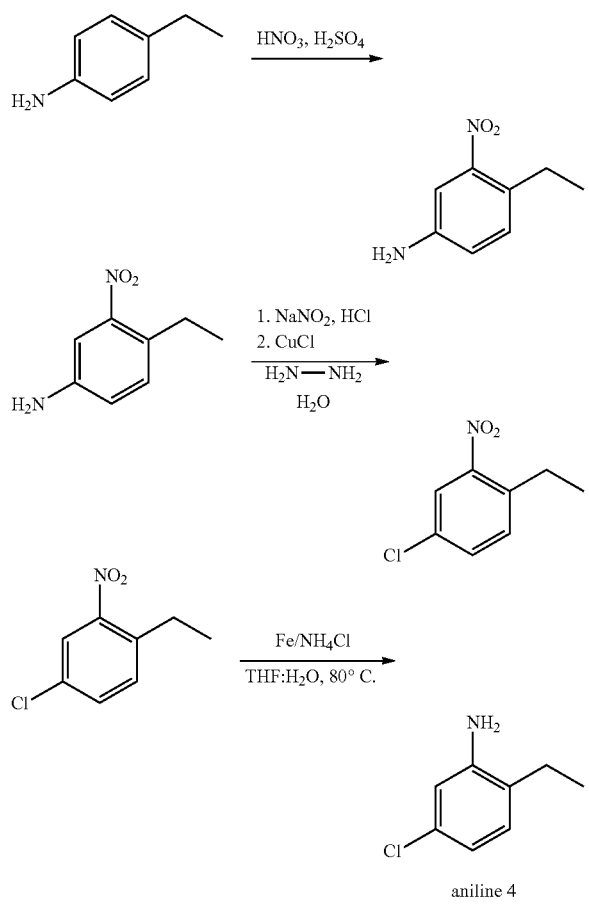

aniline 4

Aniline 4: Step 1: 4-ethylaniline (1.8 ml, 14.5 mmol) was added slowly to sulfuric acid (11 ml) at 0° C. The material clumped up and made a thick dark brown mixture. This was sonicated to get mostly into solution. To the mixture which was maintained at 0° C. was added nitric acid (0.7 ml) as well as additional sulfuric acid (1.75 ml). Reaction stirred 15 min and was sonicated to get the remainder of the material into solution. The mixture stirred at 0° C. 1 h and was subsequently poured onto ice and a brown precipitate was formed. The precipitate was removed by filtration and washed with a small amount of water. The solid was re-suspended and neutralized with ammonium hydroxide solution. The solid was filtered and dried. Some product was dissolved by the ammonium hydroxide and this layer was combined with the initial precipitate washings (which were acidic) following its basification with sodium hydroxide pellets. The solid was redissolved in this aqueous solution. The combined aqueous layers were extracted with DCM (4×), dried with magnesium sulfate (subsequent filtration), and concentrated to yield a brown oil, 4-ethyl-3-nitroaniline, which was used in the subsequent step without further purification (2.14 g, 89%); LCMS: m/z (M+H)$^+$=167.1.

Step 2: 4-Ethyl-3-nitroaniline (1 g, 6 mmol) was dissolved in concentrated HCl (20 ml). The compound initially solidified but most of material eventually was soluble. Cool mixture to 0° C. Add sodium nitrite (0.57 g, 8.3 mmol) in water (2.3 ml) and a gas was evolved. The mixture was sonicated to dissolve material further (**this should not be repeated as this material could be explosive!). Mixture was stirred at this temperature for 1 hr. Diazonium intermediate visible by (LCMS: m/z (M)$^+$=178.0). Copper (I) chloride (1 g, 10.5 mmol) was added to the mixture and a large amount of gas was evolved. Reaction mixture became dark green. Gas evolution ceased within 3 minutes but stirring was continued at rt for 1.5 h. The mixture was extracted with DCM (3×)/water, dried with magnesium sulfate (subsequent filtration), concentrated, and subsequently purified by silica gel chromatography (gradient 0 to 20% EtOAc/hexanes) to yield a light yellow oil, 4-chloro-1-ethyl-2-nitrobenzene (0.9 g, 81%).

Step 3: To a mixture of 4-chloro-1-ethyl-2-nitrobenzene (2 g, 10.78 mmol) in THF (15 mL) and water (5 mL) were added ammonia hydrochloride (1.729 g, 32.3 mmol) followed by iron (1.729 g, 32.3 mmol). The reaction mixture was heated at 80° C. for 12 h. The reaction mixture was cooled to room temperature, EtOAc was added and the reaction mixture was passed through Celite. The organic layer was washed with water and brine. The organic layer was dried and concentrated. The crude product was purified by column chromatography (10:90 EA/Hex to 100% EA) to afford the product, 5-chloro-2-ethylaniline, brown oil; LCMS: m/z (M+H)$^+$=156.0. Yield~90%; 1H NMR (400 MHz, DMSO-d6) δ 6.86 (dd, J=8.0, 0.7 Hz, 1H), 6.59 (d, J=2.2 Hz, 1H), 6.44 (dd, J=8.0, 2.2 Hz, 1H), 5.11 (s, 2H), 2.43-2.31 (m, 2H), 1.06 (t, J=7.5 Hz, 3H).

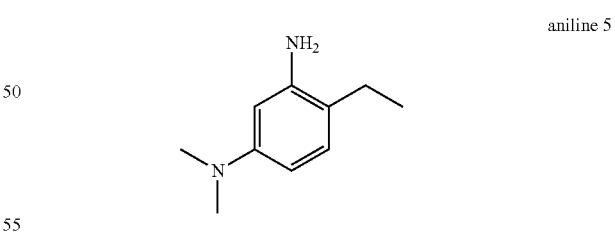

aniline 5

Aniline 5: Synthesized by the same method used to make aniline 2 substituting 4-ethyl-3-nitroaniline as a starting material in step 2 (90% yield over 2 steps).

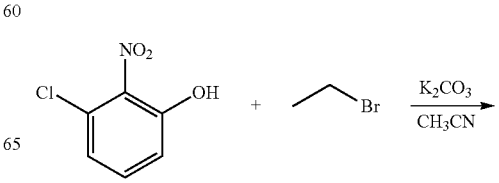

-continued

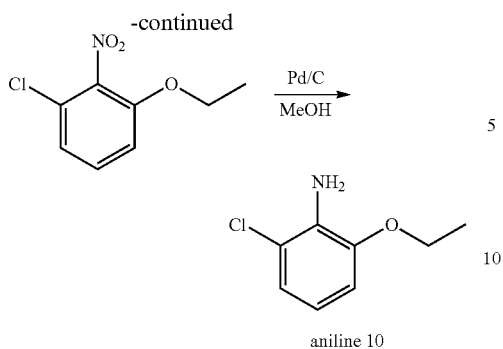

aniline 10

Aniline 10: Step 1: A mixture of 3-chloro-2-nitrophenol (173 mg, 1 mmol) and ethyl bromide (109 mg, 1.2 mmol) in acetonitrile (4:1, Volume: 2.5 ml) was treated with potassium carbonate (276 mg, 2 mmol). The mixture was stirred at rt for 2 h. The reaction was quenched with water and the aqueous layer was extracted with ethyl acetate. The organic layer was washed with brine, dried over Na$_2$SO$_4$, and concentrated. The crude product was purified by chromatography (hexanes to 10:90 EA/Hex) to afford the product.

Step 2: Same as step 2 in the synthesis of aniline 1 affording aniline 10 as an oil (15% over 2 steps).

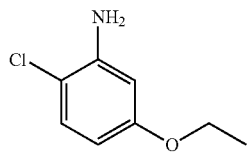

aniline 14

Aniline 14: Synthesized by the same method used to make aniline 10 substituting 4-chloro-3-nitrophenol as a starting material in step 1 (30% yield over 2 steps).

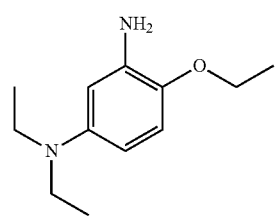

aniline 18

Aniline 18: Synthesized by the same method used to make aniline 10 substituting ethyl bromide as a starting material in step 1 (87% yield over 2 steps).

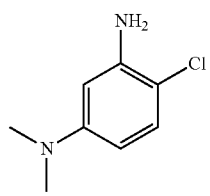

aniline 19

Aniline 19: Synthesized by the same method used to make aniline 2 substituting iodoethane as a starting material in step 1 (90% yield over 2 steps).

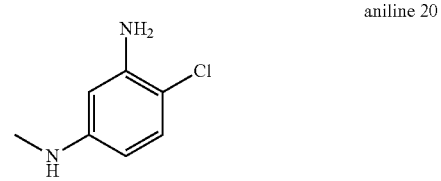

aniline 20

Aniline 20: Synthesized by the same method used to make aniline 2 substituting iodoethane as a starting material in step 1 (75% yield over 2 steps).

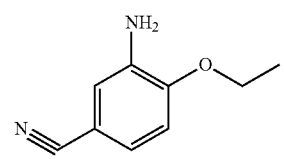

aniline 21

Aniline 21: Synthesized by the same method used to make aniline 10 substituting ethyl bromide as a starting material in step 1 (80% yield over 2 steps).

Method S

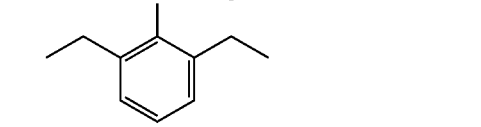

Method S-Compound 268:

Step 1: In a vial, methyl 3-oxobutanoate (0.385 mL, 3.57 mmol) and DMF-DMA (0.474 mL, 3.57 mmol) were mixed and heated neat at 100° C. for 15 min. The reaction mixture became a red oil.

Step 2: To the mixture was added i-PrOH (40 mL), 2-(4-(4-chlorophenyl)thiazol-2-yl)acetonitrile (837 mg, 3.57 mmol), and potassium tert-butoxide (400 mg, 3.57 mmol). The reaction was allowed to stir at rt for 2 h at which point the solvent was removed.

Step 3: To the resulting residue were added acetic acid (30 mL) and 2,6-dimethylaniline (646 μL, 3.9 mmol). The reaction stirred for 15 min and the mixture was diluted with water, extracted (EtOAc×2). The organic layers were combined (not dried with magnesium sulfate) and concentrated. The residue was taken up in DMF (40 mL) and heated at 125° C. for 1.5 h. The reaction mixture was diluted with water and EtOAc, extracted (2×), the organic layers were combined, dried with magnesium sulfate, concentrated and purified via silica gel chromatography (dry load) (0 to 25% EtOAc/hexanes) to afford methyl 5-(4-(4-chlorophenyl)thiazol-2-yl)-1-(2,6-diethylphenyl)-2-methyl-6-oxo-1,6-dihydropyridine-3-carboxylate (Compound 268, 1.05 g, 60%); LCMS: m/z (M+H)⁺=493.0.

Method U

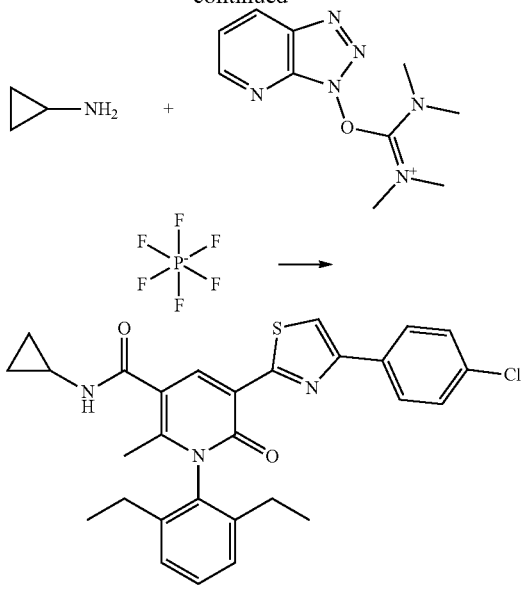

Method U-Compound 265:

To a mixture of 5-(4-(4-chlorophenyl)thiazol-2-yl)-1-(2,6-diethylphenyl)-2-methyl-6-oxo-1,6-dihydropyridine-3-carboxylic acid (40 mg, 0.084 mmol), cyclopropanamine (0.009 mL, 0.125 mmol) in DMF (1.3 mL) were added diisopropylethylamine (0.044 mL, 0.25 mmol) and HATU (38 mg, 0.10 mmol). The reaction mixture stirred at rt 2.25 h and was concentrated partially by a stream of air. The residue was taken up in DMSO and subsequently purified by reverse phase chromatography to give Compound 265:

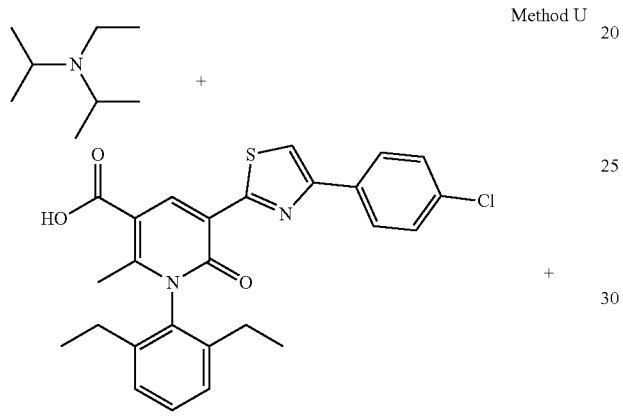

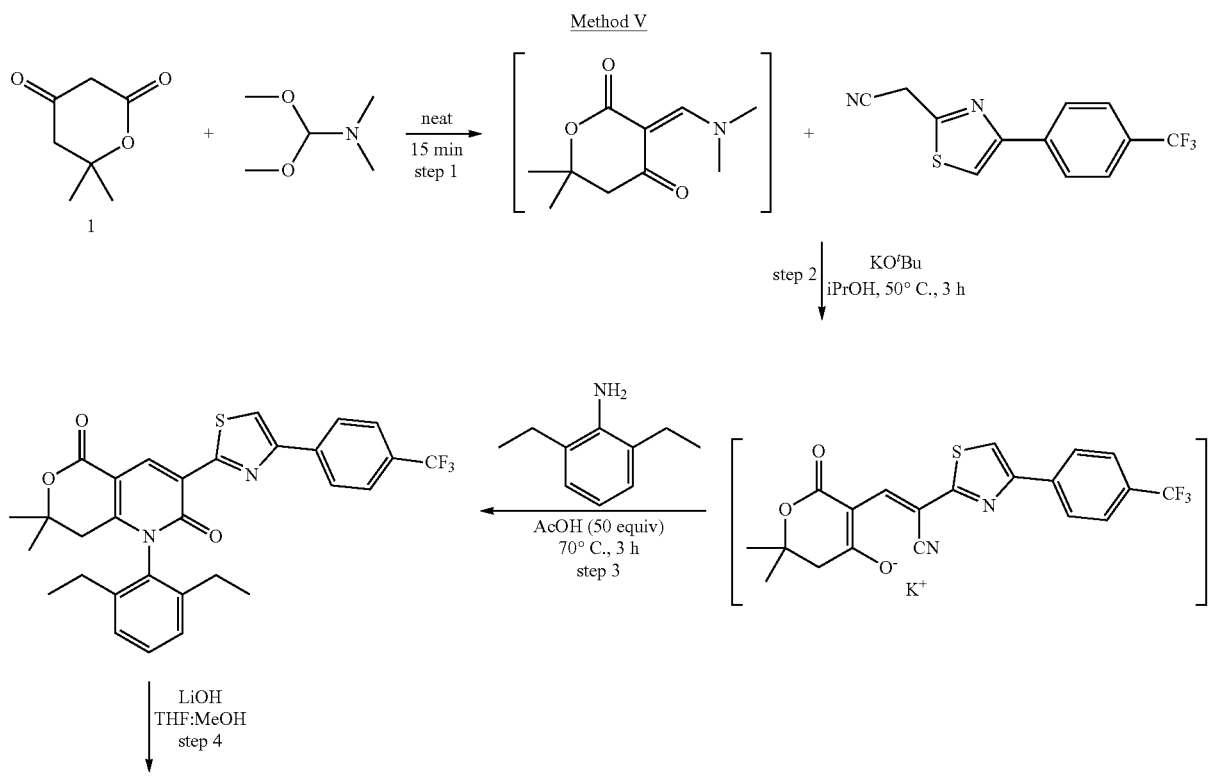

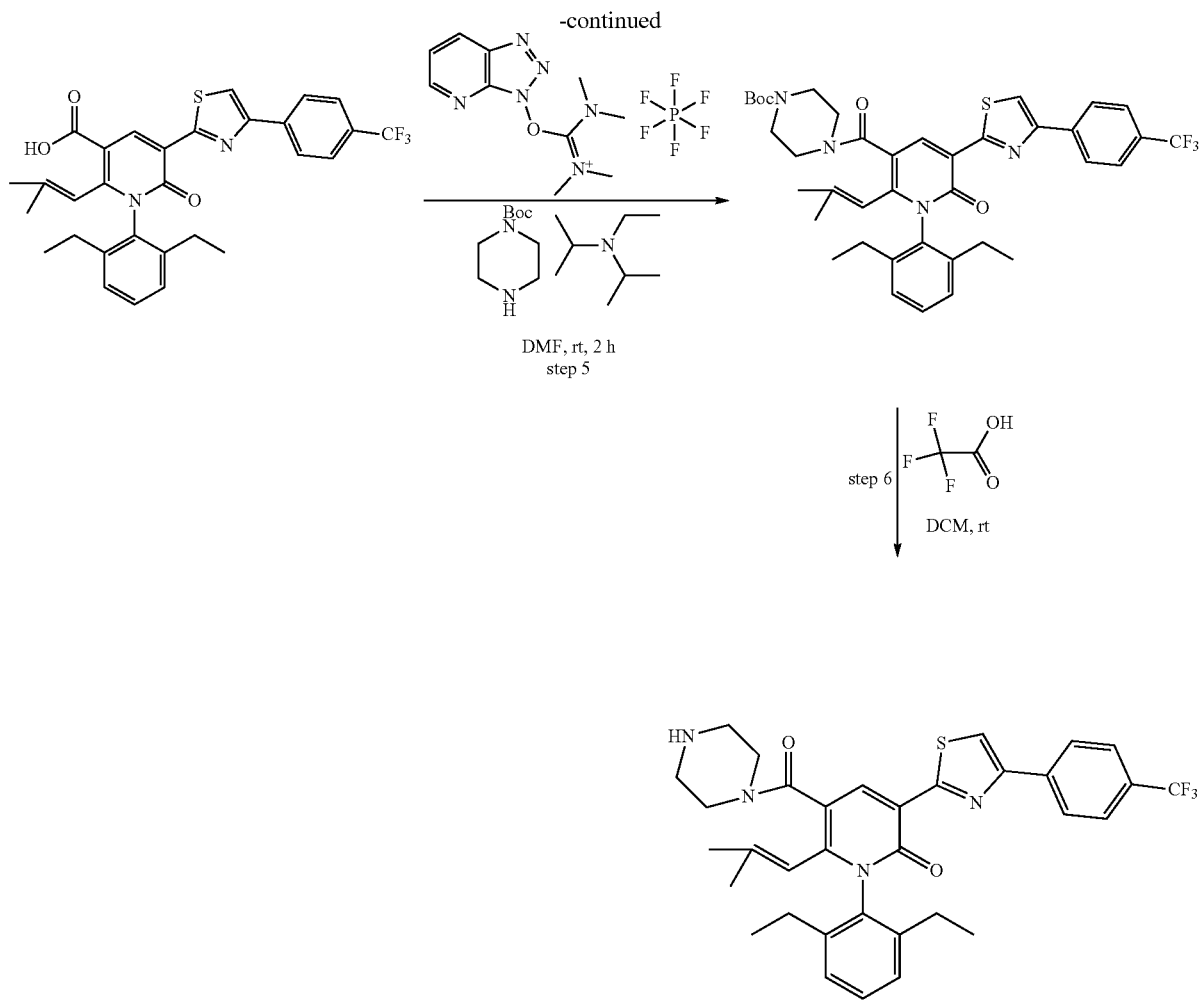

Method V-Compound 154:

Steps 1-3: The mixture of 6,6-dimethyldihydro-2H-pyran-2,4(3H)-dione (0.530 g, 3.73 mmol) and 1,1-dimethoxy-N,N-dimethylmethanamine (0.495 ml, 3.73 mmol) was stirred for 15 min at room temperature. To the mixture was diluted with IPA (Volume: 10 ml) and added 2-(2-(4-(trifluoromethyl)phenyl)thiazol-5-yl)acetonitrile (1.0 g, 3.73 mmol) and KtOBu (0.837 g, 7.46 mmol). The mixture was stirred at 50° C. for 3 hrs. The solvent was removed. To the residue was added 2,6-diethylaniline (0.665 ml, 4.10 mmol) and acetic acid (10.7 mL, 186 mmol). The mixture was stirred at 70° C. for 2 hrs and cooled to room temperature and diluted with EtOAc and washed with water. The organic layer was dried and concentrated and purified by column chromatography. The product, 1-(2,6-diethylphenyl) -7,7-dimethyl-3-(2-(4-(trifluoromethyl)phenyl)thiazol-4-yl)-7,8-dihydro-1H-pyrano[4,3-b]pyridine-2,5-dione; LCMS: m/z (M+H)$^+$=553.0.

Step 4: To a solution of 1-(2,6-diethylphenyl)-7,7-dimethyl-3-(2-(4-(trifluoromethyl)phenyl)thiazol-4-yl)-7,8-dihydro-1H-pyrano[4,3-b]pyridine-2,5-dione (1 g, 1.810 mmol) in THF (10 ml) and MeOH (10 ml) was added lithium hydroxide (0.303 g, 12.67 mmol) and the mixture became yellow. Stir 1 h at 70° C. Concentrate with a stream of air and dilute with DCM. Adjust pH of aqueous layer to pH 7 using 1N HCl, extract 2×25 mL DCM, dry organic layers over magnesium sulfate, and concentrate. The product, 1-(2,6-diethylphenyl)-2-(2-methylprop-1-en-1-yl)-6-oxo-5-(2-(4-(trifluoromethyl)phenyl)thiazol-4-yl)-1,6-dihydropyridine-3-carboxylic acid; LCMS: m/z (M+H)$^+$=553.0. The crude was used in the next step without further purification.

Steps 5 and 6: To a solution of 1-(2,6-diethylphenyl)-2-(2-methylprop-1-en-1-yl)-6-oxo-5-(4-(4-(trifluoromethyl)phenyl)thiazol-2-yl)-1,6-dihydropyridine-3-carboxylic acid (1.0 g, 1.810 mmol) in DMF (Volume: 5 ml) was added 2-(3H-[1,2,3]triazolo[4,5-b]pyridin-3-yl)-1,1,3,3-tetramethylisouronium hexafluorophosphate (V) (1.376 g, 3.62 mmol) and N-ethyl-N-isopropylpropan-2-amine (0.740 ml, 4.52 mmol) and tert-butyl piperazine-1-carboxylate (0.674 g, 3.62 mmol) mixture became yellow the reaction mixture was stirred for 2 hrs at rt and dilute with water and extract with 3×10 mL DCM, washed with brine. The organic layer was dried and concentrated. The crude was used in the next step without further purification. The crude was diluted with DCM (5 ml) and treated with 2,2,2-trifluoroacetic acid (1.4 mL, 18.10 mmol) and the reaction mixture was stirred for 3 hrs at rt. The solvent was concentrated and purified by column chromatography. The product, 1-(2,6-diethylphenyl)-6-(2-methylprop-1-en-1-yl)-5-(piperazine-1-carbonyl)-3-(4-(4-(trifluoromethyl)phenyl)thiazol-2-yl)pyridin-2(1H)-one, Compound 154; LCMS: m/z (M+H)$^+$=621.0.

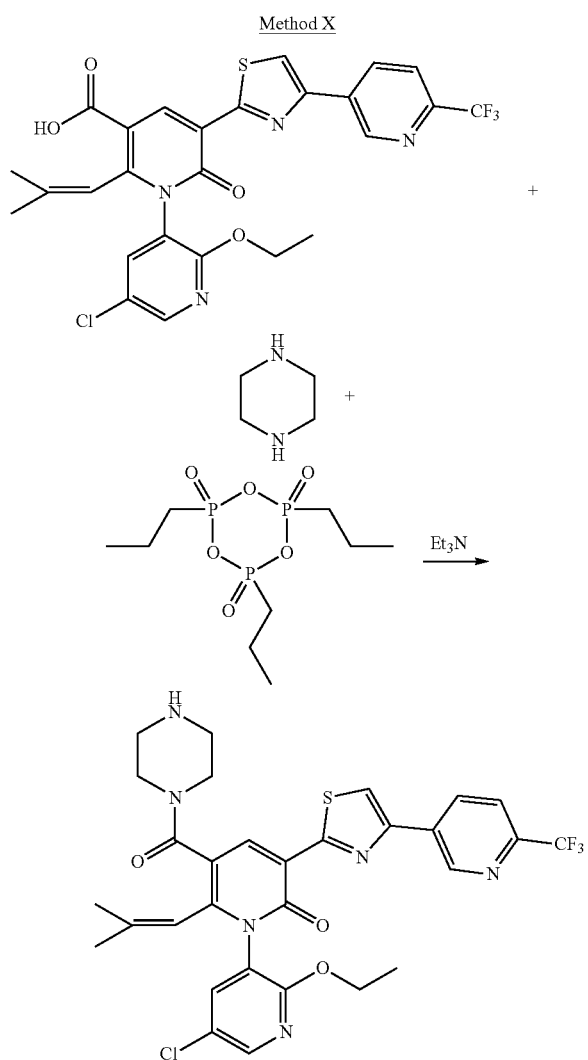

Example 2. Enzymatic Assays

Assays were conducted in a 1536-well black solid-bottom plate with a final assay volume of 9 μL. The depletion of the cofactor NADPH by the mutant IDH1 enzyme was coupled to a second enzyme diaphorase and its corresponding substrate resazurin.

Specifically, for IDH1 R132H, 3 μL of enzyme (4 mM β-ME, 0.0005 mg/mL IDH1 R132H, 150 mM NaCl, 20 mM Tris pH 7.5, 10 mM $MgCl_2$, 0.05% BSA) were added to the plate, followed by the addition of 23 nL of test compound in DMSO. The plate was lidded and incubated at room temperature for 30 minutes at which time 3 μL of substrate were added (0.016 mM NADPH, 2 mM α-KG, 150 mM NaCl, 20 mM Tris pH 7.5, 10 mM $MgCl_2$, 0.05% BSA). This reaction was incubated at room-temperature for 60 minutes at which time the detection mix was added (0.06 mg/mL diaphorase, 0.036 mM resazurin, 150 mM NaCl, 20 mM Tris pH 7.5, 10 mM $MgCl_2$, 0.05% BSA). After a 5-minute incubation, the fluorescence generated by the conversion of resazurin to resorufin was detected (ex 544 nm, emission 590 nm).

For IDH1 R132C, 3 μL of enzyme (0.00032 mg/mL IDH1 R132H, 10% glycerol, 50 mM potassium phosphate pH 6.5, 5 mM $MgCl_2$, 0.03% BSA) were added to the plate, followed by the addition of 23 nL of test compound in DMSO. The plate was lidded and incubated at room temperature for 30 minutes at which time 3 μL of substrate were added (0.012 mM NADPH, 0.6 mM α-KG, 10% glycerol, 50 mM potassium phosphate pH 6.5, 5 mM $MgCl_2$, 0.03% BSA). This reaction was incubated at room-temperature for 105 minutes at which time the detection mix was added (0.03 mg/mL diaphorase, 0.03 mM resazurin, 10% glycerol, 50 mM potassium phosphate pH 6.5, 5 mM $MgCl_2$, 0.03% BSA). After a 5-minute incubation, the fluorescence generated by the conversion of resazurin to resorufin was detected (ex 544 nm, emission 590 nm).

Example 3. Cell-Based Assays

Cell-based 2HG quantification assays were conducted in 96-well clear plates with a final assay volume of 100 μL. 2HG levels in cultured cells were determined using LC/MS-based detection.

Briefly, 4,000 cells/well (either transgenic U87 cells expressing mutant R132H IDH1, or HT1080 cells endogenously expressing the R132C mutant IDH1) were plated in 96-well clear tissue culture plates, and allowed to attached overnight at 37° C. The overlaying media was then removed and replaced with 100 μL fresh RPMI (10% FBS, no phenol red) containing titrations of compound, and incubated at 37° C. for 48 hours. Following incubation, 75 μL of the overlaying media was removed for 2HG analysis and snap-frozen on dry ice.

Samples were thawed, mixed with 2× volume of 100% acetonitrile, and centrifuged at 4,000 rpm for 15 minutes at 4° C. The resulting supernatant was collected to assess 2-hydroxyglutarate levels on a RF-MS system. The RF-MS system consists of RapidFire RF200 system (Agilent, Santa Clara, Calif.) interfaced with an API4000 mass spectrometer (AB Sciex, Foster City, Calif.). A Zymark Twister robotic arm is present to handle standard microtiter plates. The entire system is run with RapidFire software and Analyst software for the RF200 system and the mass spectrometer, respectively. The mobile phase consisted of 0.1% formic acid in 100% acetonitrile (solvent A) and 0.1% formic acid in water (solvent B). Samples were aspirated directly from 384-well plates into a 10 μL sample loop, and passed through an in-line purification SPE system with graphite carbon cartridges (Agilent) with solvent A at a flow rate of 1.5 mL/min for 1 s. After the de-salting step, analyte retained on the cartridge was eluted to the mass spectrometer with solvent B at a flow rate of 0.4 mL/min for 8 s. The cartridge was re-equilibrated with solvent A at a flow rate of 1.5 mL/min for 0.5 s. In total, the entire sampling cycle was 10 s per well. Each metabolite can be monitored by negative electrospray ionization on an API4000 triple-quadrupole mass spectrometer operating in multiple reaction monitoring (MRM) mode, with MS parameters optimized on infused metabolite standard solutions. Metabolites can be quantified by comparison of peak areas with pure metabolite standards at known concentration.

2HG metabolite levels were then determined and quantified using a 2HG standard curve, and % inhibition of 2HG was production was calculated using vehicle-treated and media-only controls.

Example 4. Additional Compounds

Table 1 shows compounds of Example 1 with biological and other data, and shows additional compounds prepared by the methods shown in Example 1. Hindered rotation as well as solvent peaks (DMSO and water) both complicate NMR signals and hide some proton resonances in many of the spectra. Table 2 shows further additional compounds which could be prepared by the methods shown in Example 1. Routine changes in starting materials and reaction conditions, readily apparent to those of one skilled in the art, were used to make the particular compounds disclosed in Table 1. An "A" is used to denote compounds with an $IC_{50}$ less than 0.3 micromolar, a "B" indicates compound with an $IC_{50}$ between 0.3 micromolar and 1.0 micromolar, a "C" denotes compounds with an $IC_{50}$ between 1.0 micromolar and 5.0 micromolar, a "D" denotes compounds with an $IC_{50}$ between 5.0 micromolar and 20 micromolar, and an "E" denotes compounds with an $IC_{50}$ greater than 20 micromolar. A standard enzymatic inhibition assay, such as the assay of Example 2, is used to determine the $IC_{50}$'s for the compounds.

TABLE 1

Characterization and Enzymatic Inhibition Data for Selected Compounds

| Cpd # | Structure | Data for R132H (µM) | Data for R132C (µM) | Synthesis Method | $^{1}$H-NMR | $[\alpha]_D^{20}$ (°) (C = 1, CH$_3$Cl$_3$) | ee (%) |
|---|---|---|---|---|---|---|---|
| 101 | 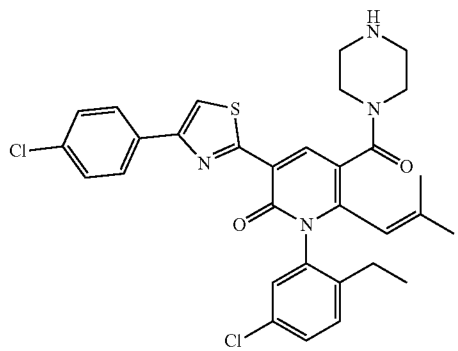 [SMILES: CCc1ccc(Cl)cc1-n1c(C=C(C)C)c(C(=O)N2CCNCC2)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), Aniline 4 (step 3); Methods: V | $^{1}$H NMR (400 MHz, DMSO-d$_6$) δ 8.60 (s, 1H), 8.21 (s, 1H), 8.09 (d, J = 8.2 Hz, 2H), 7.70-7.26 (m, 5H), 5.50-5.26 (m, 1H, rotameric), 3.67-3.55 (m, 1H), 3.41-3.11 (m, 3H), 2.78-2.53 (m, 4H), 2.37-2.02 (m, 2H), 1.57 (s, 3H), 1.55 (s, 3H), 1.15-0.91 (m,3H). | | |
| 102 | 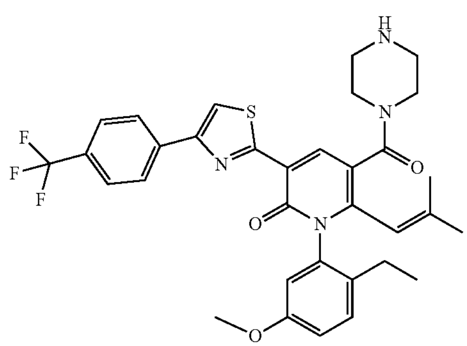 [SMILES: CCc1ccc(OC)cc1-n1c(C=C(C)C)c(C(=O)N2CCNCC2)cc(-c2nc(-c3ccc(C(F)(F)F)cc3)cs2)c1=O] | A | A | Starting materials: 6,6-dimethyl-dihydro-2H-pyran-2,4(3H)-dione (step 1), Nitrile 7 (step 2), Aniline 2 (step 3); Methods: V | $^{1}$H NMR (400 MHz, DMSO-d$_6$) δ 8.80 (bs, 1H), 8.70 (s, 1H), 8.40 (s, 1H), 8.28 (d, J = 7.9 Hz, 2H), 7.82 (d, J = 8.1 Hz, 2H), 7.39-6.70 (m, 3H), 5.57-5.31 (m, 1H, rotameric), 4.15-2.83 (m, 13H), 2.25-1.99 (m, 1H), 1.65-1.44 (m, 6H), 1.13-0.85 (m, 3H). | | |
| 103 | 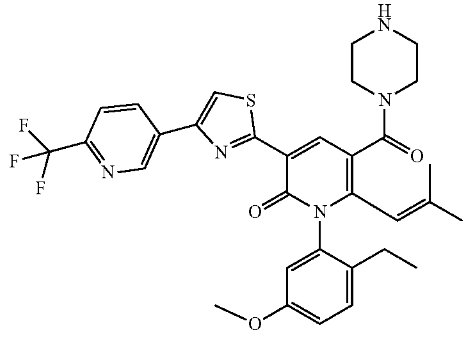 [SMILES: CCc1ccc(OC)cc1-n1c(C=C(C)C)c(C(=O)N2CCNCC2)cc(-c2nc(-c3ccc(C(F)(F)F)nc3)cs2)c1=O] | A | A | Starting materials: 6,6-dimethyl-dihydro-2H-pyran-2,4(3H)-dione (step 1), Nitrile 30 (step 2), Aniline 2 (step 3); Methods: V | $^{1}$H NMR (400 MHz, DMSO-d$_6$) δ 9.51-9.38 (m, 1H), 8.91-8.63 (m, 3H), 8.56 (s, 1H), 8.01 (d, J = 8.2 Hz, 1H), 7.37-6.70 (m, 3H), 5.56-5.34 (m, 1H, rotameric), 4.25-2.91 (m, 13H), 2.26-1.97 (m, 1H), 1.64-1.46 (m, 6H), 1.14-0.91 (m, 3H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 104 | 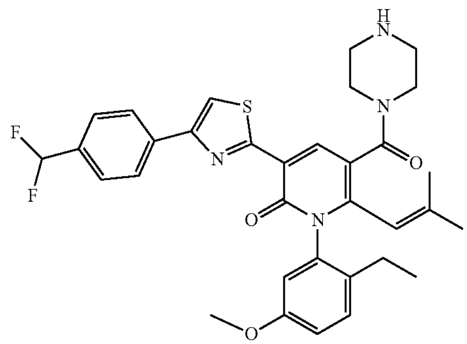 [SMILES: CCc1ccc(OC)cc1-n1c(C=C(C)C)c(C(=O)N2CCNCC2)cc(-c2nc(-c3ccc(C(F)F)cc3)cs2)c1=O] | A | A | Starting materials: 6,6-dimethyl-dihydro-2H-pyran-2,4(3H)-dione (step 1), Nitrile 24 (step 2), Aniline 2 (step 3); Methods: V | ¹H NMR (400 MHz, DMSO-d$_6$) δ 8.80 (s, 1H), 8.70 (s, 1H), 8.31 (s, 1H), 8.20 (d, J = 7.7 Hz, 2H), 7.66 (d, J = 8.0 Hz, 2H), 7.40-6.70 (m, 3H), 5.60-5.24 (m, 1H, rotameric), 4.29-2.82 (m, 13H), 2.31-1.98 (m, 1H), 1.67-1.43 (m, 6H), 1.18-0.85 (m, 3H). | | |
| 105 | 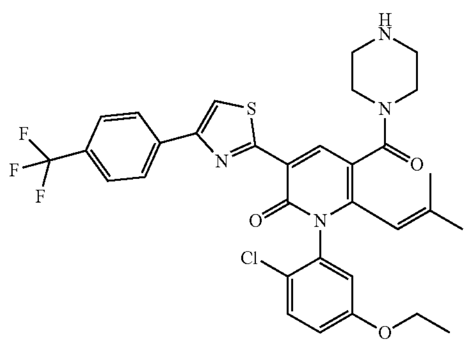 [SMILES: CCOc1ccc(Cl)c(-n2c(C=C(C)C)c(C(=O)N3CCNCC3)cc(-c3nc(-c4ccc(C(F)(F)F)cc4)cs3)c2=O)c1] | A | A | Starting materials: 6,6-dimethyl-dihydro-2H-pyran-2,4(3H)-dione (step 1), Nitrile 7 (step 2), Aniline 14 (step 3), Methods: V | ¹H NMR (400 MHz, DMSO-d$_6$) δ 8.63 (d, J = 0.4 Hz, 1H), 8.39 (s, 1H), 8.33-8.26 (m, 2H), 7.81 (dq, J = 7.6, 0.8 Hz, 2H), 7.54 (dd, J = 18.3, 8.9 Hz, 1H), 7.37 (d, J = 2.9 Hz, 1H), 7.16-7.03 (m, 1H), 5.46 (d, J = 31.4 Hz, 1H), 4.25-3.86 (m, 2H), 3.47 (d, J = 54.3 Hz, 1H), 3.22 (dd, J = 10.7, 5.5 Hz, 1H), 2.70 (s, 1H), 2.66-2.53 (m, 1H), 2.44-2.16 (m, 1H), 1.31 (dt, J = 20.2, 6.9 Hz, 3H). | | |
| 106 | 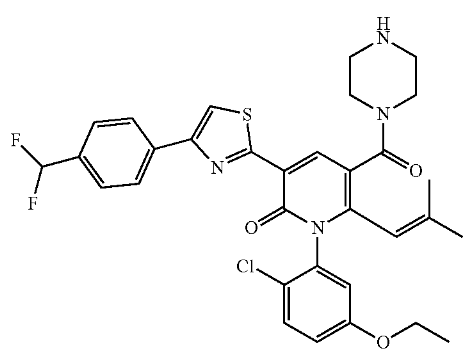 [SMILES: CCOc1ccc(Cl)c(-n2c(C=C(C)C)c(C(=O)N3CCNCC3)cc(-c3nc(-c4ccc(C(F)F)cc4)cs3)c2=O)c1] | A | A | Starting materials: 6,6-dimethyl-dihydro-2H-pyran-2,4(3H)-dione (step 1), Nitrile 24 (step 2), Aniline 14 (step 3); Methods: V | ¹H NMR (400 MHz, DMSO-d$_6$) δ 8.64 (s, 1H), 8.49 (s, 1H), 8.31 (d, J = 3.7 Hz, 2H), 8.21 (d, J = 8.0 Hz, 2H), 7.70-7.48 (m, 1H), 7.46-7.30 (m, 1H), 7.26-6.88 (m, 1H), 5.50 (s, 1H), 4.20-3.90 (m, 2H), 3.69-3.33 (m, 2H), 2.94-2.54 (m, 6H), 2.38-1.81 (m, 2H), 1.70-1.50 (m, 6H), 1.44-1.22 (m, 4H). | | |
| 107 | 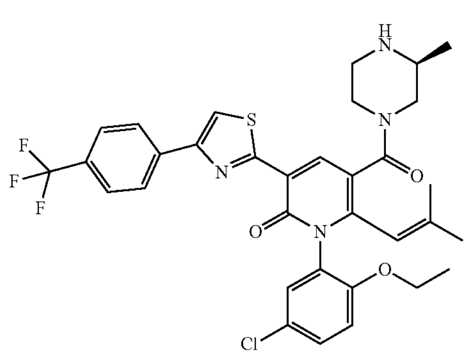 [SMILES: CCOc1ccc(Cl)cc1-n1c(C=C(C)C)c(C(=O)N2CCN[C@@H](C)C2)cc(-c2nc(-c3ccc(C(F)(F)F)cc3)cs2)c1=O] | A | A | Starting materials: 6,6-dimethyl-dihydro-2H-pyran-2,4(3H)-dione (step 1), Nitrile 7 (step 2), 5-chloro-2-ethoxyaniline (step 3); (S)-tert-butyl 2-methylpiperazine-1-carboxylate (step 5); Methods: V | ¹H NMR (400 MHz, Chloroform-d) δ 8.89-8.67 (m, 1H, rotameric), 8.11 (d, J = 8.0 Hz, 2H), 7.71-7.62 (m, 3H), 7.37 (dd, J = 9.0, 2.5 Hz, 1H), 7.24-7.06 (m, 1H), 7.00-6.86 (m, 1H), 5.47 (bs, 1H), 4.70-4.38 (m, 1H), 4.12-2.49 (m, 8H), 1.71-1.42 (m, 7H), 1.28-0.95 (m, 6H). | | |

TABLE 1-continued

Characterization and Enzymatic Inhibition Data for Selected Compounds

| Cpd # | Structure | Data for R132H (μM) | Data for R132C (μM) | Synthesis Method | $^1$H-NMR | $[\alpha]_D^{20}$ (°) (C = 1, CH$_3$Cl$_3$) | ee (%) |
|---|---|---|---|---|---|---|---|
| 108 | 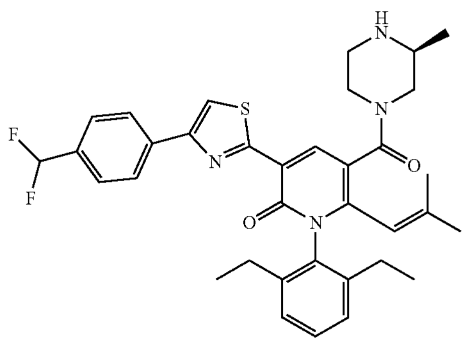 [SMILES: CCc1cccc(CC)c1-n1c(C=C(C)C)c(C(=O)N2CCN[C@@H](C)C2)cc(-c2nc(-c3ccc(C(F)F)cc3)cs2)c1=O] | A | A | Starting materials: 6,6-dimethyl-dihydro-2H-pyran-2,4(3H)-dione (step 1), Nitrile 24 (step 2),; (S)-tert-butyl 2-methylpiperazine-1-carboxylate (step 5); Methods: V | $^1$H NMR (400 MHz, DMSO-d$_6$) δ 8.66 (d, J = 1.9 Hz, 1H), 8.30 (d, J = 1.1 Hz, 1H), 8.21 (d, J = 8.0 Hz, 2H), 7.65 (d, J = 8.0 Hz, 2H), 7.41 (t, J = 7.8 Hz, 1H), 7.28 (dd, J = 19.4, 5.9 Hz, 2H), 5.26 (s, 1H), 3.40-3.29 (m, 2H), 2.35-2.20 (m, 2H), 2.18-1.99 (m, 2H), 1.61-1.51 (m, 6H), 1.19-1.04 (m, 6H), 0.98 (td, J = 7.4, 3.3 Hz, 6H), 0.84 (d, J = 6.0 Hz, 2H). | | |
| 109 | 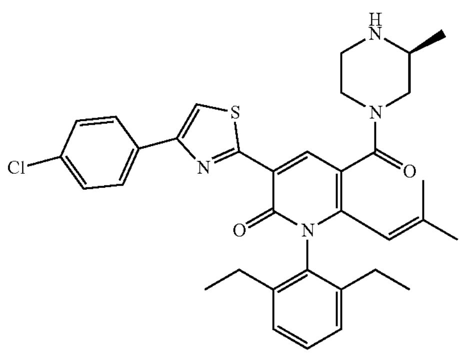 [SMILES: CCc1cccc(CC)c1-n1c(C=C(C)C)c(C(=O)N2CCN[C@@H](C)C2)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), (S)-tert-butyl 2-methylpiperazine-1-carboxylate (used in methods V, step 5); Methods: V | $^1$H NMR (400 MHz, DMSO-d$_6$) δ 8.73-8.53 (m, 1H), 8.22 (d, J = 1.0 Hz, 1H), 8.12-7.97 (m, 2H), 7.51 (d, J = 8.2 Hz, 2H), 7.45-7.33 (m, 1H), 7.29 (d, J = 18.4 Hz, 2H), 5.37-5.06 (m, 1H), 4.33 (dd, J = 24.9, 12.4 Hz, 0H), 4.18 (d, J = 10.0 Hz, 0H), 3.29 (s, 14H), 3.05-2.69 (m, 1H), 2.69-2.53 (m, 1H), 2.43-2.20 (m, 3H), 2.09 (td, J = 18.0, 15.3, 8.8 Hz, 2H), 1.66-1.42 (m, 4H), 1.21-1.04 (m, 3H), 0.99 (dt, J = 10.4, 5.1 Hz, 4H), 0.84 (d, J = 5.9 Hz, 2H). | | |
| 110 | 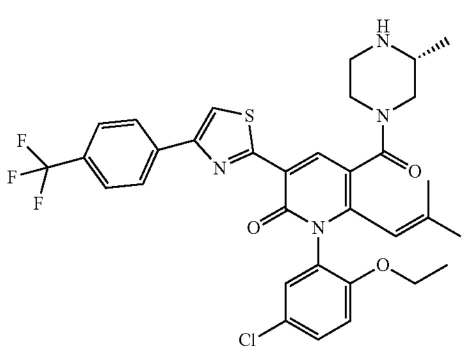 [SMILES: CCOc1ccc(Cl)cc1-n1c(C=C(C)C)c(C(=O)N2CCN[C@H](C)C2)cc(-c2nc(-c3ccc(C(F)(F)F)cc3)cs2)c1=O] | A | A | Starting materials: 6,6-dimethyl-dihydro-2H-pyran-2,4(3H)-dione (step 1), Nitrile 7 (step 2), 5-chloro-2-ethoxyaniline (step 3); (R)-tert-butyl 2-methylpiperazine-1-carboxylate (step 5); Methods: V | $^1$H NMR (400 MHz, Chloroform-d) δ 8.89-8.68 (m, 1H, rotameric), 8.11 (d, J = 8.0 Hz, 2H), 7.74-7.64 (m, 3H), 7.37 (dd, J = 9.0, 2.5 Hz, 1H), 7.23-7.04 (m, 1H), 7.01-6.88 (m, 1H), 5.48 (bs, 1H), 4.71-4.41 (m, 1H), 4.14-2.41 (m, 8H), 1.72-1.43 (m, 7H), 1.29-0.98 (m, 6H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 111 | 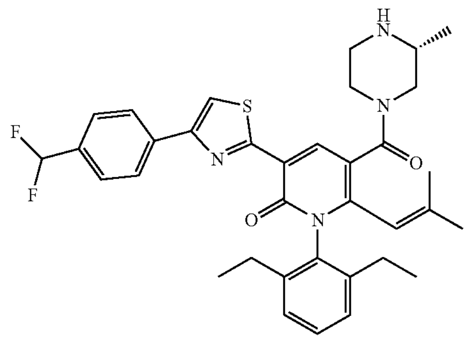 [SMILES: CCc1cccc(CC)c1-n1c(C=C(C)C)c(C(=O)N2CCN[C@H](C)C2)cc(-c2nc(-c3ccc(C(F)F)cc3)cs2)c1=O] | A | A | Starting materials: 6,6-dimethyl-dihydro-2H-pyran-2,4(3H)-dione (step 1), Nitrile 24 (step 2), (R)-tert-butyl 2-methylpiperazine-1-carboxylate (used in methods V, step 5); Methods: V | ¹H NMR (400 MHz, DMSO-d$_6$) δ 8.66 (d, J = 1.9 Hz, 1H), 8.30 (d, J = 1.1 Hz, 1H), 8.21 (d, J = 8.0 Hz, 2H), 7.70-7.60 (m, 2H), 7.41 (t, J = 8.0 Hz, 1H), 7.28 (dt, J = 19.2, 4.1 Hz, 1H), 7.07 (t, J = 56.0 Hz, 1H), 5.26 (s, 1H), 4.43-4.12 (m, 2H), 3.49-3.34 (m, 2H), 3.05-2.71 (m, 2H), 2.69-2.53 (m, 2H), 2.39-2.19 (m, 2H), 2.19-1.98 (m, 2H), 1.62-1.49 (m, 6H), 1.24-1.02 (m, 3H), 0.98 (dp, J = 7.5, 3.5 Hz, 5H), 0.89-0.76 (m, 2H). | | |
| 112 | 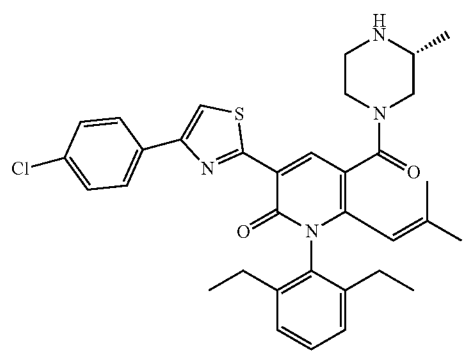 [SMILES: CCc1cccc(CC)c1-n1c(C=C(C)C)c(C(=O)N2CCN[C@H](C)C2)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), (R)-tert-butyl 2-methylpiperazine-1-carboxylate (used in methods V, step 5); Methods: V | ¹H NMR (400 MHz, DMSO-d$_6$) δ 8.78-8.55 (m, 1H), 8.22 (d, J = 1.0 Hz, 1H), 8.16-7.99 (m, 2H), 7.51 (d, J = 8.2 Hz, 2H), 7.47-7.36 (m, 1H), 7.29 (d, J = 17.9 Hz, 2H), 5.34-5.03 (m, 1H), 4.33 (dd, J = 24.9, 12.1 Hz, 1H), 4.17 (d, J = 13.1 Hz, 0H), 3.29 (s, 8H), 3.07-2.52 (m, 3H), 2.41-2.22 (m, 3H), 2.11 (ddp, J = 22.6, 14.9, 7.9, 7.2 Hz, 2H), 1.65-1.43 (m, 6H), 1.18-1.04 (m, 3H), 0.99 (dt, J = 10.6, 5.1 Hz, 4H), 0.84 (d, J = 5.9 Hz, 2H). | | |
| 113 | 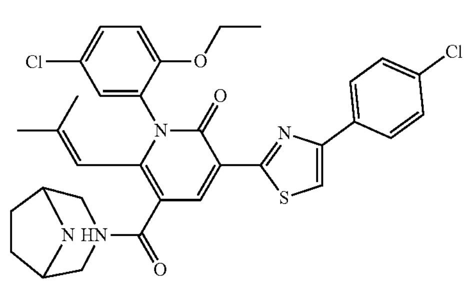 [SMILES: CCOc1ccc(Cl)cc1-n1c(C=C(C)C)c(C(=O)N2CC3CCC(C2)N3)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), 5-chloro-2-ethoxyaniline (step 3), (1R,5S)-tert-butyl 3,8-diazabicyclo[3.2.1]octane-8-carboxylate (step 5); Methods: V | ¹H NMR (400 MHz, Chloroform-d) δ 8.78 (s, 1H), 8.77-8.30 (dd, 1H, rotameric), 7.94 (d, J = 8.5 Hz, 2H), 7.56 (s, 1H), 7.47-7.30 (m, 3H), 7.18 (s, 1H), 6.93 (d, J = 8.3 Hz, 1H), 5.49 (s, 1H), 4.57-2.71 (m, 9H), 1.95-1.73 (m, 4H), 1.62 (s, 6H), 1.30-1.09 (m,3H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 113-1 | 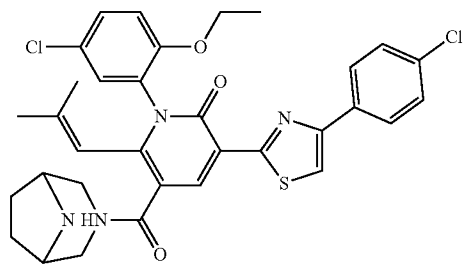 [SMILES: CCOc1ccc(Cl)cc1-n1c(C=C(C)C)c(C(=O)N2CC3CCC(C2)N3)cc(-c2nc(-c3ccc(Cl)cc3)cs2)c1=O] | A | A | Chiral separation of 113: ChiralPak IA (5 × 50 cm, 20 um); Hex/EtOH/DEA (40:60:0.04); 35 mL/min | ¹H NMR (400 MHz, Chloroform-d) δ 8.89-8.58 (m, 1H, rotameric), 7.95 (d, J = 8.2 Hz, 2H), 7.58 (s, 1H), 7.42 (d, J = 8.6 Hz, 2H), 7.37 (dd, J = 8.9, 2.5 Hz, 1H), 7.24-7.02 (m, 1H), 7.02-6.81 (m, 1H), 5.52-5.38 (m, 1H, rotameric), 4.68-2.82 (m, 7H), 2.12-1.47 (m, 12H), 1.28-0.77 (m, 3H). | −1.7 | >98 |
| 113-2 | 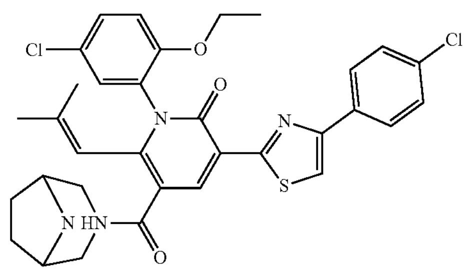 [SMILES: CCOc1ccc(Cl)cc1-n1c(C=C(C)C)c(C(=O)N2CC3CCC(C2)N3)cc(-c2nc(-c3ccc(Cl)cc3)cs2)c1=O] | C | B | Chiral separation of 113: ChiralPak IA (5 × 50 cm, 20 um); Hex/EtOH/DEA (40:60:0.04); 35 mL/min | ¹H NMR (400 MHz, Chloroform-d) δ 8.88-8.57 (m, 1H, rotameric), 7.94 (d, J = 8.2 Hz, 2H), 7.58 (s, 1H), 7.40 (d, J = 8.6 Hz, 2H), 7.35 (dd, J = 8.9, 2.5 Hz, 1H), 7.22-7.03 (m, 1H), 7.02-6.80 (m, 1H), 5.54-5.37 (m, 1H, rotameric), 4.69-2.84 (m, 7H), 2.14-1.46 (m, 12H), 1.28-0.79 (m, 3H). | +1.8 | 96.5 |
| 114 | 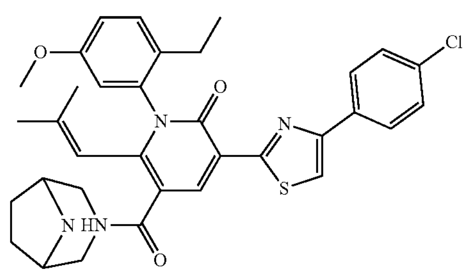 | A | A | Starting materials: 6,6-dimethyl-dihydro-2H-pyran-2,4(3H)-dione (step 1), Nitrile 1 (step 2), aniline 2 (Step 3), (1R,5S)-tert-butyl 3,8-diazabicyclo[3.2.1]octane-8-carboxylate (step 5); Methods: V | ¹H NMR (400 MHz, DMSO-d$_6$) δ 8.68 (s, 1H), 8.23 (s, 1H), 8.09 (dd, J = 8.5, 1.6 Hz, 3H), 7.61-7.45 (m, 2H), 7.31 (d, J = 9.0 Hz, 1H), 7.03 (d, J = 7.6 Hz, 1H), 5.47 (s, 1H), 4.43 (t, J = 16.8 Hz, 1H), 4.17-3.80 (m, 4H), 3.04-2.89 (m, 1H), 2.17-1.70 (m, 6H), 1.56 (dd, J = 21.7, 13.9 Hz, 8H), 1.16-0.86 (m, 4H). | | |
| 114-1 | 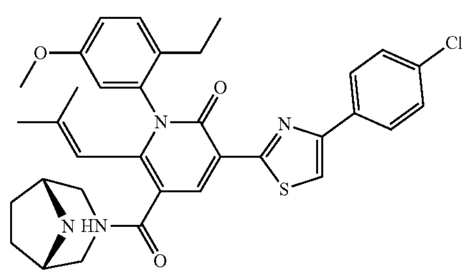 [SMILES: CCc1ccc(OC)cc1-n1c(C=C(C)C)c(C(=O)N2C[C@H]3CC[C@@H](C2)N3)cc(-c2nc(-c3ccc(Cl)cc3)cs2)c1=O] | A | A | 1st eluting-Chiral separation-Column: CHIRALPAK IA Mobile Phase: Hex/EtOH/DEA 40:60:0.04 Flow rate: 40 mL/min | ¹H NMR (400 MHz, Chloroform-d) δ 8.86 (d, J = 15.1 Hz, 1H), 7.96 (d, J = 7.8 Hz, 2H), 7.57 (s, 1H), 7.45-7.37 (m, 2H), 7.33-7.27 (m, 1H), 7.01-6.93 (m, 1H), 6.58 (d, J = 79.1 Hz, 1H), 5.60-5.30 (m, 1H), 4.47 (dd, J = 22.7, 12.9 Hz, 1H), 3.83 (s, 2H), 3.74 (s, 1H), 3.62 (s, 2H), 3.47 (s, 1H), 3.32 (d, J = 22.8 Hz, 3H), 2.83 (s, 1H), 2.50-2.07 | −2.7 | 93.6 |

TABLE 1-continued

Characterization and Enzymatic Inhibition Data for Selected Compounds

| Cpd # | Structure | Data for R132H (μM) | Data for R132C (μM) | Synthesis Method | $^1$H-NMR | $[\alpha]_D^{20}$ (°) (C = 1, CH$_3$Cl$_3$) | ee (%) |
|---|---|---|---|---|---|---|---|
| | | | | | (m, 3H), 1.97 (s, 1H), 1.81 (s, 2H), 1.74 (s, 2H), 1.67-1.54 (m, 23H), 1.16 (t, J = 7.4 Hz, 2H), 1.04 (t, J = 7.7 Hz, 2H). | | |
| 114-2 | 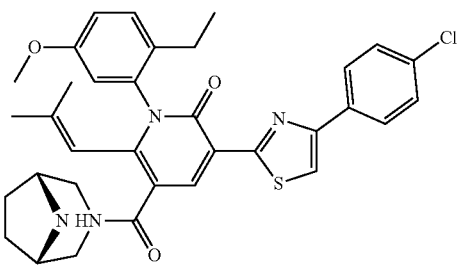 | B | B | 2nd-eluting-Chiral separation-Column: CHIRALPAK IA Mobile Phase: Hex/EtOH/DEA 40:60:0.04 Flow rate: 40 mL/min | $^1$H NMR (400 MHz, Chloroform-d) δ 8.86 (d, J = 15.1 Hz, 1H), 7.96 (d, J = 8.1 Hz, 2H), 7.57 (s, 1H), 7.45-7.37 (m, 2H), 7.29-7.19 (m, 1H), 6.97 (dd, J = 8.4, 2.3 Hz, 1H), 6.72-6.45 (m, 1H), 5.62-5.29 (m, 1H), 4.47 (dd, J = 22.3, 12.8 Hz, 1H), 3.83 (s, 1H), 3.74 (s, 1H), 3.61 (s, 1H), 3.46 (s, 1H), 3.42-3.21 (m, 2H), 2.82 (t, J = 11.4 Hz, 1H), 2.42-2.07 (m, 1H), 1.97 (d, J = 9.6 Hz, 1H), 1.80 (s, 2H), 1.72 (d, J = 17.3 Hz, 2H), 1.58 (s, 7H), 1.16 (t, J = 7.5 Hz, 1.3H), 1.04 (t, J = 7.7 Hz, 1.6H). | +2.5 | >99% |
| 115 | 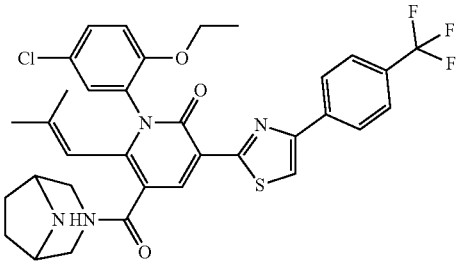 [SMILES: CCOc1ccc(Cl)cc1-n1c(C=C(C)C)c(C(=O)N2CC3CCC(C2)N3)cc(-c2nc(-c3ccc(C(F)(F)F)cc3)cs2)c1=O] | A | A | Starting materials: 6,6-dimethyl-dihydro-2H-pyran-2,4(3H)-dione (step 1), Nitrile 7 (step 2), 5-chloro-2-ethoxyaniline (step 3); (1R,5S)-tert-butyl 3,8-diazabicyclo[3.2.1]octane-8-carboxylate (step 5); Methods: V | $^1$H NMR (400 MHz, Chloroform-d) δ 8.84 (bs, 1H), 8.12 (d, J = 8.1 Hz, 2H), 7.74-7.64 (m, 3H), 7.36 (dd, J = 8.9, 2.6 Hz, 1H), 7.01-6.91 (m, 1H), 5.47 (bs, 1H), 4.55-4.40 (m, 1H), 4.10-3.81 (m, 2H), 3.64-2.75 (m, 6H), 1.99-1.90 (m, 1H), 1.85-1.67 (m, 3H), 1.60 (s, 6H), 1.24 (t, J = 7.0 Hz, 3H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 116 | 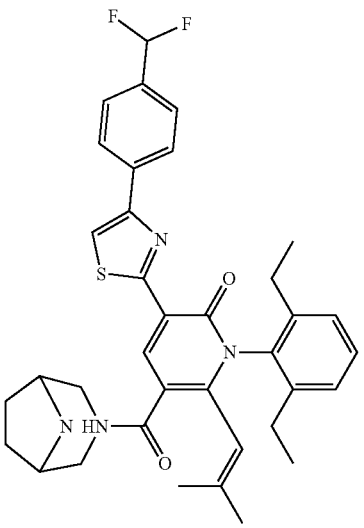 [SMILES: CCc1cccc(CC)c1-n1c(C=C(C)C)c(C(=O)N2CC3CCC(C2)N3)cc(-c2nc(-c3ccc(C(F)F)cc3)cs2)c1=O] | A | A | Starting materials: 6,6-dimethyl-dihydro-2H-pyran-2,4(3H)-dione (step 1), Nitrile 24 (step 2), (1R,5S)-tert-butyl 3,8-diazabicyclo[3.2.1]octane-8-carboxylate (used in methods V, step 5); Methods: V | | | |
| 117 | 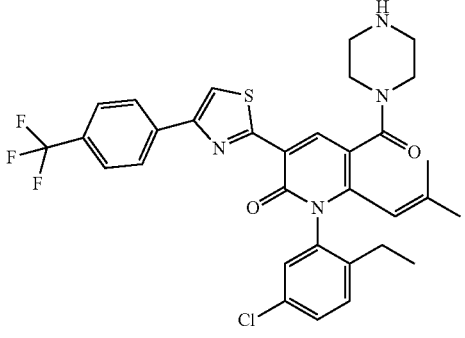 [SMILES: CCc1ccc(Cl)cc1-n1c(C=C(C)C)c(C(=O)N2CCNCC2)cc(-c2nc(-c3ccc(C(F)(F)F)cc3)cs2)c1=O] | A | A | Starting materials: methyl 5-methyl-3-oxohexanoate (step 1), Nitrile 7 (step 2), aniline 4 (step 3), piperazine (used in method V); Methods: S, ester hydrolyzed with LiOH (xs), THF/MeOH/water, 60° C.; U | | | |
| 118 | 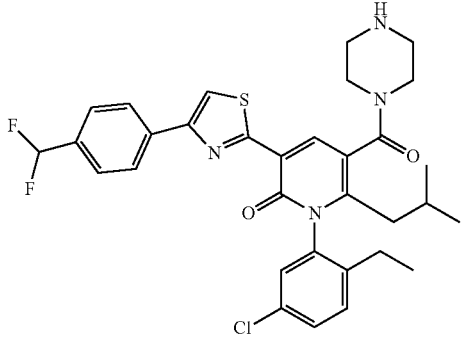 [SMILES: CCc1ccc(Cl)cc1-n1c(CC(C)C)c(C(=O)N2CCNCC2)cc(-c2nc(-c3ccc(C(F)F)cc3)cs2)c1=O] | B | B | Starting materials: methyl 5-methyl-3-oxohexanoate (step 1), Nitrile 24 (step 2), aniline 4 (step 3), piperazine (used in method V); Methods: S, ester hydrolyzed with LiOH (xs), THF/MeOH/water, 60° C.; U | | | |

TABLE 1-continued

Characterization and Enzymatic Inhibition Data for Selected Compounds

| Cpd # | Structure | Data for R132H (µM) | Data for R132C (µM) | Synthesis Method | $^1$H-NMR | $[\alpha]_D^{20}$ (°) (C = 1, CH$_3$Cl$_3$) | ee (%) |
|---|---|---|---|---|---|---|---|
| 119 | 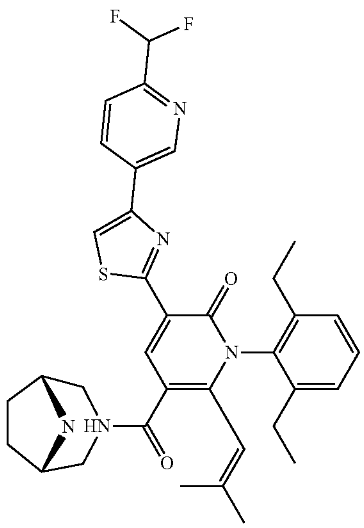 [SMILES: CCc1cccc(CC)c1-n1c(C=C(C)C)c(C(=O)N2C[C@H]3CC[C@@H](C2)N3)cc(-c2nc(-c3ccc(C(F)F)nc3)cs2)c1=O] | A | A | Starting materials: 6,6-dimethyl-dihydro-2H-pyran-2,4(3H)-dione (step 1), Nitrile 25 (step 2), (1R,5S)-tert-butyl 3,8-diazabicyclo[3.2.1]octane-8-carboxylate (used in methods V, step 5); Methods: V | $^1$H NMR (400 MHz, DMSO-d$_6$) δ 9.36 (d, J = 2.2 Hz, 1H), 8.70 (s, 1H), 8.62 (dd, J = 8.0, 2.4 Hz, 2H), 8.47 (s, 1H), 7.81 (d, J = 8.1 Hz, 1H), 7.41 (t, J = 7.7 Hz, 1H), 7.35-7.20 (m, 3H), 7.15 (s, 0H), 7.01 (s, 1H), 6.87 (s, 0H), 5.24 (s, 1H), 4.20 (d, J = 12.4 Hz, 1H), 3.78 (d, J= 12.7 Hz, 0H), 3.39 (s, 2H), 3.30 (s, 5H), 3.18 (d, J = 12.3 Hz, 1H), 3.06 (d, = 11.6 Hz, 1H), 2.91 (d, J = 12.9 Hz, 0H), 2.70-2.54 (m, 1H), 2.44-2.21 (m, 2H), 2.08 (qp, J = 14.9, 7.5 Hz, 1H), 1.73-1.39 (m, 11H), 1.19-1.02 (m, 4H), 0.99 (dt, J = 10.5, 7.6 Hz, 4H). | | |
| 120 | 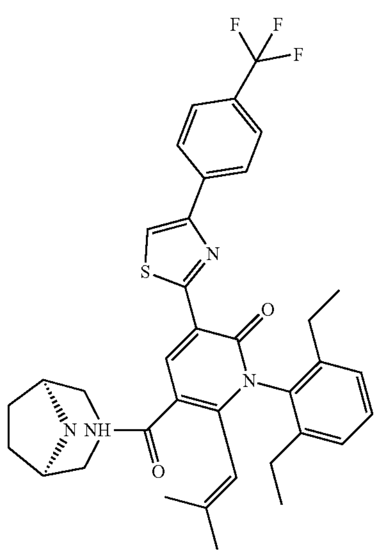 [SMILES: CCc1cccc(CC)c1-n1c(C=C(C)C)c(C(=O)N2C[C@H]3CC[C@@H](C2)N3)cc(-c2nc(-c3ccc(C(F)(F)F)cc3)cs2)c1=O] | A | A | Starting materials: 6,6-dimethyl-dihydro-2H-pyran-2,4(3H)-dione (step 1), Nitrile (step 2), (1R,5S)-tert-butyl 3,8-diazabicyclo[3.2.1]octane-3-carboxylate (used in methods V, step 5); Methods: V; Methods: V | $^1$H NMR (400 MHz, DMSO-d$_6$) δ 8.82-8.75 (m, 1H), 8.43 (s, 1H), 8.32 (d, J = 8.1 Hz, 2H), 7.85 (d, J = 8.1 Hz, 2H), 7.44 (t, J = 7.6 Hz, 1H), 7.31 (t, J = 9.4 Hz, 2H), 5.24 (s, 1H), 4.37 (s, 1H), 3.66 (d, J = 5.2 Hz, 1H), 2.93-2.87 (m, 1H), 2.70-2.59 (m, 2H), 2.32-2.03 (m, 4H), 1.81 (q, J = 7.9, 6.8 Hz, 2H), 1.75-1.67 (m, 3H), 1.57 (d, J = 16.9 Hz, 6H), 1.07 (d, J = 34.7 Hz, 7H). | | |

TABLE 1-continued

Characterization and Enzymatic Inhibition Data for Selected Compounds

| Cpd # | Structure | Data for R132H (µM) | Data for R132C (µM) | Synthesis Method | $^1$H-NMR | $[\alpha]_D^{20}$ (°) (C = 1, CH$_3$Cl$_3$) | ee (%) |
|---|---|---|---|---|---|---|---|
| 121 | 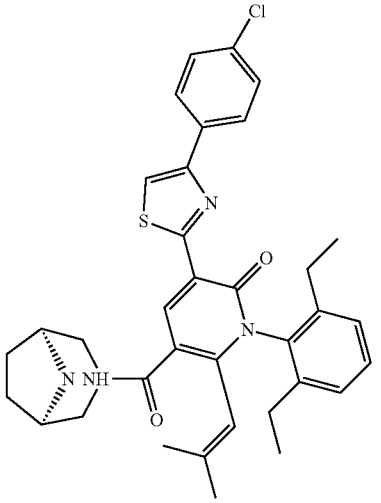 [SMILES: CCc1cccc(CC)c1-n1c(C=C(C)C)c(C(=O)N2C[C@H]3CC[C@@H](C2)N3)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), (1R, 5S)-tert-butyl 3,8-diazabicyclo[3.2.1]octane-3-carboxylate (used in methods V, step 5); Methods: V, Methods: V | $^1$H NMR (400 MHz, DMSO-d$_6$) δ 8.75 (s, 1H), 8.26 (s, 1H), 8.12 (d, J = 8.0 Hz, 2H), 7.54 (d, J = 8.2 Hz, 2H), 7.43 (t, J = 7.6 Hz, 1H), 7.30 (t, J = 9.2 Hz, 2H), 5.23 (s, 1H), 4.37 (s, 1H), 3.65 (d, J = 5.2 Hz, 1H), 2.91 (s, 2H), 2.63 (d, J = 11.3 Hz, 2H), 2.26 (s, 1H), 2.14-2.06 (m, 1H), 1.82 (p, J = 8.9, 7.9 Hz, 2H), 1.71 (dt, J = 12.7, 7.6 Hz, 2H), 1.57 (d, J = 16.6 Hz, 6H), 1.46 (s, 1H), 1.13-0.98 (m, 8H). | | |
| 122 | 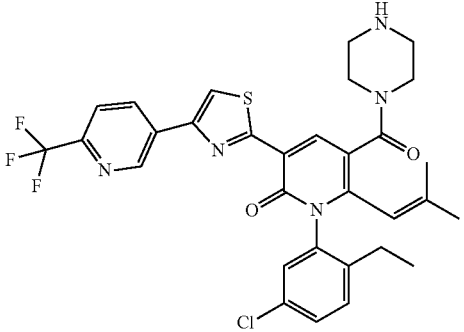 [SMILES: CCc1ccc(Cl)cc1-n1c(C=C(C)C)c(C(=O)N2CCNCC2)cc(-c2nc(-c3ccc(C(F)(F)F)nc3)cs2)c1=O] | B | C | Starting materials: methyl 5-methyl-3-oxohexanoate (step 1), Nitrile 26 (step 2), aniline 4 (step 3), piperazine (used in method V); Methods: S, ester hydrolyzed with LiOH (xs), THF/MeOH/water, 60° C.; U | | | |
| 123 | 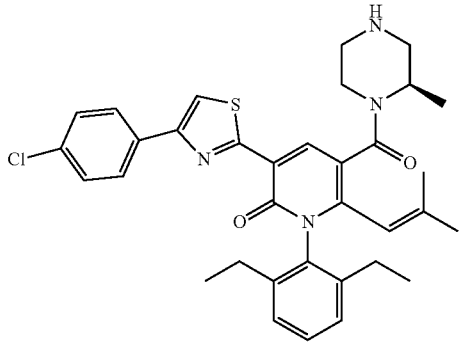 [SMILES: CCc1cccc(CC)c1-n1c(C=C(C)C)c(C(=O)N2CCNC[C@H]2C)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), (R)-tert-butyl 3-methyl-piperazine-1-carboxylate (used in methods V, step 5); Methods: V | $^1$H NMR (400 MHz, DMSO-d$_6$) δ 8.60 (d, J = 23.4 Hz, 1H), 8.22 (s, 1H), 8.09 (dd, J = 9.1, 2.5 Hz, 1H), 7.61-7.45 (m, 2H), 7.41 (td, J = 7.6, 3.6 Hz, 1H), 7.35-7.15 (m, 2H), 5.23 (d, J = 34.4 Hz, 1H), 4.68-4.26 (m, 1H), 4.00 (d, J = 13.1 Hz, 0H), 3.57 (s, 0H), 3.24-2.96 (m, 1H), 2.96-2.53 (m, 3H), 2.42-2.19 (m, 1H), 2.19-1.97 (m, 1H), 1.65-1.52 (m, 4H), 1.49 (d, J = 1.4 Hz, 2H), 1.19 (dd, J = 34.8, 6.7 Hz, 1H), 1.09 (t, J = 7.5 Hz, 2H), 1.04-0.90 (m, 3H). | | |

TABLE 1-continued

Characterization and Enzymatic Inhibition Data for Selected Compounds

| Cpd # | Structure | Data for R132H (μM) | Data for R132C (μM) | Synthesis Method | $^1$H-NMR | $[\alpha]_D^{20}$ (°) (C = 1, CH$_3$Cl$_3$) | ee (%) |
|---|---|---|---|---|---|---|---|
| 124 | 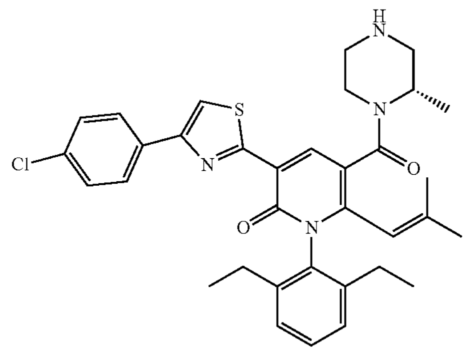 [SMILES: CCc1cccc(CC)c1-n1c(C=C(C)C)c(C(=O)N2CCNC[C@@H]2C)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), (S)-tert-butyl 3-methylpiperazine-1-carboxylate (used in methods V, step 5); Methods: V | $^1$H NMR (400 MHz, DMSO-d$_6$) δ 8.60 (d, J = 23.4 Hz, 1H), 8.22 (s, 1H), 8.09 (dd, J = 9.0, 2.4 Hz, 1H), 7.57-7.46 (m, 2H), 7.41 (td, J = 7.7, 3.6 Hz, 1H), 7.27 (dd, J = 17.5, 7.4 Hz, 2H), 5.23 (d, J = 34.6 Hz, 1H), 4.47 (dd, J = 107.9, 6.3 Hz, 1H), 4.00 (d, J = 12.8 Hz, 0H), 3.57 (s, 0H), 3.23-2.98 (m, 1H), 2.98-2.52 (m, 2H), 2.40-2.18 (m, 1H), 2.10 (ddt, J = 20.9, 13.6, 6.9 Hz, 1H), 1.70-1.52 (m, 4H), 1.49 (d, J = 1.4 Hz, 1H), 1.31-1.12 (m, 1H), 1.09 (t, J = 7.5 Hz, 2H), 1.06-0.87 (m, 4H). | | |
| 125 | 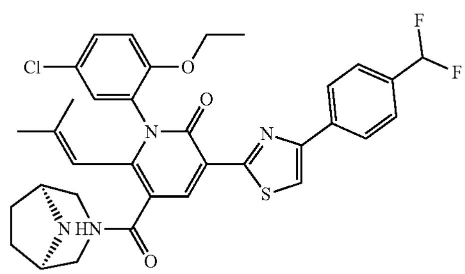 [SMILES: CCOc1ccc(Cl)cc1-n1c(C=C(C)C)c(C(=O)N2C[C@H]3CC[C@@H](C2)N3)cc(-c2nc(-c3ccc(C(F)F)cc3)cs2)c1=O] | A | A | Starting materials: 6,6-dimethyl-dihydro-2H-pyran-2,4(3H)-dione (step 1), Nitrile 24 (step 2), 5-chloro-2-ethoxyaniline (step 3), (1R,5S)-tert-butyl 3,8-diazabicyclo[3.2.1]octane-8-carboxylate (used in methods V, step 5); Methods: V | $^1$H NMR (400 MHz, DMSO-d$_6$) δ 8.60 (s, 1H), 8.36-8.12 (m, 3H), 7.69-7.42 (m, 2H), 7.29-6.85 (m, 3H), 5.46 (s, 1H), 4.29-3.70 (m, 2H), 3.49-3.35 (m, 2H), 3.25-2.88 (m, 2H), 2.37-1.79 (m, 2H), 1.77-1.39 (m, 10H), 1.26-0.96 (m, 5H). | | |
| 126 | 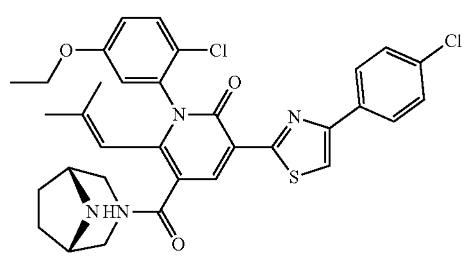 [SMILES: CCOc1ccc(Cl)c(-n2c(C=C(C)C)c(C(=O)N3C[C@H]4CC[C@@H](C3)N4)cc(-c3nc(-c4ccc(Cl)cc4)cs3)c2=O)c1] | A | A | Starting materials: 6,6-dimethyl-dihydro-2H-pyran-2,4(3H)-dione (step 1), Nitrile 1 (step 2), aniline 14 (step 3), (1R, 5S) tert-butyl 3,8-diazabicyclo[3.2.1]octane-8-carboxylate (used in methods V, step 5); Methods: V | $^1$H NMR (400 MHz, DMSO-d$_6$) δ 8.61 (s, 0.5H), 8.51 (m, 0.3 H), 8.23 (s, 1H), 8.08 (d, J = 7.8 Hz, 2H), 7.51 (t, J = 7.6 Hz, 3H), 7.42-7.26 (m, 1H), 7.07 (d, J = 9.6 Hz, 1H), 5.61-5.27 (m, 1H), 4.20 (m, 1H), 4.07 (m, 2H), 4.02-3.69 (m, 1H), 3.45-3.30 (m, 1H), 3.27-2.85 (m, 1.3H), 2.76-2.51 (m, 0.6H), 2.43-2.23 (m, 028 H), 1.76-1.45 (m, 7H), 1.45-1.14 (m, 3H). | | |

TABLE 1-continued

Characterization and Enzymatic Inhibition Data for Selected Compounds

| Cpd # | Structure | Data for R132H (µM) | Data for R132C (µM) | Synthesis Method | ¹H-NMR | $[\alpha]_D^{20}$ (°) (C = 1, CH₃Cl₃) | ee (%) |
|---|---|---|---|---|---|---|---|
| 126-1 | 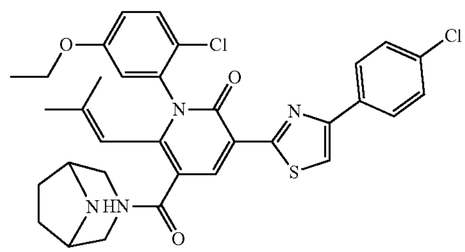 [SMILES: CCOc1ccc(Cl)c(-n2c(C=C(C)C)c(C(=O)N3CC4CCC(C3)N4)cc(-c3nc(-c4ccc(Cl)cc4)cs3)c2=O)c1] | A | A | 1st eluting-Chiral separation-Column: CHIRALPAK IA Mobile Phase: Hex/EtOH/MeOH/DEA 20:40:40:0.1 Flow rate: 40 mL/min | ¹H NMR (400 MHz, DMSO-d₆) δ 8.61 (s, 0.5H), 8.51 (m, 0.3H), 8.22 (s, 1H), 8.12-8.05 (m, 3H), 7.59-7.47 (m, 3H), 7.41-7.33 (m, 1H), 7.15-7.03 (m, 1H), 5.61-5.28 (m, 1H), 4.20 (t, J = 14.5 Hz, 1H), 4.07 (q, J = 6.9 Hz, 2H), 4.01-3.73 (m, 0.7H), 3.39 (m, 1.4H), 3.27-2.79 (m, 2.8H), 2.72-2.54 (m, 0.3H), 2.43-2.24 (m, 1.2H), 1.76-1.45 (m, 7H), 1.43-1.20 (m, 3H). | −5.3 | >99% |
| 126-2 | 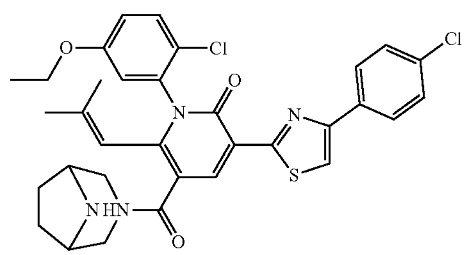 [SMILES: CCOc1ccc(Cl)c(-n2c(C=C(C)C)c(C(=O)N3CC4CCC(C3)N4)cc(-c3nc(-c4ccc(Cl)cc4)cs3)c2=O)c1] | C | C | 2nd eluting-Chiral separation-Column: CHIRALPAK IA Mobile Phase: Hex/EtOH/MeOH/DEA 20:40:40:0.1 Flow rate: 40 mL/min | ¹H NMR (400 MHz, DMSO-d₆) δ 8.61 (s, 0.5H), 8.51 (m, 0.3H), 8.23 (s, 1H), 8.08 (d, J = 8.5 Hz, 2H), 7.51 (t, J = 7.6 Hz, 3H), 7.41-7.33 (m, 1H), 7.07 (d, J = 9.4 Hz, 1H), 5.62-5.31 (m, 1H), 4.20 (t, J = 14.4 Hz, 1H), 4.07 (q, J = 6.9 Hz, 2H), 4.00-3.70 (m, 0.7H), 3.39 (m, 1.4H), 3.25-2.80 (m, 1.8H), 2.78-2.51 (m, 0.2H), 2.44-2.19 (m, 0.8H), 1.74-1.46 (m, 7H), 1.44-1.20 (m, 3H). | +4.6 | 96.1 |
| 127 | 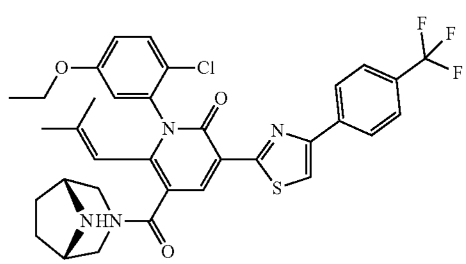 [SMILES: CCOc1ccc(Cl)c(-n2c(C=C(C)C)c(C(=O)N3C[C@H]4CC[C@@H](C3)N4)cc(-c3nc(-c4ccc(C(F)(F)F)cc4)cs3)c2=O)c1] | A | A | Starting materials: 6,6-dimethyl-dihydro-2H-pyran-2,4(3H)-dione (step 1), Nitrile 7 (step 2), aniline 14 (step 3), (1R, 5S) tert-butyl 3,8-diazabicyclo[3.2.1]octane-8-carboxylate (used in methods V, step 5); Methods: V | ¹H NMR (400 MHz, DMSO-d₆) δ 8.63 (s, 0H), 8.53 (d, J = 11.7 Hz, 0H), 8.39 (s, 1H), 8.28 (d, J = 7.9 Hz, 2H), 7.82 (d, J = 8.0 Hz, 2H), 7.53 (dd, J = 21.9, 8.9 Hz, 1H), 7.46-7.30 (m, 1H), 7.07 (d, J = 9.3 Hz, 1H), 5.63-5.31 (m, 1H), 4.33-4.12 (m, 1H), 4.07 (q, J = 7.0 Hz, 2H), 3.99-3.73 (m, 1H), 3.48-3.33 (m, 0H), 3.25-2.79 (m, 1H), 2.78-2.53 (m, 0H), 2.30 (p, J = 1.9 Hz, 1H), 1.78-1.46 (m, 7H), 1.46-1.19 (m, 3H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 128 | 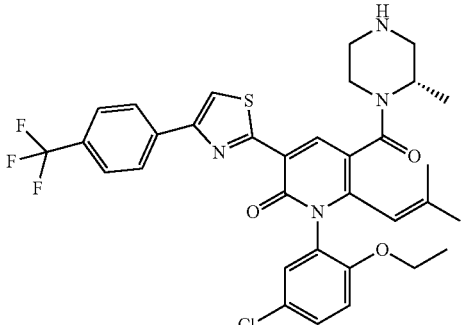 | A | B | Starting materials: 6,6-dimethyl-dihydro-2H-pyran-2,4(3H)-dione (step 1), Nitrile 7 (step 2), 5-chloro-2-ethoxyaniline (step 3); (S)-tert-butyl 3-methylpiperazine-1-carboxylate (step 5); Methods: V | ¹H NMR (400 MHz, Chloroform-d) δ 8.89-8.67 (m, 1H, rotameric), 8.12 (d, J = 8.0 Hz, 2H), 7.74-7.61 (m, 3H), 7.37 (d, J = 8.7 Hz, 1H), 7.23-7.07 (m, 1H), 7.00-6.89 (m, 1H), 5.47 (m, 1H, rotameric), 4.92-4.83 (m, 1H), 4.12-2.51 (m, 7H), 1.71-1.43 (m, 8H), 1.38-1.13 (m, 6H). | | |
| 129 | 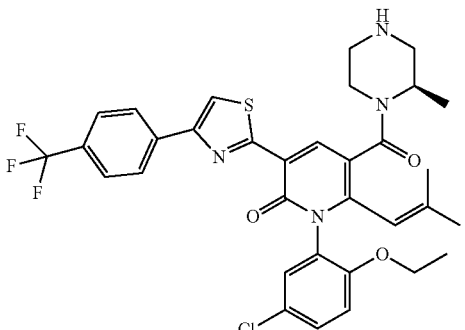 | A | A | Starting materials: 6,6-dimethyl-dihydro-2H-pyran-2,4(3H)-dione (step 1), Nitrile 7 (step 2), 5-chloro-2-ethoxyaniline (step 3); (R)-tert-butyl 3-methylpiperazine-1-carboxylate (step 5); Methods: V | ¹H NMR (400 MHz, Chloroform-d) δ 8.88-8.65 (m, 1H, rotameric), 8.12 (d, J = 8.0 Hz, 2H), 7.75-7.60 (m, 3H), 7.37 (d, J = 8.7 Hz, 1H), 7.24-7.07 (m, 1H), 7.00-6.87 (m, 1H), 5.46 (m, 1H, rotameric), 4.91-4.82 (m, 1H), 4.15-2.53 (m, 7H), 1.70-1.45 (m, 8H), 1.40-1.15 (m, 6H). | | |
| 130 | 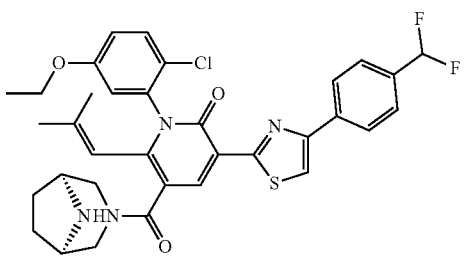 [SMILES: CCOc1ccc(Cl)c(-n2c(C=C(C)C)c(C(=O)N3C[C@H]4CC[C@@H](C3)N4)cc(-c3nc(-c4ccc(C(F)F)cc4)cs3)c2=O)c1] | A | A | Starting materials: 6,6-dimethyl-dihydro-2H-pyran-2,4(3H)-dione (step 1), Nitrile 24 (step 2), aniline 14 (step 3), (1R,5S)-tert-butyl 3,8-diazabicyclo[3.2.1]octane-8-carboxylate (used in methods V, step 5); Methods: V | ¹H NMR (400 MHz, DMSO-d$_6$) δ 8.45 (d, J = 1.7 Hz, 1H), 8.34-8.14 (m, 3H), 7.65 (d, J = 8.0 Hz, 2H), 7.42 (d, J = 8.9 Hz, 1H), 7.25-6.83 (m, 2H), 5.26 (s, 1H), 4.37-3.85 (m, 2H), 3.66-3.38 (m, 2H), 3.09-2.57 (m, 2H), 2.30 (p, J = 1.9 Hz, 2H), 2.15-1.79 (m, 2H), 1.81-1.48 (m, 5H), 1.47-1.26 (m, 4H), 1.22-0.84 (m, 2H). | | |
| 131 | 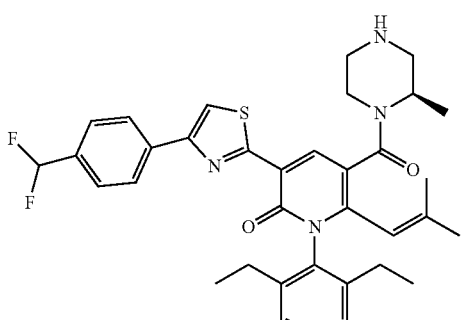 | A | A | Starting materials: 6,6-dimethyl-dihydro-2H-pyran-2,4(3H)-dione (step 1), Nitrile 24 (step 2), (R)-tert-butyl 3-methylpiperazine-1-carboxylate (used in methods V, step 5); Methods: V | ¹H NMR (400 MHz, DMSO-d$_6$) δ 8.78 (s, 1H), 8.38-8.13 (m, 2H), 7.65 (d, J = 8.0 Hz, 2H), 7.45-7.15 (m, 2H), 7.00 (d, J = 55.9 Hz, 2H), 5.23 (d, J = 34.7 Hz, 1H), 3.59-3.34 (m, 2H), 2.80-2.54 (m, 2H), 2.37-1.94 (m, 3H), 1.68-1.40 (m, 9H), 1.29-0.90 (m, 12H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 132 | 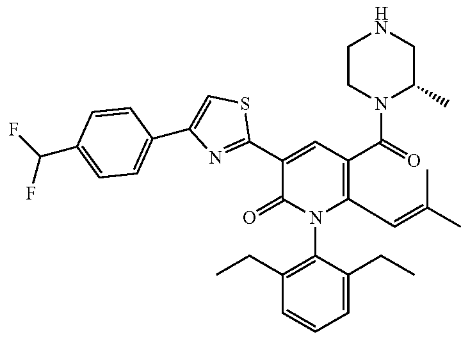 [SMILES: CCc1cccc(CC)c1-n1c(C=C(C)C)c(C(=O)N2CCNC[C@@H]2C)cc(-c2nc(-c3ccc(C(F)F)cc3)cs2)c1=O] | A | A | Starting materials: 6,6-dimethyl-dihydro-2H-pyran-2,4(3H)-dione (step 1), Nitrile 24 (step 2), (S)-tert-butyl 3-methylpiperazine-1-carboxylate (used in methods V, step 5); Methods: V | ¹H NMR (400 MHz, DMSO-d$_6$) δ 8.70-8.55 (m, 1H), 8.30 (s, 1H), 8.21 (d, J = 7.8 Hz, 3H), 7.65 (d, J = 8.1 Hz, 3H), 7.41 (td, J = 7.7, 3.7 Hz, 1H), 7.36-7.16 (m, 3H), 7.00 (d, J = 55.9 Hz, 1H), 5.27 (s, 1H), 4.09-3.91 (m, 0H), 2.83-2.61 (m, 2H), 2.38-2.18 (m, 2H), 2.17-2.00 (m, 2H), 1.64-1.45 (m, 8H), 1.29-1.05 (m, 5H), 1.06-0.92 (m, 6H). | | |
| 133 | 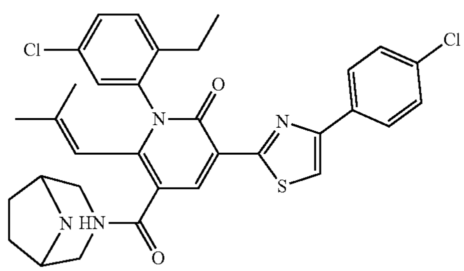 [SMILES: CCc1ccc(Cl)cc1-n1c(C=C(C)C)c(C(=O)N2CC3CCC(C2)N3)cc(-c2nc(-c3ccc(Cl)cc3)cs2)c1=O] | A | A | Starting materials: 6,6-dimethyl-dihydro-2H-pyran-2,4(3H)-dione (step 1), Nitrile 1 (step 2), Aniline 4 (step 3), (1R,5S) tert-butyl 3,8-diazabicyclo[3.2.1]octane-8-carboxylate (step 5); Methods: V | ¹H NMR (400 MHz, DMSO-d$_6$) δ 8.61 (s, 1H), 8.21 (s, 1H), 8.08 (d, J = 6.1 Hz, 2H), 7.76-7.26 (m, 5H), 5.54-5.25 (m, 1H, rotameric), 4.28-3.73 (m, 1H), 3.52-3.21 (m, 4H), 3.13-2.85 (m, 2H), 2.71-2.55 (m, 1H), 2.37-2.02 (m, 2H), 1.69-1.52 (m, 8H), 1.15-0.91 (m, 3H). | | |
| 133-1 | 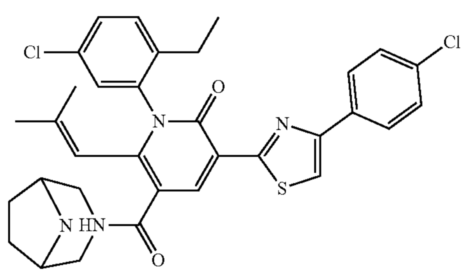 [SMILES: CCc1ccc(Cl)cc1-n1c(C=C(C)C)c(C(=O)N2CC3CCC(C2)N3)cc(-c2nc(-c3ccc(Cl)cc3)cs2)c1=O] | B | A | Chiral separation of 133: ChiralPak IA (5 × 50 cm, 20 um); Hex/EtOH/DEA (40:60:0.04); 35 mL/min | ¹H NMR (400 MHz, Chloroform-d) δ 8.92-8.65 (m, 1H, rotameric), 8.00-7.89 (m, 3H), 7.58 (s, 1H), 7.41 (d, J = 8.2 Hz, 2H), 7.32 (dd, J = 8.5, 4.3 Hz, 1H), 7.06 (d, J = 83.1 Hz, 1H), 5.59-5.22 (m, 1H, rotameric), 4.63-4.14 (m, 1H), 3.78-2.85 (m, 6H), 2.49-1.42 (m, 12H), 1.09-0.83 (m, 3H). | +2.1 | >99 |
| 133-2 | 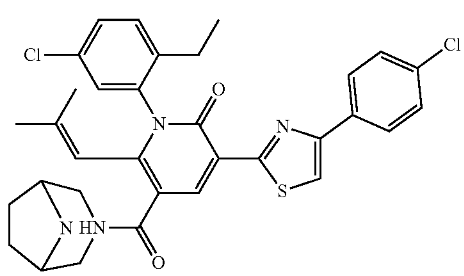 [SMILES: CCc1ccc(Cl)cc1-n1c(C=C(C)C)c(C(=O)N2CC3CCC(C2)N3)cc(-c2nc(-c3ccc(Cl)cc3)cs2)c1=O] | C | B | Chiral separation of 133: ChiralPak IA (5 × 50 cm, 20 um); Hex/EtOH/DEA (40:60:0.04); 35 mL/min | ¹H NMR (400 MHz, Chloroform-d) δ 8.91-8.66 (m, 1H, rotameric), 8.01-7.88 (m, 3H), 7.59 (s, 1H), 7.41 (d, J = 8.2 Hz, 2H), 7.34 (dd, J = 8.5, 4.3 Hz, 1H), 7.06 (d, J = 83.1 Hz, 1H), 5.58-5.21 (m, 1H, rotameric), 4.63-4.16 (m, 1H), 3.79-2.82 (m, 6H), 2.48-1.40 (m, 12H), 1.08-0.80 (m, 3H). | −2.5 | 93.7 |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH$_3$Cl$_3$) | ee (%) |
|---|---|---|---|---|---|---|---|
| 134 | 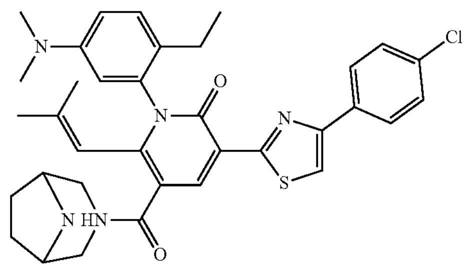 [SMILES: CCc1ccc(N(C)C)cc1-n1c(C=C(C)C)c(C(=O)N2CC3CCC(C2)N3)cc(-c2nc(-c3ccc(Cl)cc3)cs2)c1=O] | A | A | Starting materials: 6,6-dimethyldihydro-2H-pyran-2,4(3H)-dione (step 1), Nitrile 1 (step 2), aniline 5 (step3), (1R,5S)-tert-butyl 3,8-diazabicyclo[3.2.1]octane-8-carboxylate (used in methods V, step 5); Methods: V | ¹H NMR (400 MHz, DMSO-d$_6$) δ 8,67 (s, 1H), 8.22 (s, 1H), 8.09 (dd, J = 8.6, 1.9 Hz, 2H), 7.57-7.46 (m, 2H), 7.20 (t, J = 10.2 Hz, 2H), 6.86-6.73 (m, 1H), 5.49 (s, 1H), 4.43 (t, J = 17.3 Hz, 1H), 4.09 (s, 2H), 3.84 (dd, J = 55.4, 14.6 Hz, 2H), 3.01-2.71 (m, 4H), 2.35-2.16 (m, 1H), 2.04-1.77 (m, 5H), 1.56 (dd, J = 23.6, 13.5 Hz, 8H), 1.06 (t, J = 7.5 Hz, 1H), 0.91 (dt, J = 14.9, 7.6 Hz, 3H). | | |
| 135 | 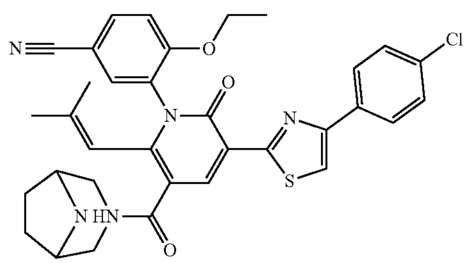 [SMILES: CCOc1ccc(C#N)cc1-n1c(C=C(C)C)c(C(=O)N2CC3CCC(C2)N3)cc(-c2nc(-c3ccc(Cl)cc3)cs2)c1=O] | A | A | Starting materials: 6,6-dimethyldihydro-2H-pyran-2,4(3H)-dione (step 1), Nitrile 1 (step 2) aniline 21 (step 3), (1R,5S)-tert-butyl 3,8-diazabicyclo[3.2.1]octane-8-carboxylate (used in methods V, step 5); Methods: V | ¹H NMR (400 MHz, DMSO-d$_6$) δ 8.67 (s, 1H), 8.25 (s, 1H), 8.18-7.87 (m, 4H), 7.59-7.31 (m, 3H), 5.51 (s, 1H), 4.52-3.83 (m, 2H), 3.77-3.50 (m, 2H), 3.07-2.85 (m, 2H), 1.87 (d, J = 22.1 Hz, 3H), 1.71-1.38 (m, 9H), 1.31-0.95 (m, 3H). | | |
| 136 | 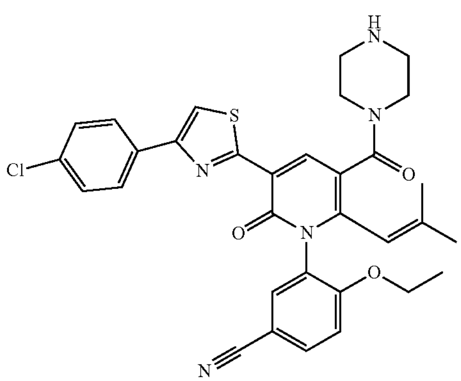 [SMILES: CCOc1ccc(C#N)cc1-n1c(C=C(C)C)c(C(=O)N2CCNCC2)cc(-c2nc(-c3ccc(Cl)cc3)cs2)c1=O] | A | A | Starting materials: 6,6-dimethyldihydro-2H-pyran-2,4(3H)-dione (step 1), Nitrile 1 (step 2), aniline 21 (step 3), Methods: V | ¹H NMR (400 MHz, DMSO-d$_6$) δ 8.53 (s, 1H), 8.25 (s, 1H), 8.17-7.88 (m, 4H), 7.68-7.25 (m, 3H), 5.52 (s, 1H), 4.31-3.78 (m, 2H), 3.71-3.38 (m, 2H), 3.26-2.78 (m, 4H), 1.54 (dd, J = 29.8, 1.3 Hz, 9H), 1.34-0.94 (m, 4H). | | |
| 137 | 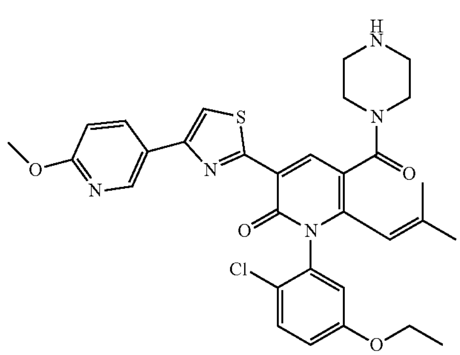 [SMILES: CCOc1ccc(Cl)c(-n2c(C=C(C)C)c(C(=O)N3CCNCC3)cc(-c3nc(-c4ccc(OC)nc4)cs3)c2=O)c1] | A | A | Starting materials: 6,6-dimethyldihydro-2H-pyran-2,4(3H)-dione (step 1), Nitrile 38 (step 2), aniline 14 (step 3), Methods: V | ¹H NMR (400 MHz, DMSO-d$_6$) δ 8.85 (d, J = 2.2 Hz, 1H), 8.64 (s, 1H), 8.32 (dd, J = 8.6, 2.5 Hz, 2H), 8.14 (s, 1H), 7.59-7.41 (m, 2H), 7.18 (t, J = 8.5 Hz, 1H), 6.92 (dd, J = 8.7, 0.7 Hz, 1H), 5.52 (s, 1H), 4.13-3.91 (m, 2H), 3.30-3.22 (m, 4H), 1.75-1.50 (m, 12H), 1.20-0.99 (m, 3H). | | |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH₃Cl₃) | ee (%) |
|---|---|---|---|---|---|---|---|
| 138 | 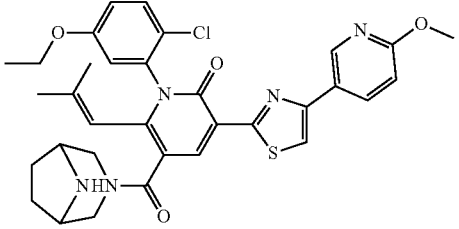 [SMILES: CCOc1ccc(Cl)c(-n2c(C=C(C)C)c(C(=O)N3CC4CCC(C3)N4)cc(-c3nc(-c4ccc(OC)nc4)cs3)c2=O)c1] | A | A | Starting materials: 6,6-dimethyldihydro-2H-pyran-2,4(3H)-dione (step 1), Nitrile 38 (step 2), aniline 14 (step 3), (1R,5S)-tert-butyl 3,8-diazabicyclo[3.2.1]octane-8-carboxylate (used in methods V, step 5); Methods: V | ¹H NMR (400 MHz, DMSO-d₆) δ 8.92-8.82 (m, 1H), 8.66 (s, 1H), 8.33 (dd, J = 8.6, 2.5 Hz, 2H), 8.14 (s, 1H), 7.64-7.44 (m, 1H), 7.17 (d, J = 8.9 Hz, 1H), 6.92 (dd, J = 8.6, 0.8 Hz, 1H), 5.47 (s, 1H), 4.41 (t, J = 17.3 Hz, 2H), 4.15-3.92 (m, 2H), 3.74-3.29 (m, 6H), 2.97 (d, J = 13.9 Hz, 2H), 189-1.46 (m, 9H), 1.18-1.01 (m, 2H). | | |
| 139 | 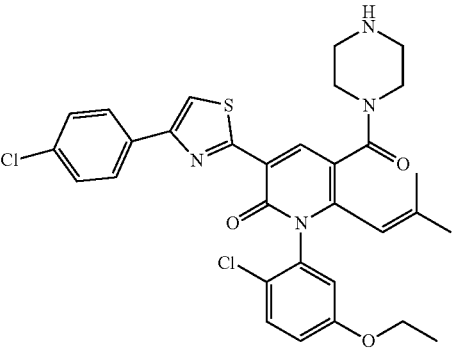 [SMILES: CCOc1ccc(Cl)c(-n2c(C=C(C)C)c(C(=O)N3CCNCC3)cc(-c3nc(-c4ccc(Cl)cc4)cs3)c2=O)c1] | A | A | Starting material: 6,6-dimethyldihydro-2H-pyran-2,4(3H)-dione (step1 method V); nitrile 1 (step2 method V); aniline 14 (step 3), Methods: V | TFA salt: ¹H NMR (400 MHz, CD₃OD) δ 8.86 (s, 1H), 8.05 (d, J = 8.4 Hz, 2H), 7.96 (s, 1H), 7.56-7.40 (m, 3H), 7.18-6.99 (m, 3H), 5.63 (s, 1H), 4.35-3.99 (m, 4H), 3.86-3.54 (m, 4H), 3.25-3.10 (m, 2H), 1.70 (s, 6H), 1.40 (m, 3H). Aliphatic region complicated significantly by amide rotamers. | | |
| 139-1 | 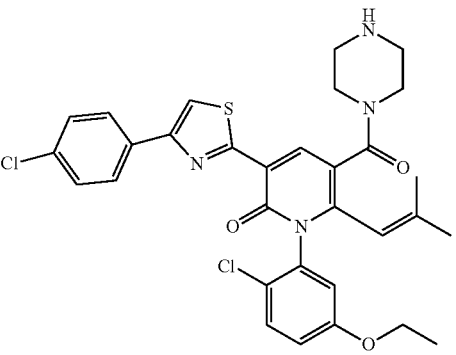 [SMILES: CCOc1ccc(Cl)c(-n2c(C=C(C)C)c(C(=O)N3CCNCC3)cc(-c3nc(-c4ccc(Cl)cc4)cs3)c2=O)c1] | A | A | 1st eluting-Chiral separation-Column: CHIRALPAK IA Mobile Phase: Hex/EtOH/DEA 40:60:0.04 Flow rate: 35 mL/min | ¹H NMR (400 MHz, DMSO-d₆) δ 8.62 (s, 1H), 8.24 (s, 1H), 8.15-8.01 (m, 3H), 7.57-7.44 (m, 4H), 7.16-7.02 (m, 1H), 5.49 (s, 1H), 4.11-3.95 (m, 2H), 3.62-3.60 (m, 2H), 2.90-2.57 (m, 4H), 1.66-1.49 (m, 7H), 1.41-1.13 (m, 5H). | +2.9 | 91.2 |
| 139-2 | 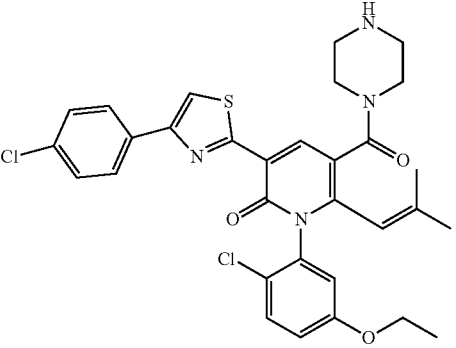 [SMILES: CCOc1ccc(Cl)c(-n2c(C=C(C)C)c(C(=O)N3CCNCC3)cc(-c3nc(-c4ccc(Cl)cc4)cs3)c2=O)c1] | B | C | 2nd eluting-Chiral separation-Column: CHIRALPAK IA Mobile Phase: Hex/EtOH/DEA 40:60:0.04 Flow rate: 35 mL/min | ¹H NMR (400 MHz, DMSO-d₆) δ 8.61 (s, 1H), 8.24 (s, 1H), 8.14-8.04 (m, 2H), 7.59-7.45 (m, 3H), 7.17-7.02 (m, 2H), 5.49 (s, 1H), 4.16-3.94 (m, 2H), 3.59-3.54 (m, 2H), 2.82-2.53 (m, 4H), 1.81-1.50 (m, 7H), 1.42-1.13 (m, 5H). | −2.9 | 96.3 |

TABLE 1-continued

Characterization and Enzymatic Inhibition Data for Selected Compounds

| Cpd # | Structure | Data for R132H (μM) | Data for R132C (μM) | Synthesis Method | $^{1}$H-NMR | $[\alpha]_D^{20}$ (°) (C = 1, CH$_3$Cl$_3$) | ee (%) |
|---|---|---|---|---|---|---|---|
| 140-1 | 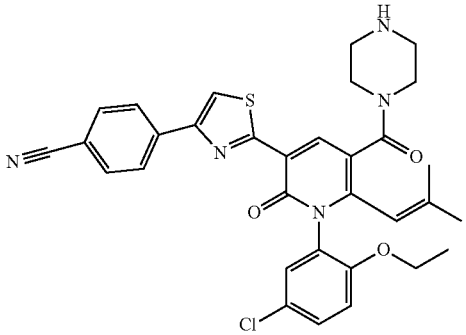 [SMILES: CCOc1ccc(Cl)cc1-n1c(C=C(C)C)c(C(=O)N2CCNCC2)cc(-c2nc(-c3ccc(C#N)cc3)cs2)c1=O] | A | A | Starting materials: 6,6-dimethyldihydro-2H-pyran-2,4(3H)-dione (step 1), Nitrile 37 (step 2), 5-chloro-2-ethoxyaniline (step 3), Methods: V and then Chiral separation condition: ChiralPak IA (5 × 50 cm, 20 um); Hex/EtOH/DEA (40:60:0.04); 35 mL/min. 1$^{st}$ eluting | $^{1}$H NMR (400 MHz, DMSO-d$_6$) δ 8.59 (d, J = 2.7 Hz, 1H), 8.43 (s, 1H), 8.33-8.21 (m, 2H), 7.98-7.86 (m, 2H), 7.64 (d, J = 2.7 Hz, 1H), 7.56-7.42 (m, 1H), 7.19 (dd, J = 27.5, 8.9 Hz, 1H), 5.48 (s, 1H), 4.14-3.78 (m, 2H), 3.52 (s, 1H), 3.27-3.10 (m, 1H), 2.80-2.52 (m, 1H), 1.54 (dd, J = 24.8, 1.4 Hz, 10H), 1.24-1.00 (m, 4H). | +2.4 | 98.1 |
| 140-2 | 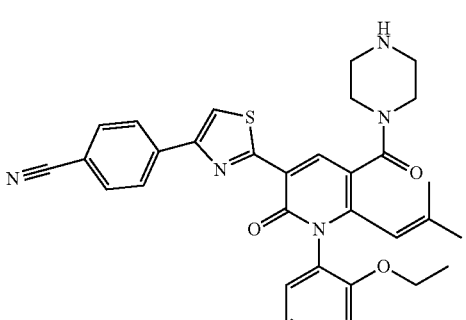 | A | B | Starting materials: 6,6-dimethyldihydro-2H-pyran-2,4(3H)-dione (step 1), Nitrile 37 (step 2), 5-chloro-2-ethoxyaniline (step 3), Methods: V and then Chiral separation condition: ChiralPak IA (5 × 50 cm, 20 um); Hex/EtOH/DEA (40:60:0.04); 35 mL/min. 2$^{nd}$ eluting | $^{1}$H NMR (400 MHz, DMSO-d$_6$) δ 8.59 (s, 1H), 8.43 (s, 1H), 8.34-8.21 (m, 2H), 7.97-7.86 (m, 3H), 7.70-7.45 (m, 1H), 7.19 (dd, J = 27.5, 8.9 Hz, 1H), 5.48 (s, 1H), 4.13-3.78 (m, 2H), 3.46 (d, J = 44.2 Hz, 1H), 3.22 (dt, J = 13.6, 9.7 Hz, 2H), 2.78-2.52 (m, 2H), 1.54 (dd, J = 24.7, 1.4 Hz, 9H), 1.33-0.88 (m, 3H). | −3.3 | 89.0 |
| 141-1 | 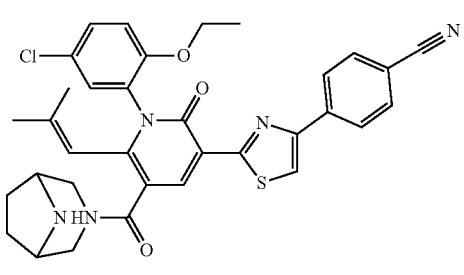 [SMILES: CCOc1ccc(Cl)cc1-n1c(C=C(C)C)c(C(=O)N2CC3CCC(C2)N3)cc(-c2nc(-c3ccc(C#N)cc3)cs2)c1=O] | A | A | Starting materials: 6,6-dimethyldihydro-2H-pyran-2,4(3H)-dione (step 1), Nitrile 37 (step 2), 5-chloro-2-ethoxyaniline (step 3), (1R,5S)-tert-butyl 3,8-diazabicyclo[3.2.1]octane-8-carboxylate (used in methods V, step 5); Methods: V and then Chiral separation condition: ChiralPak IA (5 × 50 cm, 20 um); MeOH/DEA (100:0.1); 40 mL/min | 1H NMR (400 MHz, DMSO-d$_6$) δ 8.60 (s, 1H), 8.44 (d, J = 3.8 Hz, 1H), 8.29-8.21 (m, 2H), 7.93 (d, J = 8.1 Hz, 2H), 7.69-7.60 (m, 1H), 7.57-7.41 (m, 1H), 7.19 (dd, J = 31.3, 8.9 Hz, 1H), 5.46 (s, 1H), 4.27-3.93 (m, 2H), 3.84 (t, J = 8.5 Hz, 2H), 3.46-3.34 (m, 1H), 3.28-2.96 (m, 2H), 2.69-2.54 (m, 1H), 1.72-1.32 (m, 10H), 1.23-0.97 (m, 4H). | +2.6 | >98 |
| 141-2 | 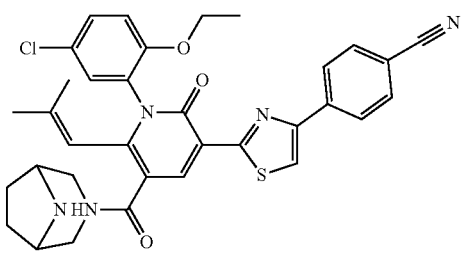 [SMILES: CCOc1ccc(Cl)cc1-n1c(C=C(C)C)c(C(=O)N2CC3CCC(C2)N3)cc(-c2nc(-c3ccc(C#N)cc3)cs2)c1=O] | B | A | Starting materials: 6,6-dimethyldihydro-2H-pyran-2,4(3H)-dione (step 1), Nitrile 38 (step 2), 5-chloro-2-ethoxyaniline (step 3), (1R,5S)-tert-butyl 3,8-diazabicyclo[3.2.1]octane-8-carboxylate (used in methods V, step 5); Methods: V and then Chiral | $^{1}$H NMR (400 MHz, DMSO-d$_6$) δ 8.60 (s, 1H), 8.44 (d, J = 3.8 Hz, 2H), 8.26 (dd, J = 8.9, 3.3 Hz, 2H), 7.98-7.88 (m, 2H), 7.54-7.43 (m, 1H), 7.16 (d, J = 9.0 Hz, 1H), 5.46 (s, 1H), 3.85 (d, J = 6.6 Hz, 2H), 3.37 (d, J = 3.7 Hz, 1H), 3.30- | −2.9 | 89 |

TABLE 1-continued

Characterization and Enzymatic Inhibition Data for Selected Compounds

| Cpd # | Structure | Data for R132H (μM) | Data for R132C (μM) | Synthesis Method | $^1$H-NMR | $[\alpha]_D^{20}$ (°) (C = 1, CH$_3$Cl$_3$) | ee (%) |
|---|---|---|---|---|---|---|---|
| | | | | separation condition: ChiralPak IA (5 × 50 cm, 20 um); MeOH/DEA (100:0.1); 40 mL/min | 2.96 (m, 2H), 2.73-2.53 (m, 1H), 1.71-1.34 (m, 9H), 1.26-0.98 (m, 4H), 0.95-0.71 (m, 2H). | | |
| 143 | 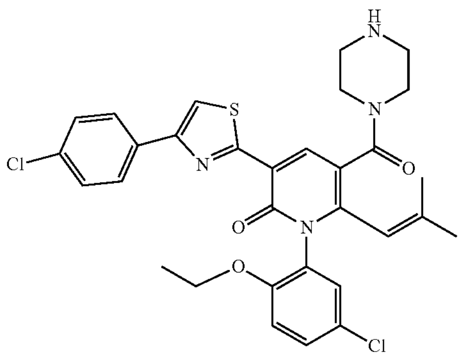 [SMILES: CCOc1ccc(Cl)cc1-n1c(C=C(C)C)c(C(=O)N2CCNCC2)cc(-c2nc(-c3ccc(Cl)cc3)cs2)c1=O] | A | A | Starting materials: 6,6-dimethyldihydro-2H-pyran-2,4(3H)-dione (step 1), Nitrile 1 (step 2), 5-chloro-2-ethoxyaniline (step 3); Methods: V | $^1$H NMR (400 MHz, Chloroform-d) δ 8.79 (s, 1H), 8.77-8.30 (dd, 1H, rotameric), 7.94 (d, J = 8.5 Hz, 2H), 7.56 (s, 1H), 7.42-7.30 (m, 3H), 7.25-7.13 (m, 1H), 6.93 (d, J = 8.9 Hz, 1H), 5.49 (s, 1H), 4.10-3.25 (m, 5H), 2.95-2.85 (m, 5H), 1.66-1.61 (m, 6H), 1.21 (t, J = 7.0 Hz, 3H). | | |
| 143-1 | 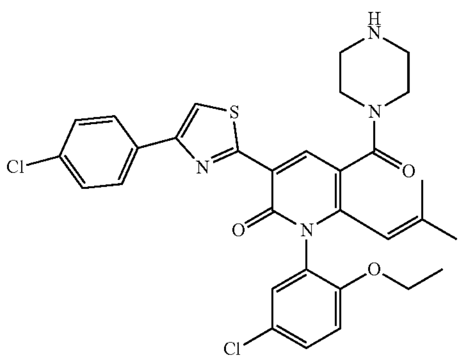 [SMILES: CCOc1ccc(Cl)cc1-n1c(C=C(C)C)c(C(=O)N2CCNCC2)cc(-c2nc(-c3ccc(Cl)cc3)cs2)c1=O] | A | B | Chiral separation of 463: ChiralPak IA (5 × 50 cm, 20 um); Hex/EtOH/DEA (40:60:0.04); 35 mL/min | $^1$H NMR (400 MHz, DMSO-d$_6$) δ 8.57 (s, 1H), 8.22 (s, 1H), 8.16-7.99 (m, 3H), 7.62-7.37 (m, 3H), 7.17 (s, 1H), 5.47 (s, 1H), 3.22-318 (m, 3H), 2.60-2.50 (m, 3H), 1.65-1.45 (m, 9H), 1.23-0.90 (m, 4H). | −3.6 | >98 |
| 143-2 | 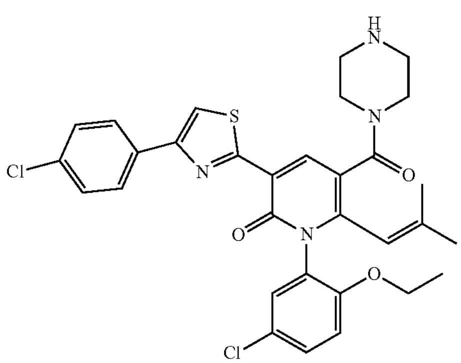 [SMILES: CCOc1ccc(Cl)cc1-n1c(C=C(C)C)c(C(=O)N2CCNCC2)cc(-c2nc(-c3ccc(Cl)cc3)cs2)c1=O] | A | A | Chiral separation of 463: ChiralPak IA (5 × 50 cm, 20 um); Hex/EtOH/DEA (40:60:0.04); 35 mL/min | $^1$H NMR (400 MHz, DMSO-d$_6$) δ 8.57 (s, 1H), 8.22 (s, 1H), 8.09 (d, J = 8.5 Hz, 2H), 7.57-7.43 (m, 4H), 7.16 (d, J = 9.0 Hz, 1H), 5.47 (s, 1H), 4.12-3.79 (m, 2H), 3.54 (s, 1H), 3.23 (t, J = 14.2 Hz, 3H), 2.79-2.54 (m, 5H), 1.64-1.44 (m, 6H), 1.18-0.96 (m, 3H). | +3.7 | >95 |

TABLE 1-continued

Characterization and Enzymatic Inhibition Data for Selected Compounds

| Cpd # | Structure | Data for R132H (μM) | Data for R132C (μM) | Synthesis Method | ¹H-NMR | $[\alpha]_D^{20}$ (°) (C = 1, CH₃Cl₃) | ee (%) |
|---|---|---|---|---|---|---|---|
| 144-1 | 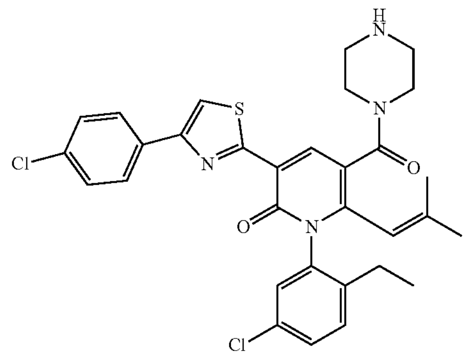 [SMILES: CCc1ccc(Cl)cc1-n1c(C=C(C)C)c(C(=O)N2CCNCC2)cc(-c2nc(-c3ccc(Cl)cc3)cs2)c1=O] | A | A | Chiral separation: Column: CHIRALPAK IA Mobile Phase: Hex/EtOH/DEA 40:60:0.04 Flow rate: 35 mL/min | ¹H NMR (400 MHz, DMSO-d₆) δ 8.61 (s, 1H), 8.23 (s, 1H), 8.14-8.05 (m, 2H), 7.55-7.40 (m, 5H), 5.45 (s, 1H), 3.62-3.58 (m, 2H), 2.80-2.53 (m, 3H), 2.17-2.02 (m, 2H), 1.64-1.48 (m, 7H), 1.22 (d, J = 10.8 Hz, 2H), 1.13 (s, 0H), 1.13-0.89 (m, 4H). | +0.7 | >98 |
| 144-2 | 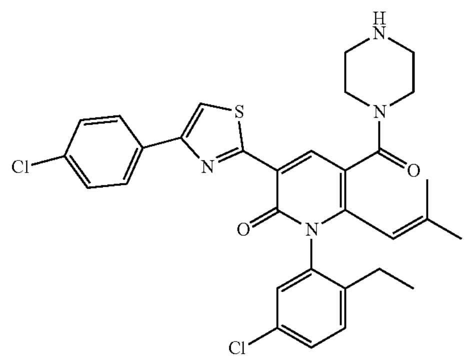 [SMILES: CCc1ccc(Cl)cc1-n1c(C=C(C)C)c(C(=O)N2CCNCC2)cc(-c2nc(-c3ccc(Cl)cc3)cs2)c1=O] | A | B | Chiral separation: Column: CHIRALPAK IA Mobile Phase: Hex/EtOH/DEA 40:60:0.04 Flow rate: 35 mL/min | ¹H NMR (400 MHz, DMSO-d₆) δ 8.62 (s, 1H), 8.23 (s, 1H), 8.17-8.02 (m, 3H), 7.59-7.39 (m, 5H), 5.46 (s, 1H), 2.94-2.56 (m, 4H), 2.24-2.01 (m, 2H), 1.56 (d, J = 13.8 Hz, 8H), 1.29-0.90 (m, 7H). | −0.8 | 87 |
| 145 | 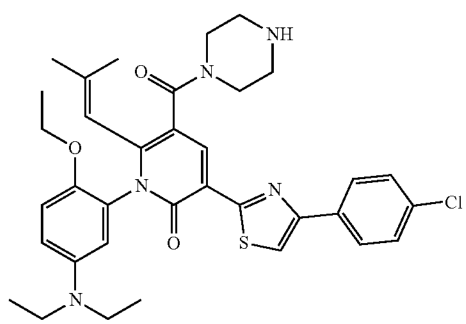 [SMILES: CCOc1ccc(N(CC)CC)cc1-n1c(C=C(C)C)c(C(=O)N2CCNCC2)cc(-c2nc(-c3ccc(Cl)cc3)cs2)c1=O] | A | A | Starting materials: 6,6-dimethyldihydro-2H-pyran-2,4(3H)-dione (step 1), Nitrile 1 (step 2), aniline 18 (step 3), Methods: V | ¹H NMR (400 MHz, DMSO-d₆) δ 8.55 (d, J = 3.2 Hz, 1H), 8.20 (d, J = 3.3 Hz, 1H), 8.15-8.01 (m, 2H), 7.65-7.42 (m, 3H), 7.11-6.36 (m, 2H), 5.45 (d, J = 12.2 Hz, 1H), 4.01-3.41 (m, 2H), 3.32-3.03 (m, 7H), 2.80-2.52 (m, 2H), 1.52 (dd, J = 14.2, 2.1 Hz, 9H), 1.03 (ddt, J = 23.2, 13.8, 6.9 Hz, 9H). | | |
| 146 | 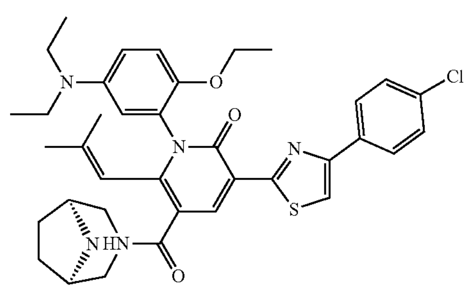 [SMILES: CCOc1ccc(N(CC)CC)cc1-n1c(C=C(C)C)c(C(=O)N2C[C@H]3CC[C@@H](C2)N3)cc(-c2nc(-c3ccc(Cl)cc3)cs2)c1=O] | A | B | Starting materials: 6,6-dimethyldihydro-2H-pyran-2,4(3H)-dione (step 1), Nitrile 1 (step 2), aniline 18 (step 3), (1R,5S)-tert-butyl 3,8-diazabicyclo[3.2.1]octane-8-carboxylate (used in methods V, step 5); Methods: V | ¹H NMR (400 MHz, DMSO-d₆) δ 8.56 (s, 1H), 8.20 (s, 1H), 8.17-7.99 (m, 2H), 7.51 (t, J = 7.5 Hz, 3H), 7.13-6.43 (m, 2H), 5.45 (s, 1H), 4.20-3.61 (m, 5H), 3.39 (q, J = 9.1, 7.6 Hz, 3H), 3.31-2.84 (m, 9H), 2.71-2.54 (m, 1H), 1.69-1.33 (m, 10H), 1.21-0.82 (m, 7H). | | |

TABLE 1-continued

Characterization and Enzymatic Inhibition Data for Selected Compounds

| Cpd # | Structure | Data for R132H (μM) | Data for R132C (μM) | Synthesis Method | $^1$H-NMR | $[\alpha]_D^{20}$ (°) (C = 1, CH$_3$Cl$_3$) | ee (%) |
|---|---|---|---|---|---|---|---|
| 147 | 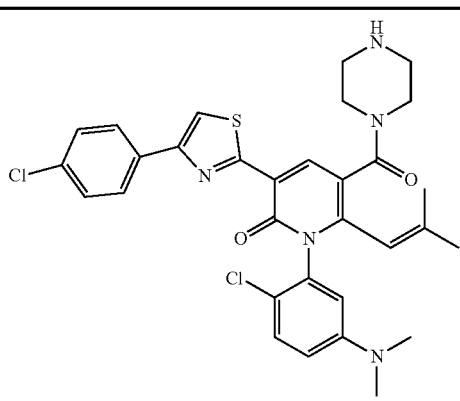 | A | A | Starting materials: 6,6-dimethyldihydro-2H-pyran-2,4(3H)-dione (step 1), Nitrile 1 (step 2), aniline 19 (step 3), Methods: V | $^1$H NMR (400 MHz, DMSO-d$_6$) δ 8.59 (s, 1H), 8.23 (d, J = 1.7 Hz, 1H), 8.18-7.99 (m, 2H), 7.59-7.43 (m, 2H), 7.37 (dd, J = 19.2, 9.0 Hz, 1H), 6.91-6.63 (m, 2H), 5.50 (s, 1H), 3.53 (d, J = 31.7 Hz, 1H), 3.25-3.10 (m, 1H), 2.89 (d, J = 20.1 Hz, 6H), 2.78-2.53 (m, 2H), 1.57 (dd, J = 5.3, 2.3 Hz, 6H), 1.35-1.14 (m, 2H). | | |
| 148 | 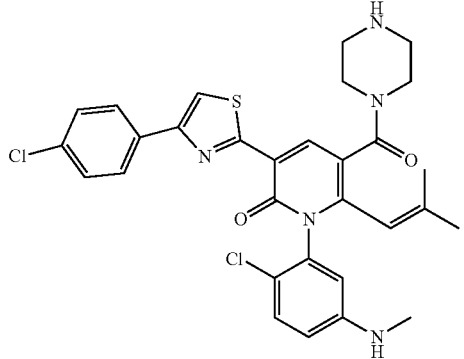 [SMILES: CNc1ccc(Cl)c(-n2c(C=C(C)C)c(C(=O)N3CCNCC3)cc(-c3nc(-c4ccc(Cl)cc4)cs3)c2=O)c1] | A | A | Starting materials: 6,6-dimethyldihydro-2H-pyran-2,4(3H)-dione (step 1), Nitrile 1 (step 2), aniline 20 (step 3), Methods: V. | $^1$H NMR (400 MHz, DMSO-d$_6$) δ 8.58 (s, 1H), 8.22 (s, 1H), 8.09 (d, J = 8.6 Hz, 2H), 7.57-7.42 (m, 2H), 7.28 (dd, J = 20.1, 8.8 Hz, 1H), 6.80-6.34 (m, 1H), 6.09 (q, J = 4.9 Hz, 1H), 5.50 (s, 1H), 3.66-3.37 (m, 1H), 3.27-3.12 (m, 2H), 2.79-2.53 (m, 6H), 2.30 (p, J = 1.9 Hz, 1H), 1.57 (d, J = 15.2 Hz, 7H). | | |
| 149 | 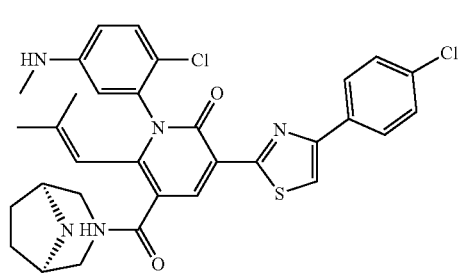 [SMILES: CNc1ccc(Cl)c(-n2c(C=C(C)C)c(C(=O)N3C[C@H]4CC[C@@H](C3)N4)cc(-c3nc(-c4ccc(Cl)cc4)cs3)c2=O)c1] | A | A | Starting materials: 6,6-dimethyldihydro-2H-pyran-2,4(3H)-dione (step 1), Nitrile 1 (step 2), aniline 20 (step 3), (1R,5S)-tert-butyl 3,8-diazabicyclo[3.2.1]octane-8-carboxylate (used in methods V, step 5); Methods: V. | $^1$H NMR (400 MHz, DMSO-d$_6$) δ 8.59 (s, 1H), 8.23 (s, 1H), 8.08 (d, J = 7.9 Hz, 2H), 7.52 (d, J = 8.3 Hz, 2H), 7.28 (dd, J = 24.9, 9.3 Hz, 1H), 6.87-6.55 (m, 2H), 5.46 (d, J = 21.3 Hz, 1H), 3.42-3.37 (m, 2H), 3.28-2.99 (m, 2H), 2.72-2.55 (m, 5H), 2.38-1.95 (m, 2H), 1.78-1.40 (m, 6H), 1.22 (d, J = 10.6 Hz, 2H). | | |
| 150 | 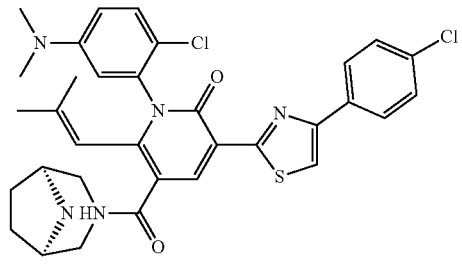 [SMILES: CC(C)=Cc1c(C(=O)N2C[C@H]3CC[C@@H](C2)N3)cc(-c2nc(-c3ccc(Cl)cc3)cs2)c(=O)n1-c1cc(N(C)C)ccc1Cl] | B | A | Starting materials: 6,6-dimethyldihydro-2H-pyran-2,4(3H)-dione (step 1), Nitrile 1 (step 2), aniline 19 (step 3), (1R,5S)-tert-butyl 3,8-diazabicyclo[3.2.1]octane-8-carboxylate (used in methods V, step 5); Methods: V. | $^1$H NMR (400 MHz, DMSO-d$_6$) δ 8.60 (s, 1H), 8.23 (s, 1H), 8.08 (d, J = 8.3 Hz, 2H), 7.52 (d, J = 8.4 Hz, 2H), 7.37 (dd, J = 23.5, 8.7 Hz, 1H), 6.78 (d, J = 7.0 Hz, 2H), 5.49 (s, 1H), 3.43-3.34 (m, 2H), 2.89 (d, J = 27.8 Hz, 2H), 2.64 (p, J = 1.9 Hz, 3H), 2.30 (p, J = 1.8 Hz, 3H), | | |

TABLE 1-continued

Characterization and Enzymatic Inhibition Data for Selected Compounds

| Cpd # | Structure | Data for R132H (μM) | Data for R132C (μM) | Synthesis Method | $^1$H-NMR | $[\alpha]_D^{20}$ (°) (C = 1, CH$_3$Cl$_3$) | ee (%) |
|---|---|---|---|---|---|---|---|
| | | | | | 1.71-1.46 (m, 9H), 1.31-1.14 (m, 3H). | | |
| 151-1 | 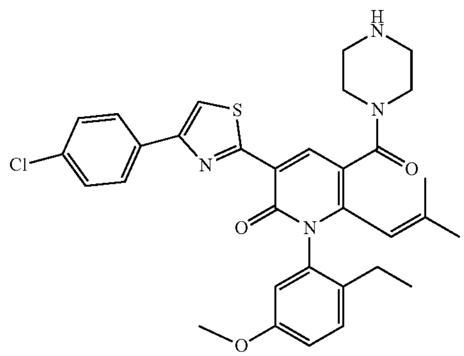 [SMILES: CCc1ccc(OC)cc1-n1c(C=C(C)C)c(C(=O)N2CCNCC2)cc(-c2nc(-c3ccc(Cl)cc3)cs2)c1=O] | A | A | Chiral separation of 151: ChiralPak IA (5 × 50 cm, 20 um); Hex/EtOH/DEA (40:60:0.04); 35 mL/min | $^1$H NMR (400 MHz, Chloroform-d) δ 8.82 (bs, 1H), 7.93 (d, J = 8.6 Hz, 1H), 7.58 (s, 1H), 7.44-7.36 (m, 3H), 7.30 (d, J = 8.6 Hz, 1H), 6.98 (dd, J = 8.7, 2.7 Hz, 1H), 6.68-6.46 (m, 1H, rotameric), 5.60-5.28 (m, 1H, rotameric), 4.16-2.84 (m, 9H), 2.42-2.02 (m, 2H), 1.70-1.60 (m, 6H), 1.16-0.81 (m, 3H). | +3.8 | >98 |
| 151-2 | 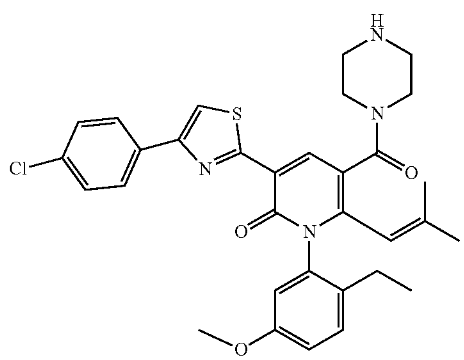 [SMILES: CCc1ccc(OC)cc1-n1c(C=C(C)C)c(C(=O)N2CCNCC2)cc(-c2nc(-c3ccc(Cl)cc3)cs2)c1=O] | A | B | Chiral separation of 151: ChiralPak IA (5 × 50 cm, 20 um); Hex/EtOH/DEA (40:60:0.04); 35 mL/min | $^1$H NMR (400 MHz, Chloroform-d) δ 8.81 (bs, 1H), 7.93 (d, J = 8.6 Hz, 1H), 7.57 (s, 1H), 7.44-7.34 (m, 3H), 7.30 (d, J = 8.6 Hz, 1H), 6.97 (dd, J = 8.7, 2.7 Hz, 1H), 6.67-6.49 (m, 1H, rotameric), 5.61-5.29 (m, 1H, rotameric), 4.14-2.86 (m, 9H), 2.41-2.03 (m, 2H), 1.71-1.61 (m, 6H), 1.17-0.80 (m, 3H). | −2.8 | 80.9 |

What is claimed is:

1. A compound of Formula II:

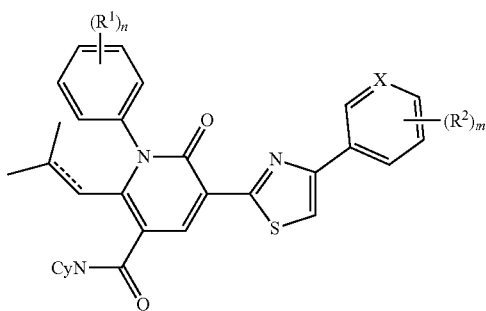

(II)

or a pharmaceutically acceptable salt thereof, wherein

CyN is a cyclic amine group bound via a nitrogen atom that is optionally substituted with one or more substituents independently chosen from halogen, $C_1$-$C_2$alkyl, and $C_1$-$C_2$alkoxy;

X is C or N;

$R^1$ and $R^2$ are each independently a halogen, CN, $CF_3$, $CHF_2$, $CH_2F$, a $C_1$-$C_{10}$alkyl group, a $C_1$-$C_{10}$alkoxy group, a di($C_1$-$C_5$alkyl)amino;

m and n are each independently 1, 2, or 3; and

------ represents either a single bond or a double bond, wherein the racemic mixture of 3-(4-(4-chlorophenyl)thiazol-2-yl)-1-(2-ethyl-5-methoxyphenyl)-6-(2-methylprop-1-en-1-yl)-5-(piperazine-1-carbonyl)pyridin-2(1H)-one atropisomers is excluded.

2. The compound or salt of claim 1, wherein the compound is an atropisomer of Formula II-A:

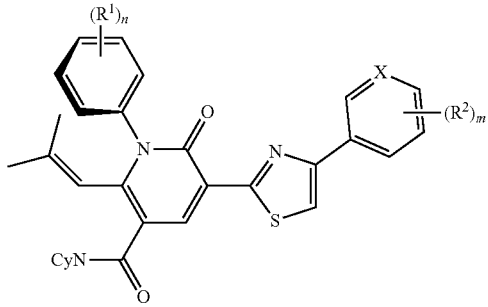
(II-A)

wherein at least one $R^1$ group is an ortho substituent and the atropisomer of Formula II-A is present in excess of its corresponding enantiomer.

3. The compound or salt of claim 1, wherein the compound is an atropisomer compound of Formula II-B:

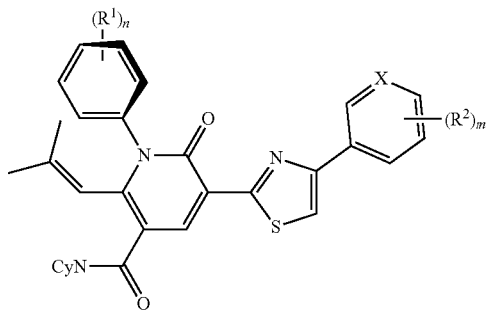
(II-B)

wherein at least on $R^1$ group is an ortho substituent and the atropisomer of Formula II-B is present in excess of its corresponding enantiomer.

4. The compound or salt of claim 1, wherein the compound is an atropisomer of Formula II-C:

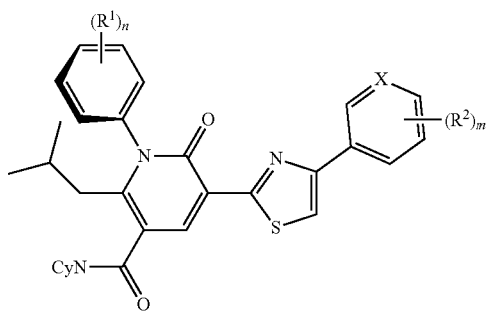
(II-C)

wherein at least one $R^1$ group is an ortho substituent and the atropisomer of Formula II-C is present in excess of its corresponding enantiomer.

5. The compound or salt of claim 1, wherein the compound is an atropisomer compound of Formula II-D:

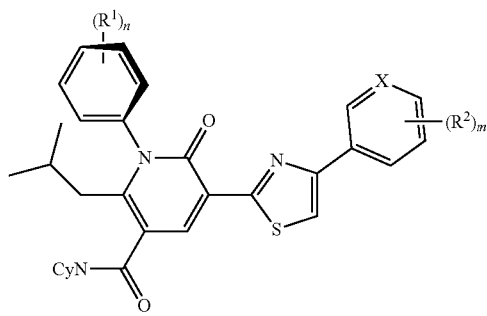
(II-D)

wherein at least on $R^1$ group is an ortho substituent and the atropisomer of Formula II-D is present in excess of its corresponding enantiomer.

6. The compound or salt of claim 1, wherein m is 1 and $R^2$ is a 4-substituent.

7. The compound or salt of claim 1, wherein $R^2$ is 4-Cl, 4-$CF_3$, 4-$CHF_2$, 4-$CH_3O$, or 4-CN.

8. The compound or salt of claim 1, wherein X is C and $R^2$ is 4-Cl, 4-$CF_3$, 4-$CHF_2$, or 4-NC; or.

X is N and $R^2$ is 4-$CF_3$, 4-$CHF_2$, or 4-$CH_3O$.

9. The compound or salt of claim 1 wherein n is 2 and $R^1$ is 2-$C_2H_5$, 5-$CH_3O$; or 2-$C_2H_5$, 5-Cl; or 2-Cl, 5-$(CH_3)_2N$; or 2-$C_2H_5O$, 5-$C_2H_5O$; or 2-$C_2H_5O$, 5-Cl; or 3-$C_2H_5O$, 5-NC, or di-2,6-$C_2H_5$.

10. The compound or salt of claim 1, wherein CyN— is:

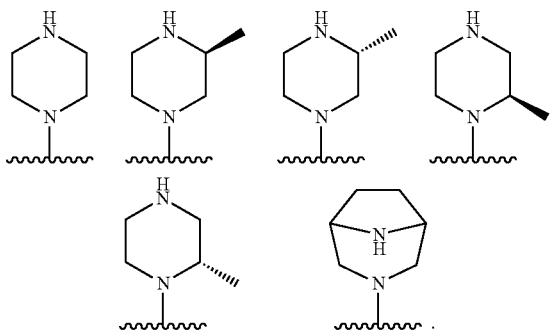

11. The atropisomer compound or salt thereof, of claim 2, wherein the atropisomer compound is one of the following compounds:

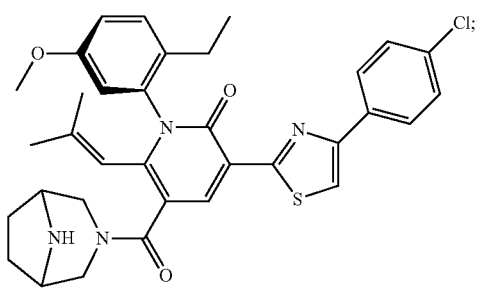

75
-continued
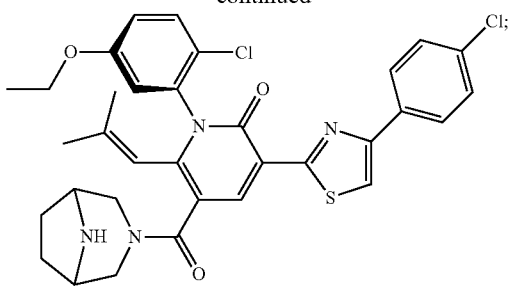
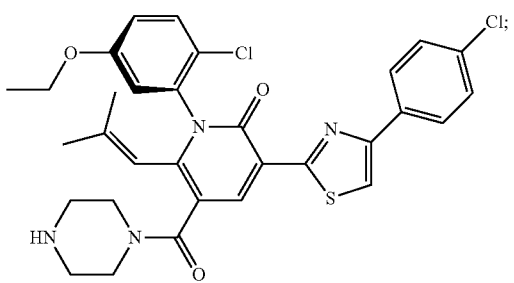
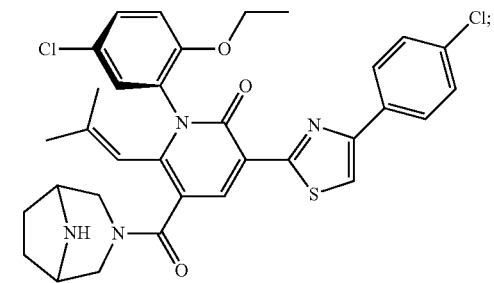
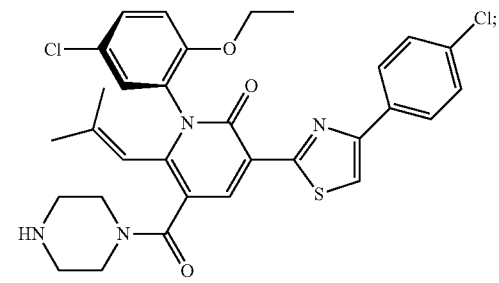
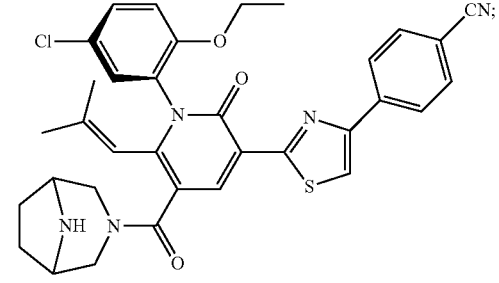
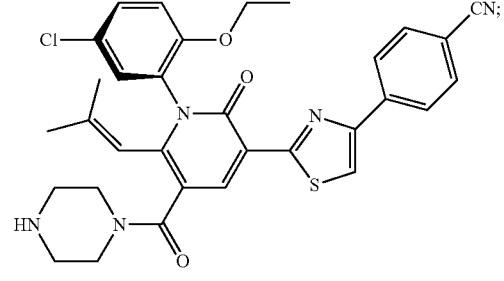
76
-continued
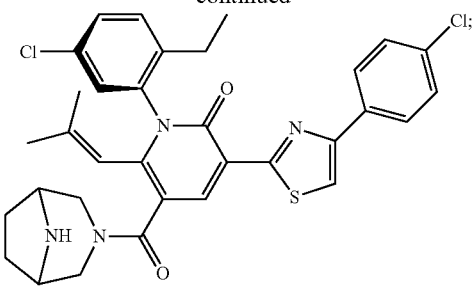
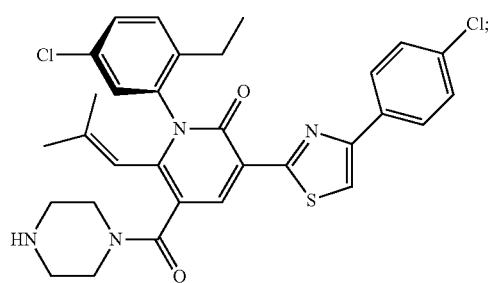
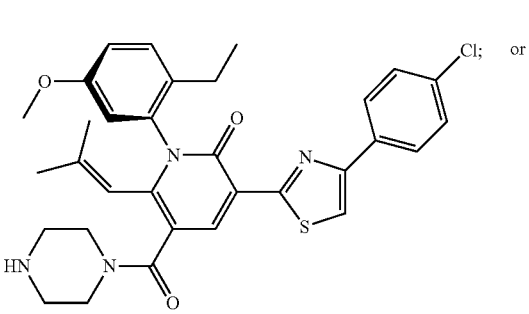
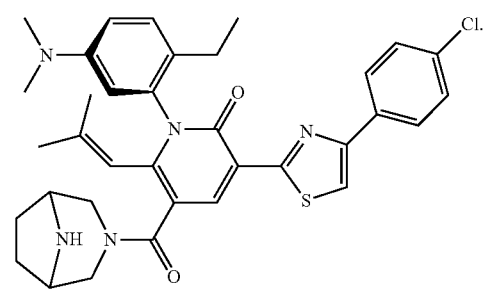
12. The atropisomer compound or salt of claim 3, wherein the atropisomer compound is one of the following compounds:
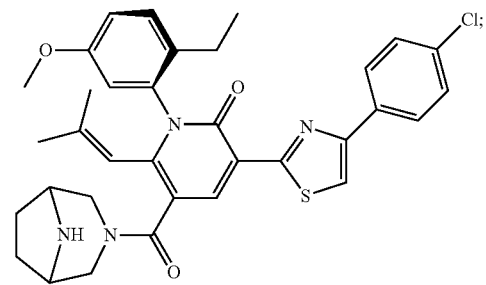

-continued
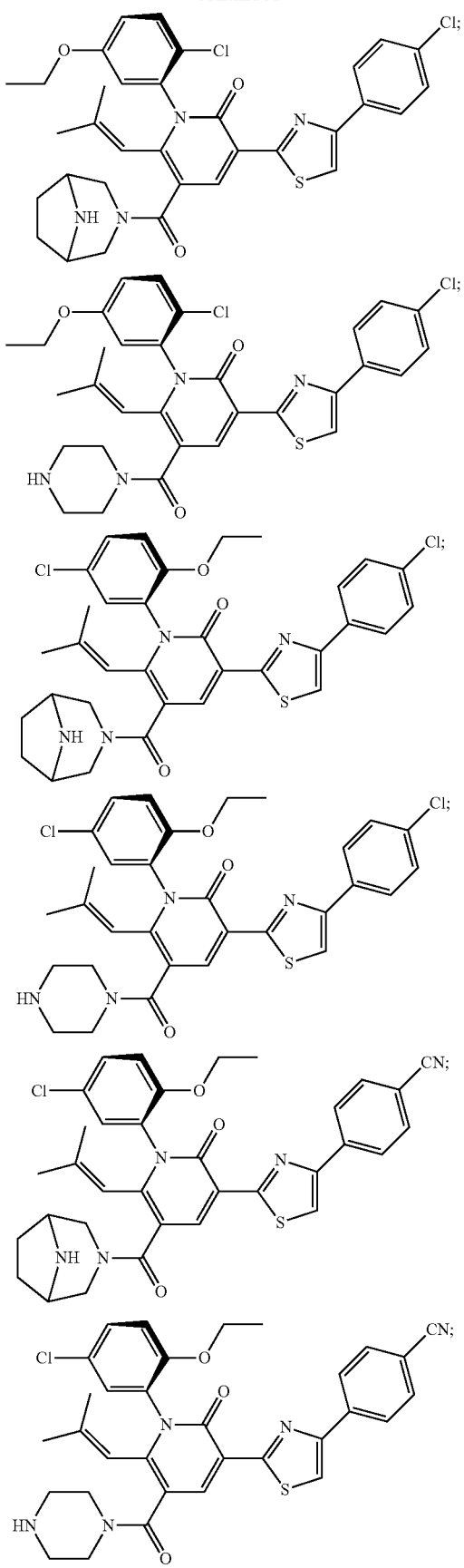
-continued
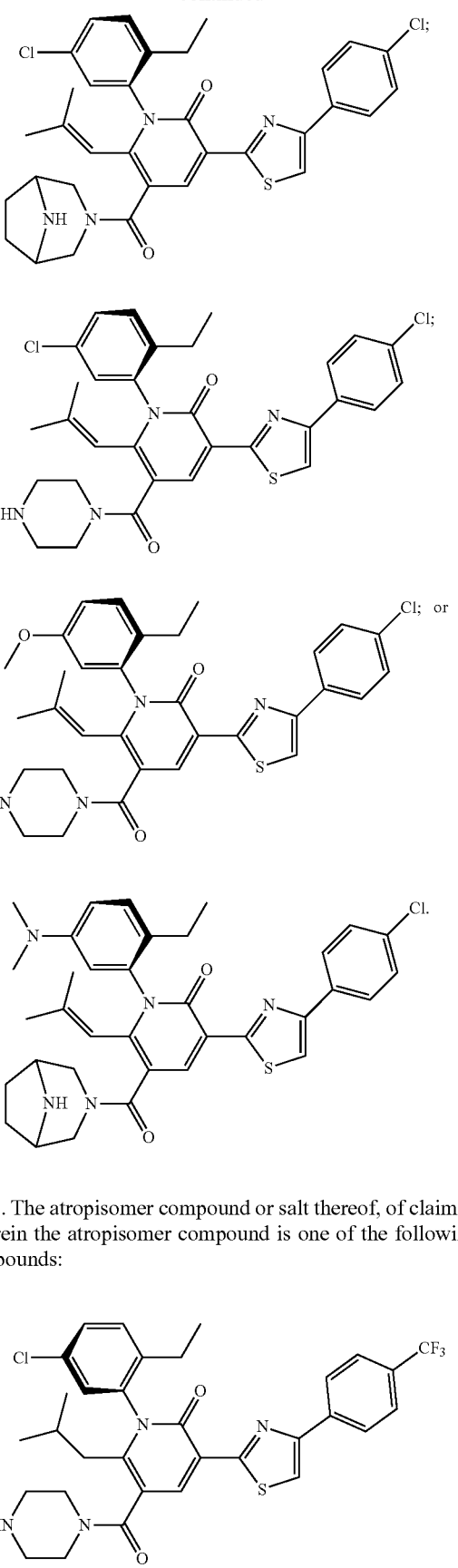
13. The atropisomer compound or salt thereof, of claim 4, wherein the atropisomer compound is one of the following compounds:

-continued

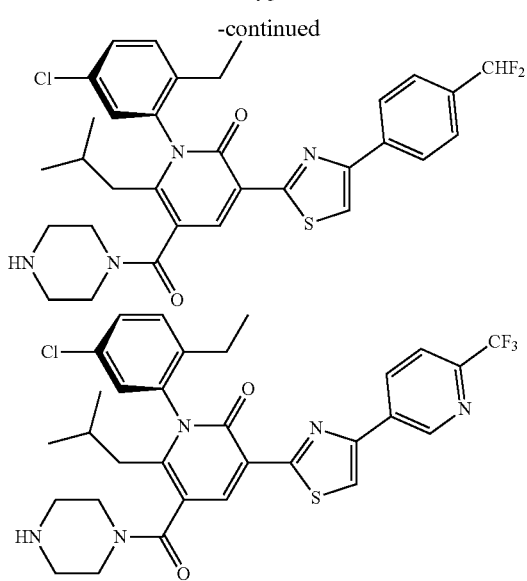

14. The atropisomer compound or salt thereof, of claim 5, wherein the atropisomer compound is one of the following compounds:

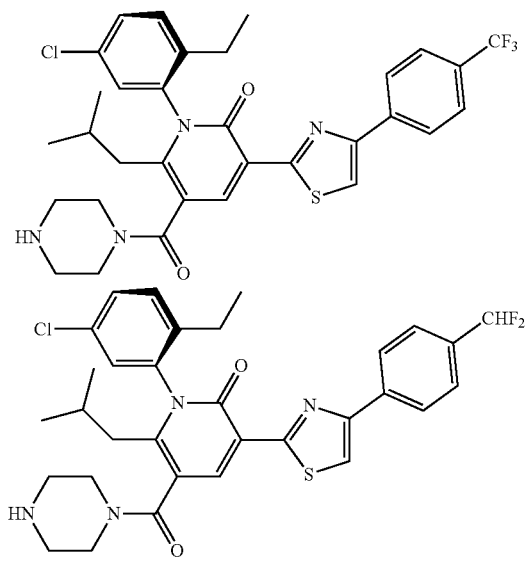

-continued

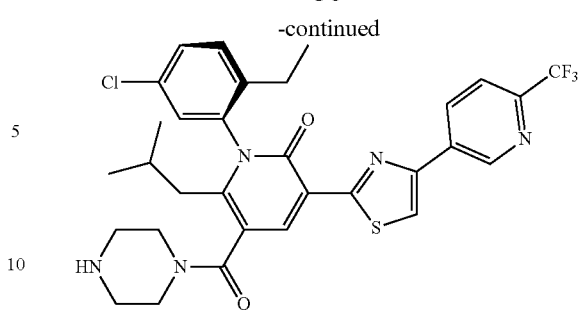

15. A pharmaceutical composition comprising a compound or salt of claim 1, together with a pharmaceutically acceptable carrier.

16. A method of treating a cancer characterized by the presence of an IDH1 mutation, wherein the IDH1 mutation results in a new ability of the enzyme to catalyze the NADPH-dependent reduction of α-ketoglutarate to R(−)-2-hydroxyglutarate in a patient, comprising the step of providing to a patient in need thereof a therapeutic agent, wherein the therapeutic agent is a compound or salt thereof of claim 1.

17. The method of claim 16, wherein the IDH1 mutation is an IDH1 R132H or IDH1 R132C mutation.

18. The method of claim 16, wherein the cancer is selected from glioma (glioblastoma), acute myelogenous leukemia, acute myeloid leukemia, myelodysplastic/myeloproliferative neoplasms, sarcoma, chronic myelomonocytic leukemia, non-Hodgkin lymphoma, astrocytoma, melanoma, non-small cell lung cancer, cholangiocarcinomas, chondrosarcoma, or colon cancer.

19. A method of treating Ollier disease or Maffuci syndrome, comprising providing a therapeutic agent to a patient in need thereof, wherein the therapeutic agent is a compound or salt thereof of claim 1.

20. The method of claim 16, further comprising administering to the patient in need thereof at least one additional therapeutic agent.

\* \* \* \* \*